(12) United States Patent
Hood et al.

(10) Patent No.: US 6,488,029 B1
(45) Date of Patent: Dec. 3, 2002

(54) SELF-CONTAINED TRANSPORTABLE LIFE SUPPORT SYSTEM

(75) Inventors: David Darby Hood, Signal Hill; David Sherrill, Tujunga; Todd Douglas Kneale, La Habra; Louis Stephen Toth, La Palma; David Michael Stanley, Anaheim; Gene Bruce Moore, Orange; Mark Lane Berry, Chino Hills; Robert Michael Garcia, Laguna Hills; William Richard Sobko, Torrance; Donald Hanks, Woodland Hills; Douglas Ellwood Shultz, Brea; John Roger Brayton, Gardena; Walter Dennis Clark, Fullerton, all of CA (US)

(73) Assignee: Integrated Medical Systems, Inc., Signal Hill, CA (US)

( * ) Notice: Subject to any disclaimer, the term of this patent is extended or adjusted under 35 U.S.C. 154(b) by 0 days.

(21) Appl. No.: 09/221,223

(22) Filed: Dec. 23, 1998

Related U.S. Application Data

(63) Continuation of application No. 08/667,693, filed on Jun. 21, 1996, now Pat. No. 5,975,081.

(51) Int. Cl.$^7$ .............................................. A61G 15/00
(52) U.S. Cl. ...................................... 128/845; 870/897
(58) Field of Search ................................. 128/845, 846, 128/869, 870, 897; 600/21, 22

(56) References Cited

U.S. PATENT DOCUMENTS 1,200,852 A   10/1916   Kern
1,258,694 A   3/1918    Miller (List continued on next page.)

FOREIGN PATENT DOCUMENTS

| GB | 117     | of 1915 |
|----|---------|---------|
| AU | 9500477 | 8/1995  |
| DE | 1416697 | 11/1972 |
| EP | 343077  | 11/1989 |
| FR | 1373384 | 11/1962 |

OTHER PUBLICATIONS

Buchanan Aircraft Corporation; (M.I.R.F.) *Mobile Intensive Care Rescue Facility*; undated; 4 pgs; Queensland, Australia.

Spectrum Aeromed; *Critical Care in the Air*; undated; 2 pgs; Wheaton, MN.

Spectrum Aeromed; *Above and Beyond*; 1995; 9 pgs; Wheaton, MN.

MOBI™: *Mobile Intensive Care Unit*; undated; 2 pgs.

Lifeport, Inc.; *The Results Of Innovation*; undated; Vancouver, WA.

Mobile Intensive Care Resuce Facility (MIRF).

Aeromed Systems, Inc.—Specification/AMT 300.

*Primary Examiner*—Michael A. Brown
(74) *Attorney, Agent, or Firm*—Stetina Brunda Garred & Brucker

(57) ABSTRACT

A self-contained transportable life support system for resuscitation, stabilization, and transport of a patient has an environmentally controlled housing for receiving and supporting a patient and a plurality of medical devices disposed within the housing. A control circuit attached to the housing has at least a portion thereof extending to an external surface of the housing for regulating operation of the medical devices and environmental conditions of within the housing in response to monitored life support conditions of the patient.

53 Claims, 31 Drawing Sheets

Microfiche Appendix Included
(40 Microfiche, 40 Pages)

U.S. PATENT DOCUMENTS

| | | | |
|---|---|---|---|
| 1,287,855 A | 12/1918 | Brand | |
| 1,473,862 A | 3/1923 | Caswell et al. | |
| 2,704,989 A | 3/1955 | Konecny | 114/5 |
| 2,837,778 A | 6/1958 | Kern | 20/2 |
| 3,050,331 A | 8/1962 | Mansen | 296/27 |
| 3,148,911 A | 9/1964 | Boyer et al. | 296/19 |
| 3,376,059 A | 4/1968 | Corl | 287/99 |
| 3,492,042 A | 1/1970 | Nachtigall, Jr. | 296/24 |
| 3,531,151 A | 9/1970 | Branfield | 296/23 |
| 3,761,968 A | 10/1973 | Besler | 5/92 |
| 3,775,782 A | 12/1973 | Rice et al. | 5/82 |
| 3,840,265 A | 10/1974 | Stirling et al. | 296/19 |
| 4,060,079 A | 11/1977 | Reinhold, Jr. | 128/145.8 |
| 4,161,172 A * | 7/1979 | Pickering | 600/22 |
| 4,224,936 A | 9/1980 | Cox | 128/132 |
| 4,352,991 A | 10/1982 | Kaufman | 307/9 |
| 4,425,978 A | 1/1984 | Star | 180/243 |
| 4,584,989 A | 4/1986 | Stith | |
| 4,680,790 A | 7/1987 | Packard et al. | 379/432 |
| 4,715,385 A | 12/1987 | Cudahy et al. | 128/710 |
| 4,724,844 A | 2/1988 | Rafelson | 128/670 |
| 4,747,172 A | 5/1988 | Hohol et al. | 5/507 |
| 4,757,811 A | 7/1988 | Clark | 128/134 |
| 4,768,241 A | 9/1988 | Beney | 5/60 |
| 4,780,919 A | 11/1988 | Harrison | 5/60 |
| 4,783,109 A | 11/1988 | Bucalo | 296/20 |
| 4,957,121 A | 9/1990 | Icenogle et al. | 128/897 |
| 4,981,139 A | 1/1991 | Pfohl | 128/671 |
| 5,005,230 A | 4/1991 | Congdon | 5/60 |
| 5,016,307 A | 5/1991 | Rebar | 5/503 |
| 5,034,181 A | 7/1991 | Billiu | 264/517 |
| 5,050,254 A | 9/1991 | Murphy | 5/82 |
| 5,077,843 A | 1/1992 | Dale et al. | 5/60 |
| 5,084,922 A | 2/1992 | Louit | 5/81.1 |
| 5,092,722 A | 3/1992 | Reazer, III et al. | 410/104 |
| 5,111,818 A | 5/1992 | Suzuki et al. | 128/644 |
| 5,117,521 A | 6/1992 | Foster et al. | 5/510 |
| 5,121,514 A | 6/1992 | Rosane | 5/628 |
| 5,173,142 A | 12/1992 | Billiu | 156/245 |
| 5,229,052 A | 7/1993 | Billiu | 264/115 |
| 5,236,390 A | 8/1993 | Young | 454/95 |
| 5,306,026 A | 4/1994 | Jesse | 280/18 |
| 5,307,818 A | 5/1994 | Segalowitz | 128/696 |
| 5,331,549 A | 7/1994 | Crawford, Jr. | 364/413.02 |
| 5,335,651 A | 8/1994 | Foster et al. | 128/202.13 |
| 5,338,588 A | 8/1994 | Billiu | 428/36.3 |
| 5,342,121 A * | 8/1994 | Koria | 600/21 |
| 5,404,877 A | 4/1995 | Nolan et al. | 128/671 |
| 5,421,340 A * | 6/1995 | Stanga | 600/21 |
| 5,441,047 A | 8/1995 | David et al. | 128/670 |
| 5,474,574 A | 12/1995 | Payne et al. | 607/7 |
| 5,494,051 A | 2/1996 | Schneider, Sr. | 128/870 |
| 5,497,766 A | 3/1996 | Foster et al. | 128/200.24 |
| 5,511,553 A | 4/1996 | Segalowitz | 128/696 |
| 5,570,483 A | 11/1996 | Williamson | 5/83.1 |
| 5,590,648 A | 1/1997 | Mitchell et al. | 128/630 |
| 5,615,430 A | 4/1997 | Nambu et al. | 5/600 |
| 5,626,151 A * | 5/1997 | Linden | 128/897 |
| 5,630,238 A | 5/1997 | Weismiller et al. | 5/600 |
| 5,664,270 A | 9/1997 | Bell et al. | 5/600 |
| 5,680,661 A | 10/1997 | Foster et al. | 5/618 |
| 5,687,717 A | 11/1997 | Halpern et al. | 128/630 |
| 5,749,374 A | 5/1998 | Schneider, Sr. | 128/870 |

* cited by examiner

DEFIBRILLATOR OFF

DEFIBRILLATOR ON
AND CHARGING

SELF-CONTAINED TRANSPORTABLE LIFE SUPPORT SYSTEM

FIELD OF THE INVENTION

The present application is a continuation of U.S. application Ser. No. 08/667,693 entitled SELF-CONTAINED TRANSPORTABLE LIFE SUPPORT SYSTEM filed Jun. 21, 1996 now U.S. Pat. No. 5,975,081.

MICROFICHE APPENDIX

This patent application contains a microfiche appendix which contains a program listing for the computer program used in the practice of this invention, and a set of (40) microfiche cards.

FIELD OF THE INVENTION

The present invention relates generally to medical devices utilized to treat intensive care patients and more particularly to a self-contained transportable life support system which is utilized in the resuscitation, stabilization, and transport of medical patients such as heart attack victims, stroke victims, accident victims and battlefield casualties.

BACKGROUND OF THE INVENTION

The need to transport medical patients and persons suffering from various medical emergency conditions such as heart attacks, strokes, etc. is well-known. Medical personnel speak of a "golden hour" within which such a medical patient must be transported to a medical facility so that proper medical care can be provided therefor. The survival rate for such medical patients is greatly enhanced if they are transported to the medical facility within the golden hour.

However, as those skilled in the art will appreciate, it is often difficult to transport a patient to a remotely located medical facility in a timely manner, particularly within the golden hour. Frequently accidents occur at remote locations and thus require a substantial amount of time to transport the medical patient to a distant hospital. Also, in battlefield situations, it is frequently impossible to transport a casualty immediately. In either instance, a hospital may be located hundreds, if not thousands, of miles from a hospital, thus necessitating several hours of transport time. As such, it is frequently beneficial to perform various emergency medical procedures at the site of the medical problem, and then to attempt to provide ongoing medical care during transport. By providing such early emergency medical care and by continuing medical treatment during transport to a remote hospital, the mortality rate of such transported medical patients is substantially reduced.

It is well-known to use various different medical devices in the field, i.e., at locations remote from a medical facility, so as to enhance a medical patient's chance of survival. For example, it is well-known to use an ECG and a defibrillator upon heart attack victims, so as to monitor the condition thereof and so as to provide medical treatment therefor in the field.

Typically, the medical patient is placed upon a stretcher and then various different medical devices are used thereupon, as necessary. During transport the medical devices may either be temporarily disconnected from the patient or, alternatively, may be hand carried along therewith by additional personnel. However, disconnection of the medical devices from the patient results in the undesirable disruption of medical monitoring or treatment therefor. Hand carrying the medical devices along with the patient requires extra personnel, which may not be available, or for which there may not be adequate room within the transport vehicle.

As such, it is desirable to provide a system for transporting a medical patient wherein the medical devices are carried along with the stretcher. In an attempt to provide such a system for transporting a medical patient while facilitating the continuous use of medical devices thereupon, the Mobile Intensive Care Rescue Facility (MIRF) was developed by the Royal Australian Army Medical Corp. The MIRF is intended to provide sufficient medical equipment to have the capabilities of an intensive care hospital ward. The MIRF is designed so as to facilitate the removal and replacement of the various pieces of medical equipment therefrom for maintenance. The MIRF is specifically designed to accommodate two major roles: the transfer of critically ill people from one point to another, such as from a ward to an x-ray room or from one hospital to another; and the bringing of life support systems quickly to the scene of an accident or other medical emergency.

The MIRF can be configured to include a blood pressure cuff, an invasive blood pressure monitor, a body temperature sensor, a heart rate sensor (finger clip sensor), an oxygen saturation sensor, an exhaled air carbon dioxide sensor, and an electrocardiograph, so as to facilitate medical monitoring of a patient. Further, the MIRF can include a ventilation system, a volumetric infusion pump, a syringe pump, a suction unit, and a defibrillator so at to facilitate medical treatment.

However, since the various medical devices of the MIRF are not integrated with the housing thereof, the inclusion of all of the medical devices results in a system having substantial weight. Further, since the various medical devices of the MIRF are not integrated with the housing thereof, the volume occupied thereby and the electrical power consumption of the medical devices thereof are not optimal.

As such, it would be desirable to provide an integrated system which utilizes a single power supply and which eliminates redundant components, so as to achieve a substantial reduction in weight, volume, and power consumption.

Another contemporary system is the MOBI described in U.S. Pat. No. 4,957,121, issued to Icenogle et al. on Sep. 18, 1990. The MOBI is similar to the MIRF in concept. That is, like the MIRF, the MOBI utilizes off-the-shelf medical devices which are contained attached to housing thereof, so as to be transportable therewith, thus eliminating disruptions in the medical care provided thereby during transport.

However, also like the MIRF, the MOBI is not an integrated system and thus possesses substantially greater weight, volume, and power consumption than desirable.

Further examples of such contemporary life support systems include those disclosed in U.S. Pat. Nos. 4,584,989; 4,352,991; 4,691,397; 3,304,116; and 3,341,246.

U.S. Pat. No. 4,584,989 discloses a life support stretcher bed adapted to accommodate patients in intensive or cardiac care units in hospitals. The life support stretcher bed is broadly adapted for electrical medical devices, medical supplies and features an under carriage including a support structural, wheels, a patient housing with a mattress, an electrical power source and supports for mounting the medical equipment.

U.S. Pat. No. 4,352,991 teaches a life support system adapted for field use in a vehicle with available power and includes electrically operable life support units, means for supporting the life support units, a patient stretcher, and a dc power source adapted for battery or remote power source.

U.S. Pat. No. 4,691,397 teaches a device for carrying the life supporting devices of a bedridden patient including a table like means for supporting the devices, an IV holder, wheeled transport means and a hospital bed footboard securing means.

U.S. Pat. No. 3,304,116 teaches a multiple purpose wheeled carriage capable of supporting a stretcher carrying a patient, adapted with four castered wheels, a fifth wheel, a rectangular frame, a fluid pressure actuated means for vertical adjustment, operating and control means and patient support means.

U.S. Pat. No. 3,341,246 teaches a hospital stretcher adapted broadly with a litter structure having telescopic post elements and other means for manipulating the patient to various positions.

It is frequently desirable to isolate a medical patient from the environment during transport thereof to a medical facility. It is also frequently desirable to isolate the medical patient from care givers and other personnel. Isolating the medical patient from care givers and other personnel may be desirable when the medical patient has a suppressed immune system, open wound, or when the presence of a contagion is suspected among the care givers and/or other personnel. It is desirable to isolate the patient from the environment when the environment contains substances which may be detrimental to the medical patient. For example, if the patient has suffered severe blood loss or is experiencing difficulty breathing, then it is desirable to prevent the patient from breathing dust, engine exhaust, smoke, etc. It is also desirable to isolate the medical patient from the environment when bacteriological, chemical and/or radiological hazards are present, as may occur during battlefield conditions.

It may be desirable to isolate the care givers from the medical patient in instances where the medical patient is suspected of having a contagious disease, or has been exposed to bacteriological, chemical or radiological contamination. As such, it is desirable to provide a means for isolating the patient from the environment and care givers, as well as isolating the care givers from the patient.

As discussed above, increased transit times make the initial preparation of the medical patient substantially more crucial. This may include resuscitation, and in any event must be sufficient to avoid causing further injury to the medical patient during transport. It is generally also necessary to provide continuous care, i.e., stabilization, for the patient during transit.

Proper care during transit frequently includes ventilation, suction, fluid infusion and possibly defibrillation. Further, it is highly desirable to monitor blood pressure, temperature and respiration. It may also be desirable to monitor ventilation gases for $pO_2$ and $pCO_2$, and also to monitor $O_2$ saturation, cardiac output and local blood flow. By providing such care and monitoring, the probability of survival for the medical patient is greatly enhanced. Variations in the monitored parameters may signal the need for an immediate change in the medical care being provided.

Further, such longer transit times make environmental protection for the medical patient even more desirable. For example, increased transit time makes loss of body heat a much greater concern. Thus, protection from cold and rain is desirable.

Although, as discussed above, various different mobile intensive care systems have been proposed, such contemporary mobile intensive care systems are not suitable for transport via military vehicles having standard NATO stretcher holders. Such military vehicles require that the stretcher or other housing upon which the medical patient rests, along with the medical patient, fit within a well defined and rigid envelope so as not to interfere with adjacent vehicle structures and/or other patients and stretchers. No contemporary mobile intensive care system is known which fits with this envelope. Thus, such prior art mobile intensive care systems cannot be efficiently carried via such military vehicles. This means that fewer such battlefield casualties can be transported via a particular military vehicle when such contemporary mobile intensive care systems are utilized, thus inherently causing undesirable delays in transport and also undesirably increasing the risk of mortality.

The UH-60 Blackhawk helicopter, the UH-1 Huey helicopter, the HumVee ambulance, the C-130 Fixed Wing aircraft, and the C-141 Fixed Wing aircraft all utilize standard NATO stretcher holders such that a plurality of such NATO stretchers, having battlefield casualties laying thereupon, can be efficiently carried thereby. For example, in the UH-60 Blackhawk helicopter, such stretchers are mounted to a vertical bulkhead carousel in a stacked configuration, such that the number of battlefield casualties so carried is maximized.

In order to facilitate evacuation of a medical patient from the battlefield to a remote hospital, a number of such military vehicles are commonly used. For example, a HumVee may be utilized to transport the medical patient to a helipad where the medical patient is then transported via a UH-60 Blackhawk or UH-1 Huey helicopter to an airfield. From the airfield the medical patient is then transported, typically, via C-130 or C-141 fixed wing aircraft to an airport near the remote hospital. As mentioned above, all of these military vehicles presently have stretcher holders which are specifically configured to hold the NATO standard stretcher.

In order to be carried via such military vehicles, a life support system must fit within the standard stretcher holders of such vehicles and still leave enough room for the medical patient resting thereon. Of course, the support system must not interfere with adjacent, e.g., stacked, medical patients and/or life support systems. However, to date, no such life support systems are known which are specifically configured to be compatible with such standard stretcher holders.

Since contemporary mobile intensive care systems are not configured for transport via military vehicles utilizing standard NATO stretcher mounts, it is frequently necessary to remove the medical patient therefrom, so as to facilitate such transport. Such removal of the medical patient from a contemporary mobile intensive care system may require disconnection from or disruption of desirable medical treatment, thus increasing the risk of mortality. Further, as those skilled in the art will appreciate, removing a medical patient from a mobile intensive care system, such that the medical patient can be placed upon a stretcher for transport aboard a military vehicle utilizing standard NATO stretcher mounts, tends to exacerbate existing injuries and thus tends to further increase the rate of mortality for such battlefield casualties.

As such, it is desirable to provide a single mobile intensive care system upon which the medical patient is placed at the battlefield and upon which the medical patient remains throughout the entire trip to the remote hospital.

Further, such contemporary mobile intensive care systems require skilled operators having extensive training to assure that proper care is provided to the medical patient. Although mobile intensive care systems requiring such extensive training are generally suitable for use in civilian applications, it is highly desirable to minimize the amount of skill and training required for use in battlefield situations. This allows medics or medical care givers to be trained in a minimum amount of time. It also facilitates use of the life support system when trained personnel are not available (as is often the case in battlefield situations). Thus, it is desirable to provide a mobile intensive care system which requires minimal skill and training for such battlefield applications.

Further, since the individual medical devices of contemporary mobile intensive care systems are not integrated with one another, the medical care provided thereby is not optimized. This lack of integration further enhances the requirement for trained personnel. Additionally, such lack of integration necessitates constant monitoring of the medical patient during transport. Constant monitoring of the medical patient is often either difficult or impossible, since skilled medical personnel are generally either not available or are highly taxed during such evacuation procedures.

As such, it is desirable to provide means for preparing a medical patient for a lengthy transport, i.e., stabilizing the medical patient, and for providing the necessary medical care during such transport. It is also desirable to provide medical devices which are integrated so as to mitigate the skill and training required for the proper operation thereof, and so as to facilitate automated operation thereof such that minimal attention of a care giver is required during transport. It is also desirable to provide a mobile intensive care system wherein the medical devices thereof cooperate with one another so as to optimize medical care provided thereby. Further, it is desirable to provide a mobile intensive care system which protects the medical patient from the environment, so as to mitigate the detrimental effects thereof.

SUMMARY OF THE INVENTION

The present invention specifically addresses and alleviates the above-mentioned deficiencies associated with the prior art. More particularly, the present invention comprises a self-contained transportable life support system for resuscitation, stabilization, and transport of a patient. As used herein, the terms medical patient and patient are defined to include patients and/or victims of any accident and/or medical condition resulting in the need for emergency medical care. Thus, the term medical patient includes victims of heart attacks and strokes, as well as victims of accidents and wartime casualties. The system comprises an environmentally controlled housing for receiving and supporting a patient, and a plurality of medical devices disposed within the housing. A control circuit is attached to the housing such that at least a portion of the control circuit extends to an external surface of the housing. The control circuit regulates operation of the medical devices and environmental conditions within the housing in response to monitored life support conditions of the patient.

The control circuit is programmably controllable to regulate operation of the medical devices and life support conditions of the patient independent of operator intervention. The control circuit preferably comprises a closed-loop control system.

The medical devices preferably comprise a ventilator, suction device, fluid infuser, defibrillator, oxygen enricher/ generator, electrocardiograph, electroencephalograph blood pressure monitor, temperature sensor, respiration volume and rate monitor, ventilator gas monitor, $O_2$ saturation monitor, and a cardiac rate and cardiac output and local blood flow monitor, and a device for performing blood chemistry analysis.

A heater is preferably disposed within the housing and in electrical communication with the control circuit, for heating an interior portion of the housing so as to maintain the interior portion above a predetermined minimum temperature.

Similarly, a cooler is preferably disposed within the housing and in electrical communication with the control circuit, for cooling an interior portion of the housing so as to maintain the interior portion below a predetermined maximum temperature.

An air filtration system is preferably disposed within the housing and in electrical communication with the control circuit, for filtering air within the housing.

The medical devices comprise at least one medical monitoring device for monitoring at least one life support condition of the patient and at least one medical treatment device for providing medical treatment to the patient. The medical devices providing treatment are regulatable by the control circuit in response to signals from the medical monitoring devices.

A communication circuit attached to the housing provides communications between the control circuit and a remote location. The communication circuit preferably comprises a transmitter for transmitting information representative of patient life support conditions and patient physiological status and a receiver for receiving externally generated remote control signals. The control circuit is responsive to the remote control signals, such that patient life support conditions are regulatable in response to the remote control signals. The control circuit preferably comprises a general purpose microprocessor.

The housing has an interior portion which is configured to receive and engage a stretcher. An exterior portion is configured to engage vehicular mounted stretcher supports.

The housing preferably comprises four stretcher retention members disposed within the housing for receiving and engaging a stretcher within the housing. Each of the stretcher retention members comprises a stretcher engagement mechanism operative to provide locking engagement to the stretcher solely in response to placement of the stretcher upon the stretcher engagement mechanism.

The control circuit preferably comprises first and second battery sections. A charging circuit selectively charges either one of the first and second battery sections or both sections simultaneously. The control circuit is operative to alternately charge the first battery section from an external power source while maintaining the second battery section ready to power the medical devices during an interruption of external power. Then the charging control circuit is operative to charge the second battery section from the external power source while maintaining the first battery section ready to power the medical devices during an interruption of external power. Thus, while each battery section is being charged, the other battery section is in a stand-by mode, such that it serves as a backup power source and takes over operation of the medical devices in the event that the external power source which is providing electrical power to the medical devices fails.

The medical devices preferably comprises a temperature monitoring system connectable to a patient for monitoring a body temperature of the patient and a temperature control system connectable to the patient for controlling the body temperature of the patient. The temperature control system alternatively comprises an extracorporeal blood temperature controller for regulating the blood temperature of the patient in response to the temperature monitoring system.

Alternatively, the temperature control system comprises a temperature controlled water jacket.

The temperature monitoring system preferably comprises either an indwelling rectal temperature probe, an infrared eardrum temperature sensor, an axillary temperature sensor, or an intraesophageal temperature sensor.

Two invasive pressure sensors are preferably provided, so as to facilitate simultaneos measurement of blood pressure and intracranial pressure, for example.

According to one preferred configuration of the present invention, the temperature control system directs temperature controlled air about the patient in response to the temperature monitoring system, so as to maintain the temperature of the patient within a desired range.

The housing is preferably sealable so as to isolate the patient therein from chemical, biological and radiological conditions existing external to the housing. A pressure regulating mechanism disposed within the housing and in electrical communication within the control circuit regulates pressure within the housing so as to facilitate such isolation.

The control circuit preferably comprises an audio/visual device disposed external to the housing and in electrical communication with the control circuit, for displaying patient life support conditions. The audio/visual device preferably displays treatment instructions in response to patient life support conditions.

The control circuit preferably comprises a power regulator for regulating application of electrical power to the medical devices in accordance with an assigned priority status of the medical devices. The controller is preferably operative to modify the assigned priority status of medical devices in response to the patient support conditions in order to preserve the limited battery resource.

The control circuit is preferably operative to simulate a plurality of life support conditions, to monitor an operator's utilization of the medical devices in response to the simulated life support conditions, and to evaluate the effectiveness of the operator's utilization of the medical devices.

The housing preferably comprises a hyperbaric chamber and a hypobaric chamber, preferably formed of a lightweight, durable polymer or composite material.

The control circuit preferably comprises. a medical data reader for receiving medical data from a medical data storage device. The control circuit is operative to regulate operation of the medical devices in response to the received medical data. The medical devices preferably comprise a "dog tag" having medical data stored therein, an identification card having medical data stored therein, or a data storage device implanted beneath a patient's skin.

These, as well as other advantages of the present invention will be more apparent from the following description and drawings. It is understood that changes in the specific structure shown and described may be made within the scope of the claims without departing from the spirit of the invention.

DETAILED DESCRIPTION OF THE PREFERRED EMBODIMENT

The description set forth below in connection with the appended drawings is intended as a description of the presently preferred embodiment of the invention, and is not intended to represent the only form in which the present invention may be constructed or utilized. The description sets forth the functions and the sequence of steps for constructing and operating the invention in connection with the illustrated embodiment. It is to be understood, however, that the same or equivalent functions may be accomplished by different embodiments that are also intended to be encompassed within the spirit and scope of the invention.

Although discussed and illustrated herein as having particular application in battlefield situations, those skilled in the art will appreciate that the transportable life support system of the present invention may be utilized in various different civilian applications, such as emergency rescue and medical evacuation. As such, description and illustration of the present invention for battlefield applications is by way of illustration only, and not by way of limitation.

The transportable life support system of the present invention is illustrated in FIGS. 1–42 which depict a presently preferred embodiment thereof.

Figure 1:
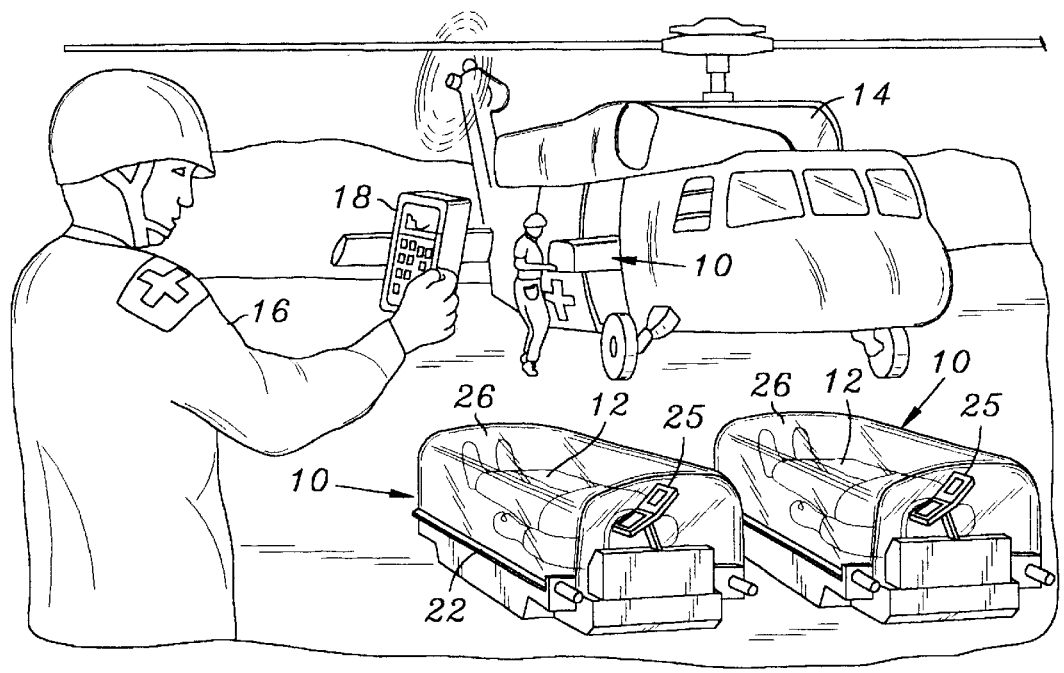
FIG. 1 is a perspective view showing two self-contained transportable life support systems of the present invention containing battlefield casualties, ready for transport upon a helicopter.

Referring now to FIG. 1, two self-contained transportable life support systems 10 of the present invention contain battlefield casualties, i.e., or medical patients 12, who have been readied for transport upon an evacuation vehicle, i.e., helicopter 14. A soldier 16 views a hand held monitoring device 18 via which the medical condition of the medical patients 12 is monitored. The monitoring device 18 provides an indication of the status of each patient 12 contained within a self-contained transportable life support system 10. Optionally, the monitoring device 18 prioritizes patients according to the severity of their medical condition, so as to provide an indication of which medical patients 12 should be evacuated first. Additionally, the monitoring device 18 performs a data logging function, so as to provide a record containing the identification of the medical patient 12, the medical condition thereof, the time of evacuation, and the destination to which the medical patient 12 is to be transported.

Each of the medical patients 12 has a plurality of medical devices in use thereupon, so as to enhance the survivability thereof. The medical devices provide medical monitoring and medical treatment which is intended to extend the golden hour sufficiently to allow transport thereof from the battlefield to a remotely located hospital. Integrated controls and displays 24 minimize the effort required by a medic or other minimally trained personnel in order to provide adequate medical care for the patient.

The self-contained transportable life support system of the present invention is specifically configured to facilitate attachment of a standard NATO stretcher (Stanag) thereto via drop-in attachment wherein stretcher retention members receive and engage the handles of the standard NATO stretcher solely in response to placement of the stretcher thereupon. Thus, in use, the stretcher is merely laid upon the self-contained transportable life support system to facilitate automatic attachment thereto. Once the stretcher is so attached, the desired medical monitoring devices and medical treatment devices are utilized to provide the desired medical care for the medical patient.

Figure 2:
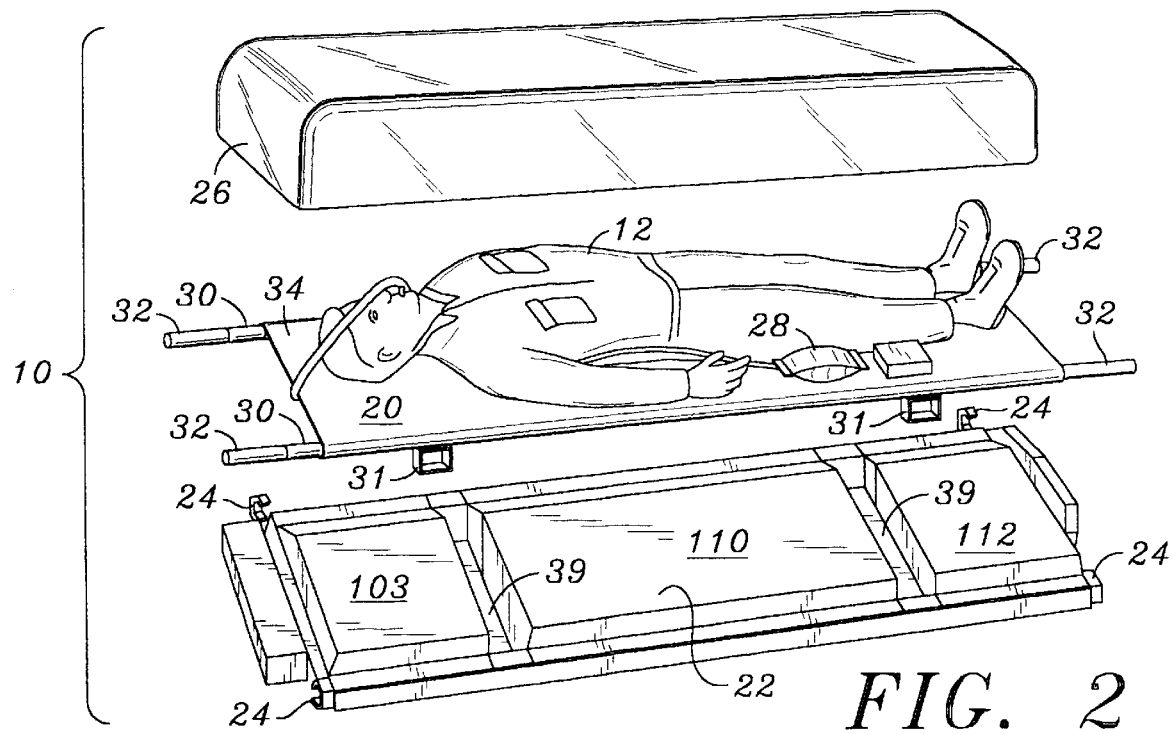
FIG. 2 is a perspective view of the self-contained transportable life support system of FIG. 1 showing the upper housing section and the medical patient exploded away from the housing thereof.

Referring now to FIG. 2, the medical patient 12 is disposed upon a standard NATO stretcher 20. The stretcher attaches to the lower housing section 22 of the self-contained transportable life support system via four stretcher retention members 24 which automatically attach the stretcher 20 thereto when the stretcher is placed upon the lower housing section 22.

An optional upper housing section 26 forms a canopy over the medical patient 12, and cooperates with the lower housing section 22 so as to define a housing which provides isolation for the medical patient 12. A transparent window 27 is preferably provided to facilitate viewing of the medical patient 12. The upper housing section 26 is optionally pressurizable so as to enhance such isolation. Positive pressurization, i.e., pressure above ambient, of the upper housing section 26 is provided to isolate the medical patient 12 from care givers and/or the environment. Such positive pressurization of the upper housing section 26 causes air to leak therefrom. Thus, air is prevented from leaking into the upper housing section 26. Thus, biological, chemical, and radiological isolation may be provided for the medical patient 12 by filtering air prior to pressurizing the upper housing section 26 with it.

The upper housing section 26 may also be provided with a negative pressure, i.e., a pressure below ambient, such that air leaks from the environment into the container, so as to provide for isolation of the care givers from the medical patient. In this instance, air drawn into the upper housing section is filtered prior to being exhausted therefrom.

The upper housing section 26 is preferably formed of a lightweight, rigid, polymer or composite material. Alternatively, the upper housing section 26 may be comprised of a fabric, having support straps or hoops for maintaining the desired shape thereof. In any event, the upper housing section 26 is preferably configured so as to provide a substantially air tight seal to the lower housing section 22, so as to minimize air leakage either there into or therefrom, thus improving the isolation capability. However, it would be recognized that an absolutely air tight seal is not necessary since the upper housing section 26 can be pressurized as discussed above, so as to provide the desired isolation.

The medical devices are preferably integrated into the lower housing section 22 in a manner which minimizes the weight and volume thereof. Weight is minimized by eliminating components common to a plurality of the medical devices, such as the power supplies therefor. Volume is minimized by such elimination of common components and also by packaging the medical devices more economically than is possible with off-the-shelf devices. Further, such integration of the medical devices provides for more efficient power consumption since the devices are powered from a common source and are under common control, so as to facilitate more efficient operation thereof.

According to the preferred embodiment of the present invention, a fluid infuser 28, which is stored within a storage compartment of the lower housing section 22 prior to use, may be laid upon the stretcher to provide fluid infusion for the medical patient 12.

The stretcher 20 comprises two poles 30, each pole having two handles 32, one handle being formed upon either end thereof. Canvas 34 stretchers between the two poles 30.

Two feet 31 depend downwardly from each pole 30. The lower housing section 22 is configured to receive the feet 31 within channels 39 formed within the lower housing section 22, so as to prevent longitudinal movement of the stretcher 20 with respect to the lower housing section 22. The stretcher retention members 24 prevent lateral, as well as vertical, movement of the stretcher 20 relative to the lower housing section 22.

Figure 3:
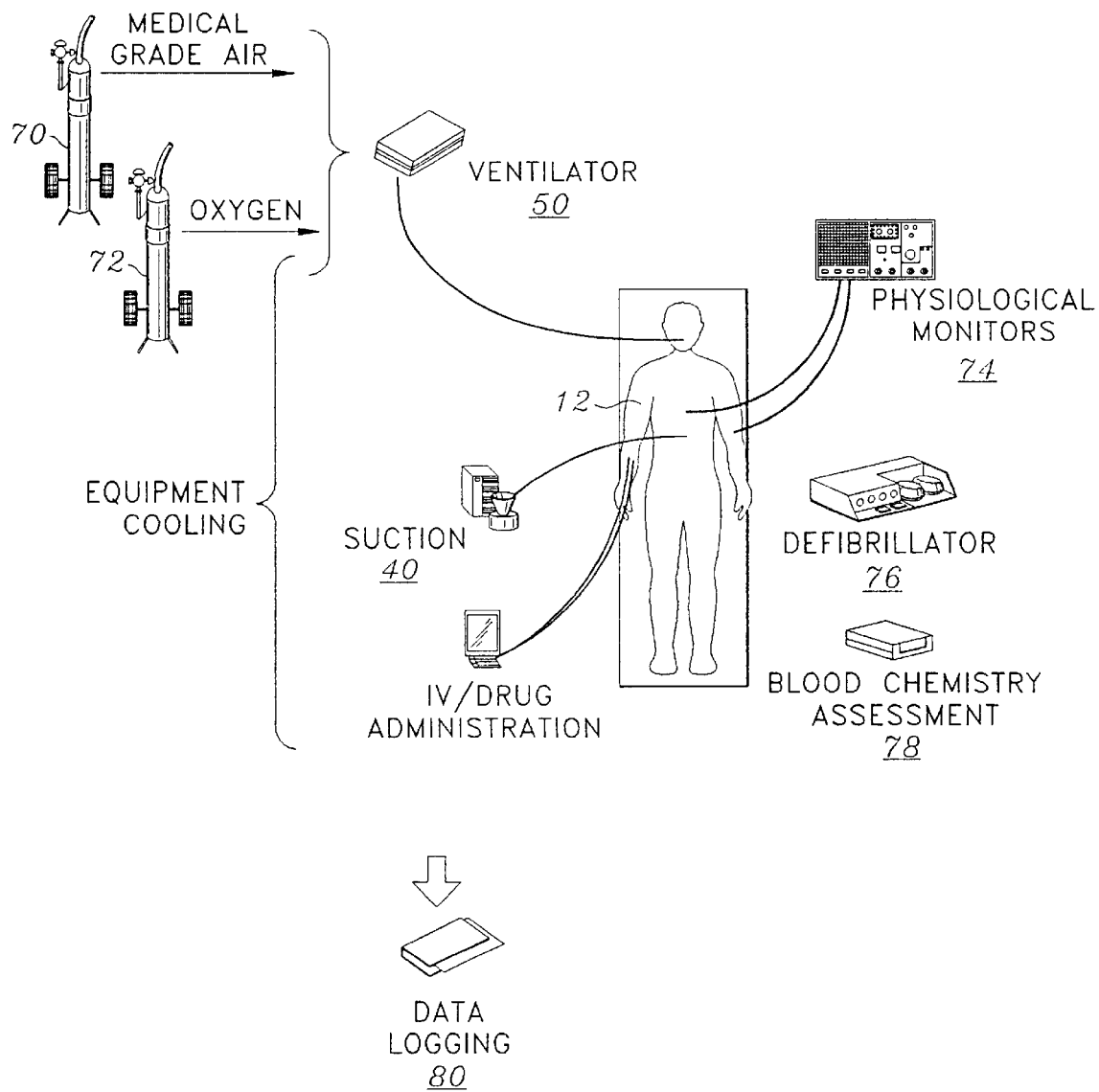
FIG. 3 is a schematic view of a patient disposed upon the lower housing section of the present invention and having a plurality of medical devices attached thereto.

Referring now to FIG. 3, the medical monitoring devices and medical treatment devices provided to a patient disposed upon the self-contained transportable life support system of the present invention are shown schematically. Either medical grade air, i.e., oxygen enriched air 70 or oxygen 72, is provided via the ventilator 50 to the patient 12. Such oxygen enriched air or oxygen may be provided to the ventilator either via the onboard oxygen generator system, pressurized oxygen bottles, or via an external source thereof.

The suction unit 44 may be used to provide suction to maintain a clear airway or, alternatively, may be utilized to provide suction to wounds, as desired.

Physiological monitors 74 monitor such medical parameters as blood pressure, heart rate, ECG, etc. Defibrillator 76 may be used when fibrillation is indicated by the physiological monitor 74 or by the defibrillator's automated assessment of patient status.

A blood chemistry assessor 78 provides blood chemistry assessment. Data logging facilitates review of the patient's monitored medical parameters and treatment.

It is important to remember that the medical devices shown in FIG. 3 are actually integrated into the lower housing section 22 of the present invention, and are not off-the-shelf, separate discreet units, as shown. The medical devices are illustrated as separate, discreet, off-the-shelf units for clarity only, and so as to give a general indication of the types of medical devices integrated into the present invention.

Figure 4:
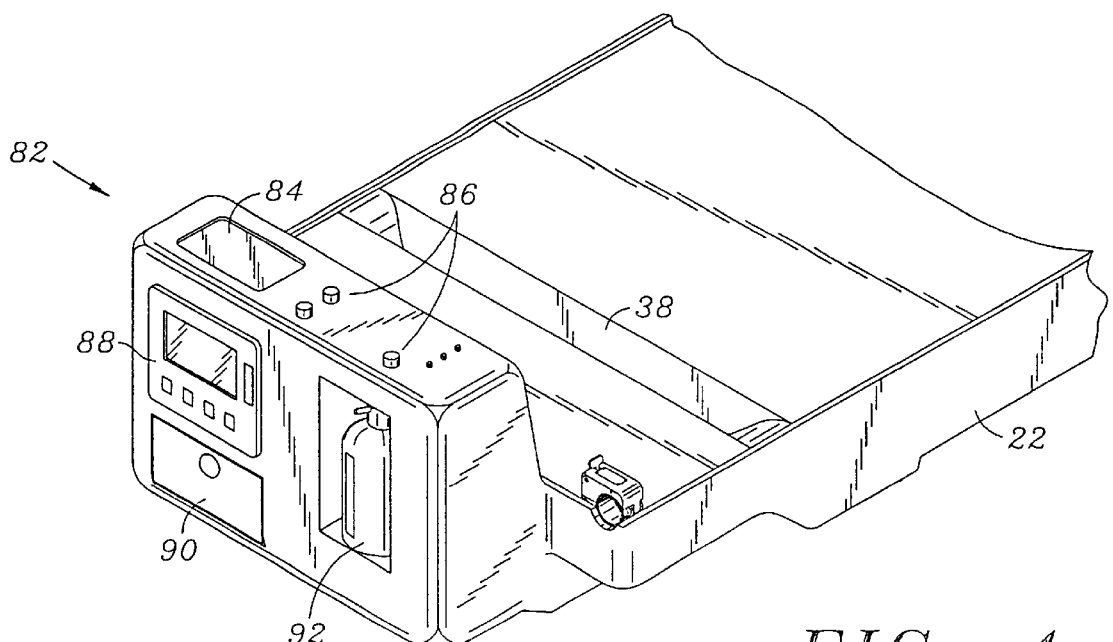
FIG. 4 is a perspective view of one preferred configuration of the head end of the self-contained transportable life support system of the present invention.
Figure 5:
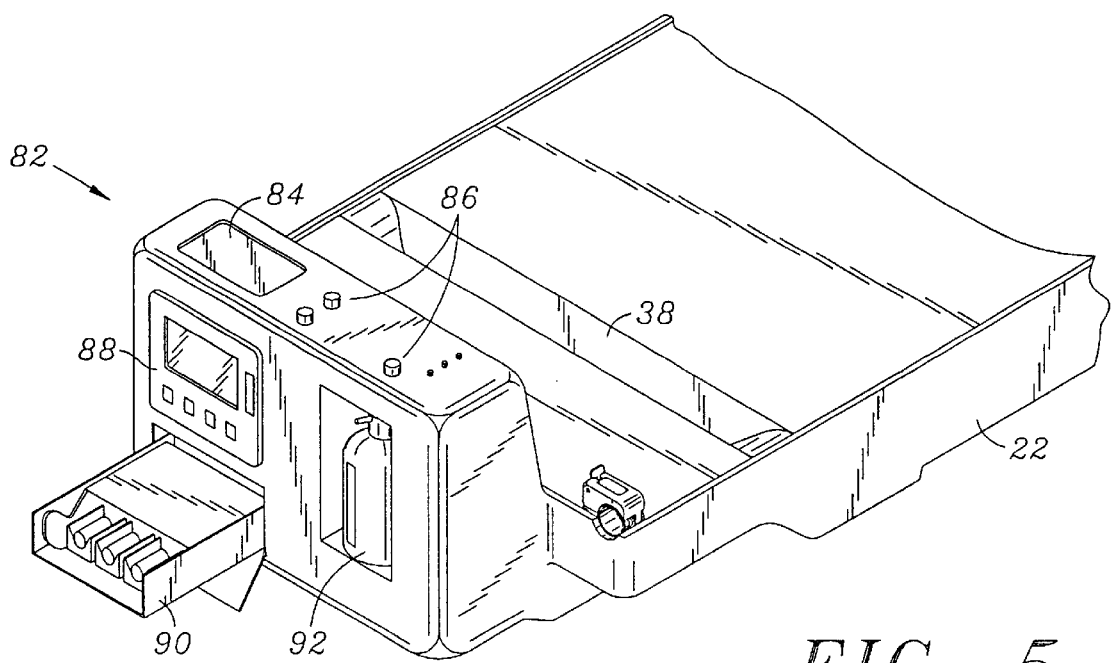
FIG. 5 is a perspective view of the head end of the self-contained transportable life support system of FIG. 4 showing the infusion device thereof deployed for use.

Referring now to FIGS. 4 and 5, one preferred configuration of the head end of the lower housing section 22 is shown. According to this preferred configuration, the head end 26 of the lower housing section 22 comprises a visual display 84 for displaying information regarding operation of the ventilator. Controls 86 for controlling operation of the ventilator allow a care giver to vary the respiration rate and tidal volume.

Physiological monitoring is facilitated via monitor 88 which facilitates display of blood pressure, temperature, ECG, etc. and also provides for the control of the medical monitoring devices which monitor blood pressure, temperature, ECG, etc. The controls of the physiological monitor 88 also allow the care giver to preset alarm limits for physiological parameters such as blood pressure, temperature, ECG, etc. When such an alarm is exceeded, an audible alarm sounds.

Intravenous drug administration is facilitated via infusion pump 90, which may comprise a high volume infusion pump. According to the preferred embodiment of the present invention, three separate fluid inputs are accepted by the infusion pump 90 and three separate metered outputs are provided thereby. The three outputs can be joined together into a single output, in any combination desired.

Suction reservoir 92 facilitates the collection of fluids collected by one or more suction device(s).

Figure 6:
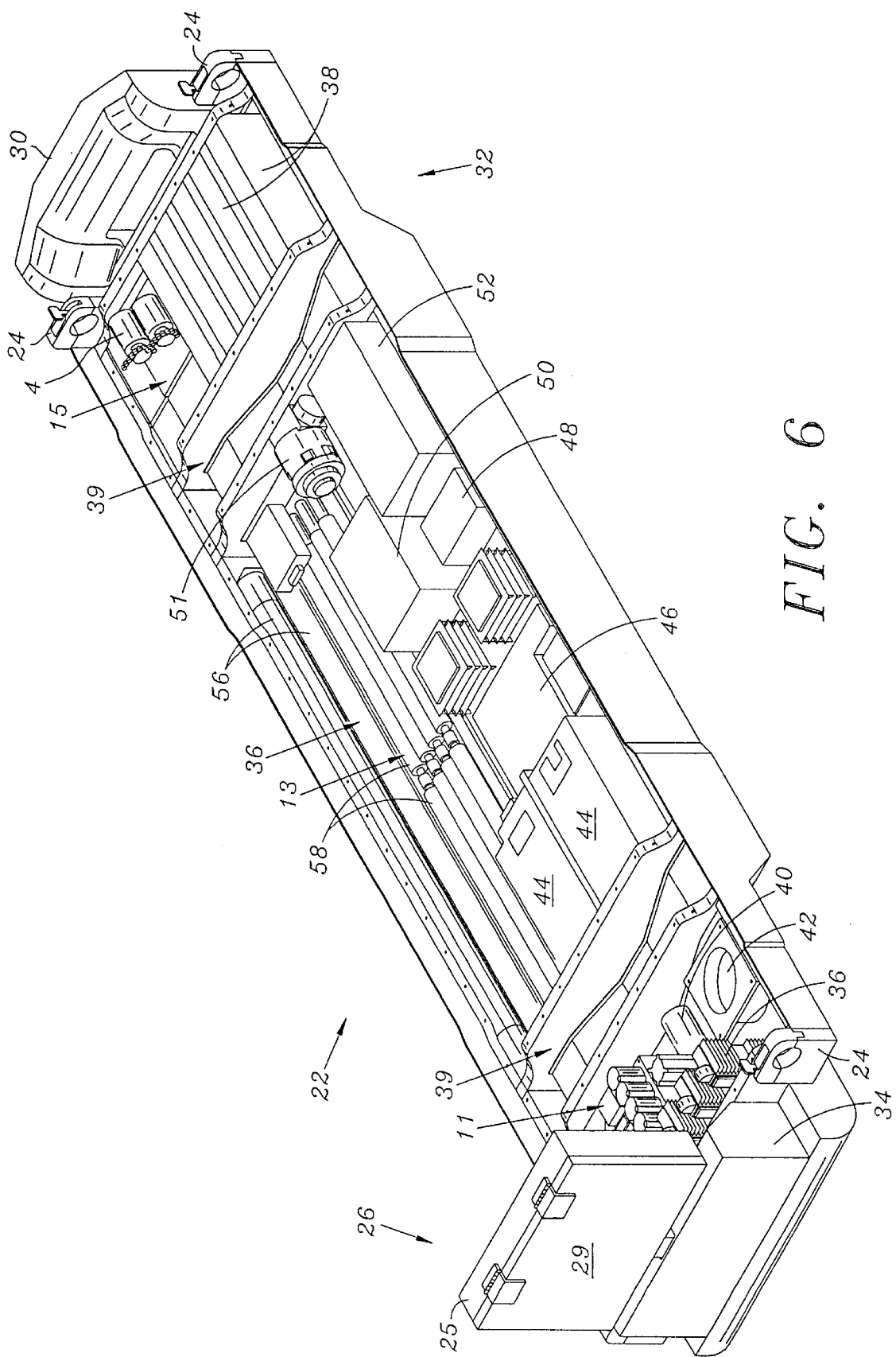
FIG. 6 is a perspective view of the open lower housing section of the present invention, showing the medical devices and system components contained therein.
Figure 7:
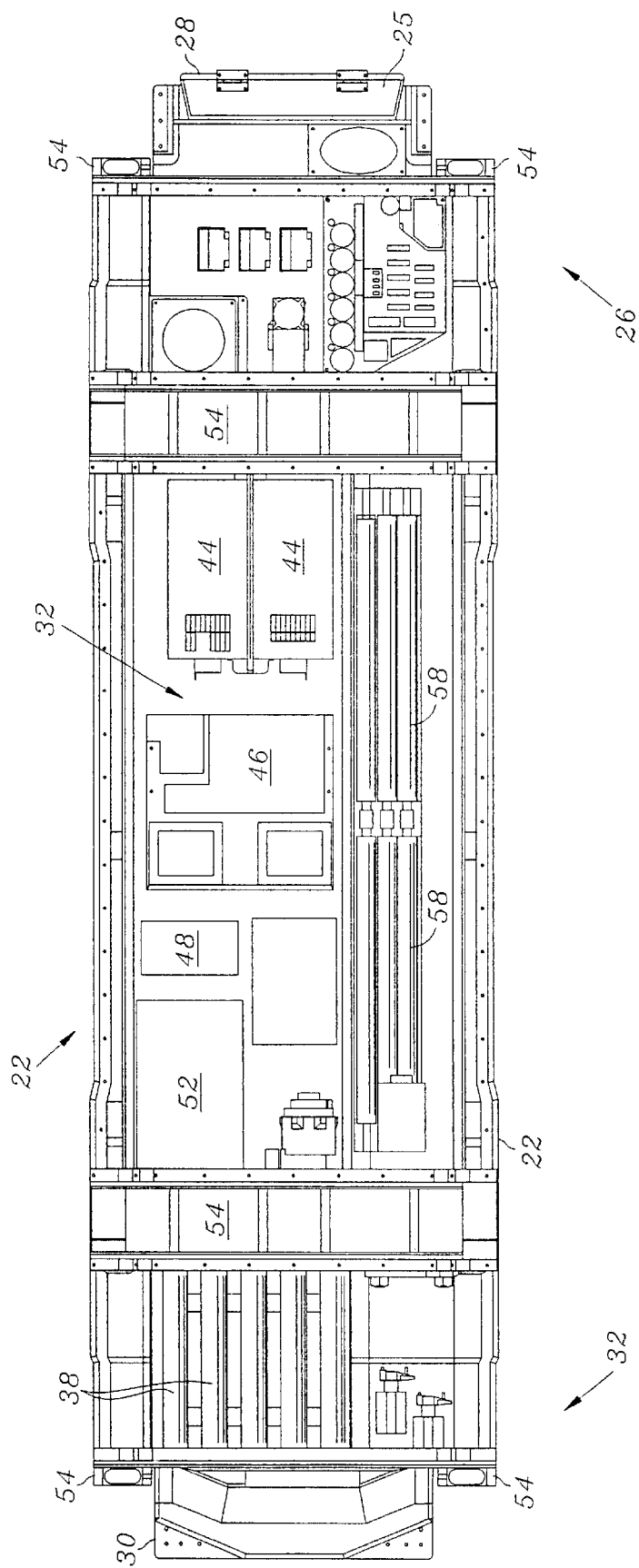
FIG. 7 is a top plan view of the open lower housing section of FIG. 6.

Referring now to FIGS. 6 and 7, according to the preferred embodiment of the present invention, the lower housing section 22 contains the medical monitoring devices and medical treatment devices necessary to prolong the golden hour sufficiently to enhance a patient's survivability during extended transport to a remote medical facility. The lower housing section 22 preferably comprises a lightweight polymer or composite structure configured to contain the medical monitoring devices and medical treatment devices. The medical devices are integrated with the lower housing section 22 in a manner which reduces the volume thereof. Such integration also facilitates construction of the present invention in a manner which allows it to be used in military vehicles having standard NATO stretcher mounts, wherein the size of equipment received within the standard NATO stretcher mounts is strictly constrained in order to avoid interference with nearby stretchers and/or other mounted objects, i.e., battlefield casualties on NATO stretchers. A monitor or touch screen display 25 is formed at the head end 26 of the lower housing section 22. The touch screen display 26 preferably comprises a closable cover 29 to provide protection thereto. A second monitor and/or touch screen may be formed upon the inner surface of the cover 29, if desired.

An environmental control system fan assembly 30 is provided at the foot end 32 of the lower housing section 22 and comprises at least one fan for drawing air into the upper housing section 26 and filters for filtering the air. In a similar manner, equipment fan assembly 34 contains at least one fan for drawing air into the equipment compartment 36 of the lower housing section 22 and filters for filtering the air drawn into.

According to the preferred embodiment of the present invention, the filters of the system fan assembly 34 provide chemical, biological, and radiological filtering, so as to provide isolation of the medical patient 12 disposed within the upper housing section 26. The filters of the fan assembly 34 provide particulate filtering, so as to inhibit contamination of the medical devices contained within the lower housing section 22. The air path of the upper housing section 26 and the lower housing section 22 are separate and isolated from one another, such that the air in each path is not commingled. When the self-contained transportable life support system of the present invention is first powered up, the equipment fans run for a short period of time prior to the application of electrical power to the medical devices, such that any oxygen and/or hydrogen which is built up in the lower housing section 22 is exhausted prior to fully powering the system up, so as to mitigate any explosion or fire hazard which could be caused thereby.

Power supply circuitry 36 receives electrical power from battery packs 38 or power converters 44 to provide electrical power to the medical devices. The battery packs 38 define first and second battery sections which cooperate to provide electrical power to the various medical devices of the self-contained transportable life support system. Preferably, a controller is configured to facilitate charging of one of the battery sections while the other of the battery sections is providing power to the self-contained transportable life support system, and then the roles of the two battery sections switch such that the second battery section provides electrical power to the self-contained transportable life support system while the first battery section is charging.

A suction pump 40 may be utilized to provide suction to maintain clearance of the airway, as well as to remove blood and/or other body fluids from wounds, etc. Fluids removed by the suction pump 40 may either be dumped overboard or deposited within suction bottle 42 for later analysis.

Power converters 44 convert electrical power from a building, transport vehicle, etc. into power which is usable for running the medical devices of the self-contained transportable life support system, as well as power for charging the batteries 38 thereof.

Control circuitry 46 facilitates control of the medical devices of the present invention such that the medical treatment devices thereof are responsive to the medical monitoring devices thereof and such that the medical treatment devices cooperate to provide beneficial medical treatment to the patient. The control circuitry 46 is responsive to operator input via the touch screen display 26, a separate hand-held monitoring device, as well as remote control instructions from medical personnel at a remote medical facility.

Ventilator pneumatic controller 48 controls the ventilator compressor 50 so as to provide ventilation for the medical patient. The closed-loop ventilator accepts oxygen from either an external source or from the onboard oxygen generator/pressurized oxygen bottle/enrichment system. The ventilator can also be utilized to administer anesthesia.

Oxygen generator 52 provides oxygen or oxygen enriched air which may be provided to the patient through the ventilator.

Channels 39 are configured to receive the feet 31 of the stretcher 20, so as to prevent longitudinal and lateral movement of the stretcher relative to the lower housing section 22.

Stretcher retention members 24 facilitate drop-in attachment of the stretcher to the lower housing section 22 such that the handles 30 of the stretcher need merely be placed upon the stretcher retention members 24, which then open in response to the weight of the stretcher and automatically close about the handles thereof so as to provide secure attachment of the stretcher to the lower housing section 22. Alternatively, the stretcher retention members 24 may be opened manually and then closed in response to lowering of the stretcher handles 30 thereupon.

The stretcher retention members 24 prevent lateral and vertical movement of the stretcher relative to the lower housing section 22. Oxygen reservoirs 56 temporarily store oxygen generated by the oxygen generator 52. The use of an onboard oxygen generator 52 eliminates the need to carry heavy and bulky bottled or liquid oxygen. The onboard oxygen generator preferably utilizes facilitative transport membrane to provide oxygen or oxygen enriched air to the medical patient.

Heat exchangers 58 facilitate temperature control of the patient by providing temperature controlled air or water thereto. An environmental control system preferably comprises a vapor compression cooler and a heater and an air temperature controller. According to the preferred embodiment of the present invention, the air temperature controller can both heat and cool air which is provided to the upper housing section 26 for breathing. Additionally, the environmental control system comprises an air filter system for filtering breathing air supply to the upper housing section. The breathing air is filtered so as to remove biological, chemical, and radiological contamination in a manner similar to that of a contemporary gas mask.

Figure 8:
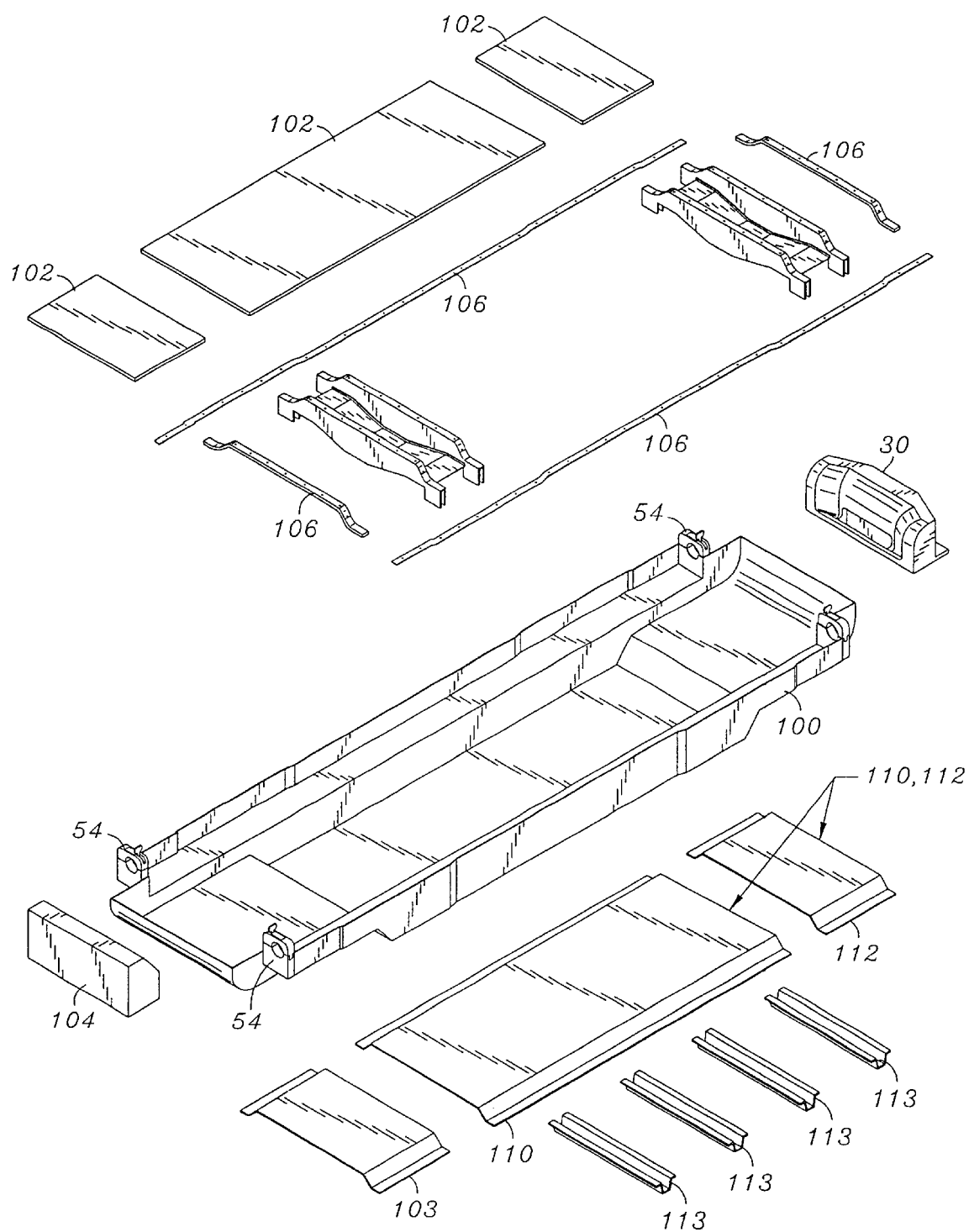
FIG. 8 is an exploded view of the lower housing section.

Referring now to FIG. 8, the lower housing section 22 generally comprises a sled 100, padding 102 is disposed upon the sled 100 such that the patient is supported thereby when placed upon the lower housing section 22. The lower housing section 22 is configured such that the canvas 34 of the stretcher 20 rests upon the pads 102, such that the pads 102 receive the full weight of the patient.

The filter housing 104 houses the fan and filter assemblies which provide cooling into the medical devices, as discussed above. Access door support stiffeners 106 provide structural rigidity to the access doors. Forward access door 108 provides access to the head compartment 11 of the lower housing section 22, center access door 110 provides access to the center compartment 13 of the lower housing section 22 and, aft access door 112 provides access to the foot compartment of the lower housing section 22. Center access door stiffeners attach to the center access door 113 to provide structural rigidity thereto. Environmental control system equipment exhaust housing 30 contains the environmental control system fans and filters for providing filtered air to the upper housing section 26, as described above.

Figure 9:
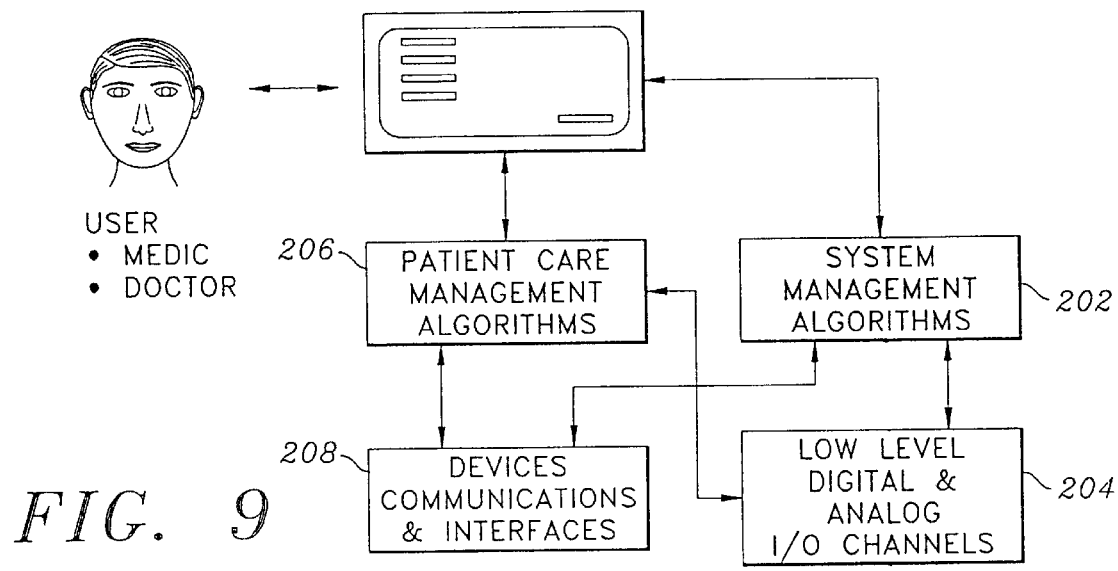
FIG. 9 is a block diagram of the communications, controls, and displays graphical interface.

Referring now to FIG. 9, the display 24 is controlled via system management algorithms 202 which cooperate with low level digital and analog input/output channels 204. The low level digital and analog input/output channels cooperate with patient care management algorithms 206, the status of which are displayed upon display 24. Device communications and interfaces 208 cooperate with patient care management algorithms 206 and system management algorithms 202.

Figure 10:
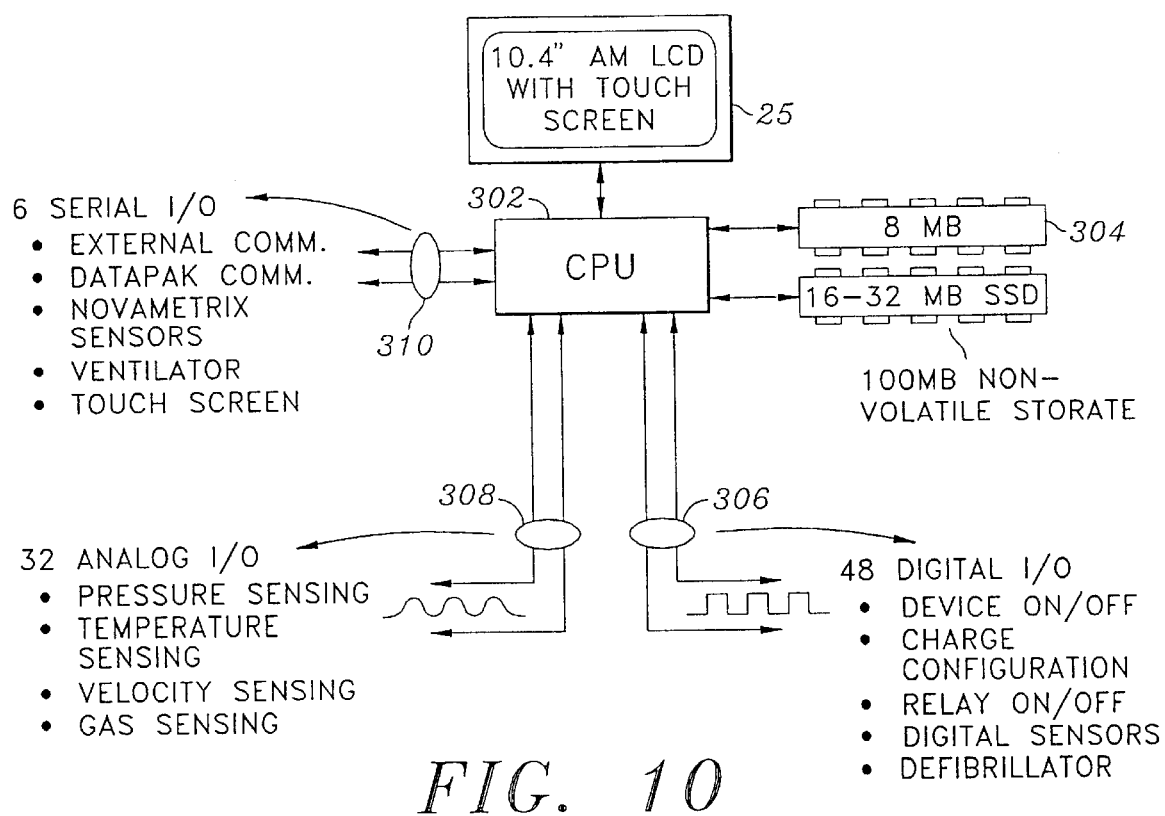
FIG. 10 is a schematic representation of the communication, controls, and displays hardware architecture.

Referring now to FIG. 10, the display 25 is preferably under the control of a CPU 302 having at least 8 megabytes of RAM 304 and at least 100 megabytes of hard disk or equivalent non-volatile storage 305.

According to the preferred embodiment of the present invention, 48 channels of digital input/output 306 are provided. The input/output channels provide information regarding device status, i.e., on/off, charge configuration, relay on/off, and digital sensors. The digital input/output 306 also facilitates control of the defibrillator. Thirty-two channels of analog input/output 308 provide pressure sensing, temperature sensing, velocity sensing, gas sensing, etc. Six serial input/output channels provide external communications, data storage device communications, physiological sensors, ventilator, and touch screen.

Figure 11:
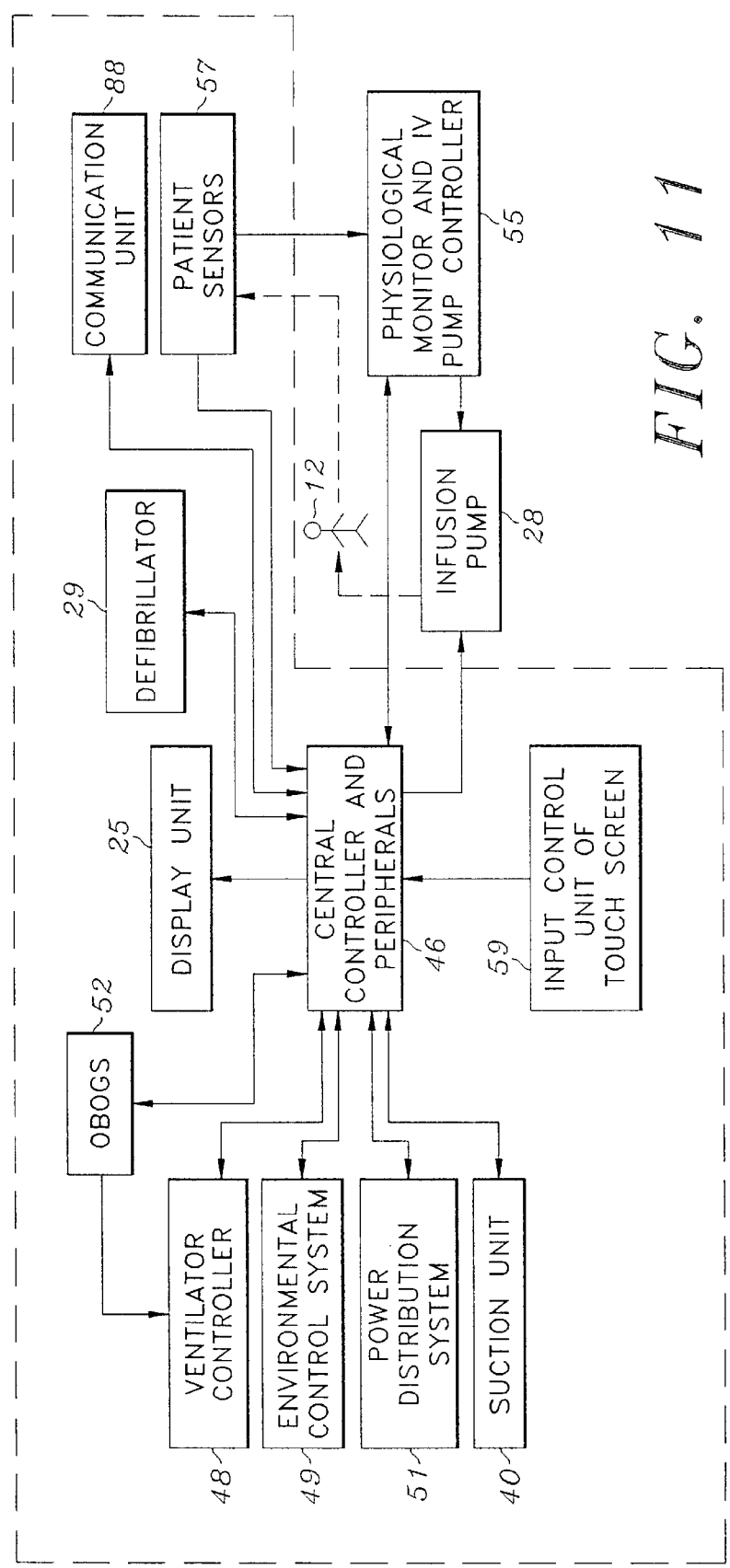
FIG. 11 is a block diagram of the communications, controls, and displays interface.

Referring now to FIG. 11, the control circuitry 46 of the central controller controls the operation of the onboard oxygen generator system 52, the ventilator controller 48, the environmental control system 49, the power distribution system 51, the suction unit 40, the display 25, the defibrillator 29, the infusion pump 28, the physiological monitor and IV pump controller 55, the patient sensors 57, and the communications unit 88.

Figure 12:
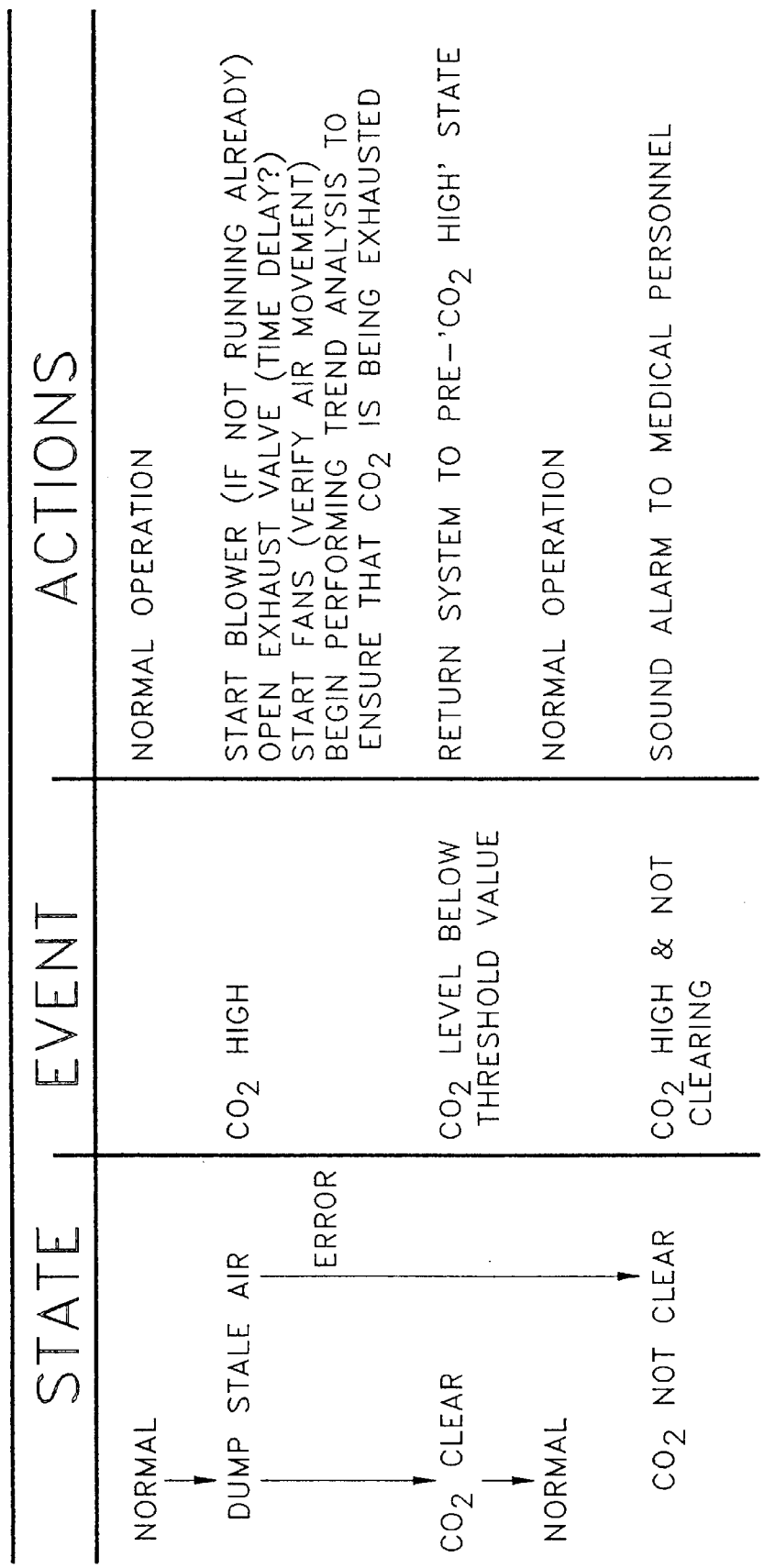
FIG. 12 is a sample algorithm for the controls and displays.

Referring now to FIG. 12, a sample controls and displays algorithm is shown. According to the sample algorithm, when a high $CO_2$ level is sensed, then stale air is dumped from the upper housing section 26 by starting the fan 154, if it is not already running. The exhaust valve is opened, with a time delay, if desired. Air movement is preferably verified.

Trend analysis is then initiated upon the patient to verify that $CO_2$ is being properly exhausted. When the housing $CO_2$ level is at an acceptable level, then the system returns to the normal operation state. If the $CO_2$ cannot be cleared, then an alarm is sounded to alert the care giver.

Figure 13:
FIG. 13 is a symbol utilized to indicate that the defibrillator is off.
Figure 14:
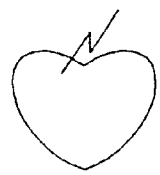
FIG. 14 is a symbol utilized to indicate that the defibrillator is on and charging.

FIG. 13 shows the preferred symbol utilized to indicate that the defibrillator is off and FIG. 14 shows the preferred symbol used to indicate that the defibrillator is being charged. Flashing of the symbol of FIG. 14 indicates that the defibrillator is ready to discharge. Pressing the flashing symbol of FIG. 14 on the touch screen 25 causes the defibrillator to discharge.

Figure 15:
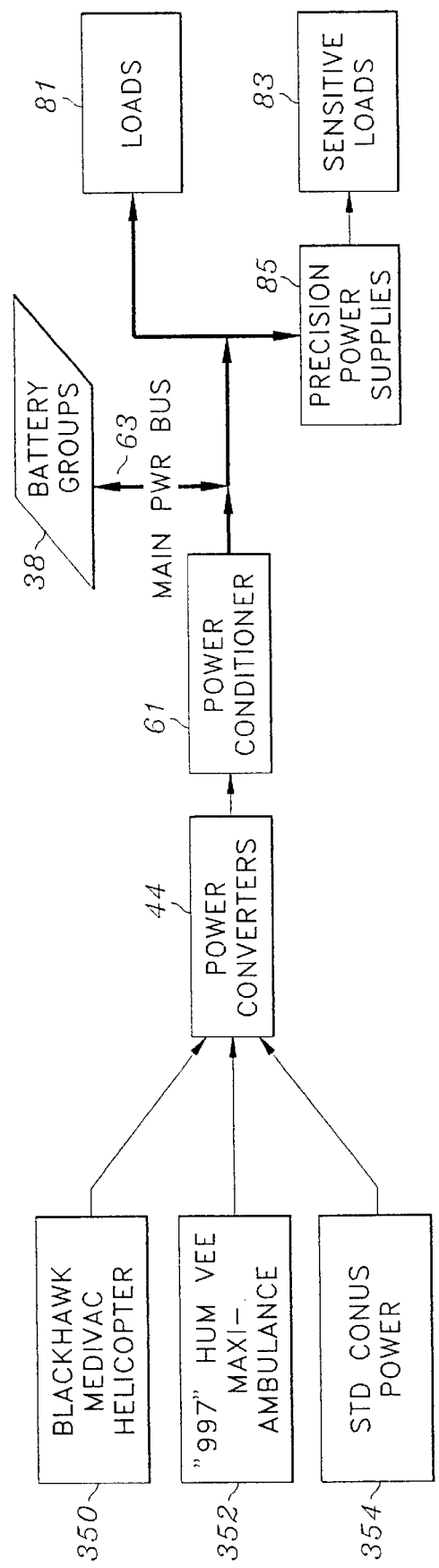
FIG. 15 is a functional block diagram of the power management system.

Referring now to FIG. 15, power converters 44 are configured to accept electrical power from the Blackhawk Medevac helicopter 350, the HumVee 352, as well as STD CONUS POWER 354. Power conditioner 61 assures that the power is compatible with the main bus 63 of the self-contained transportable life support system of the present invention. The batteries 38 receive power from the main bus 63 to facilitate charging thereof and provide power to the main bus 63 when being utilized for the operation of the self-contained transportable life support system. Nonnoise sensitive lodes 81 receive power directly from the bus 63 while sensitive lodes 83 receive power via precision power supplies 85.

Figure 16:
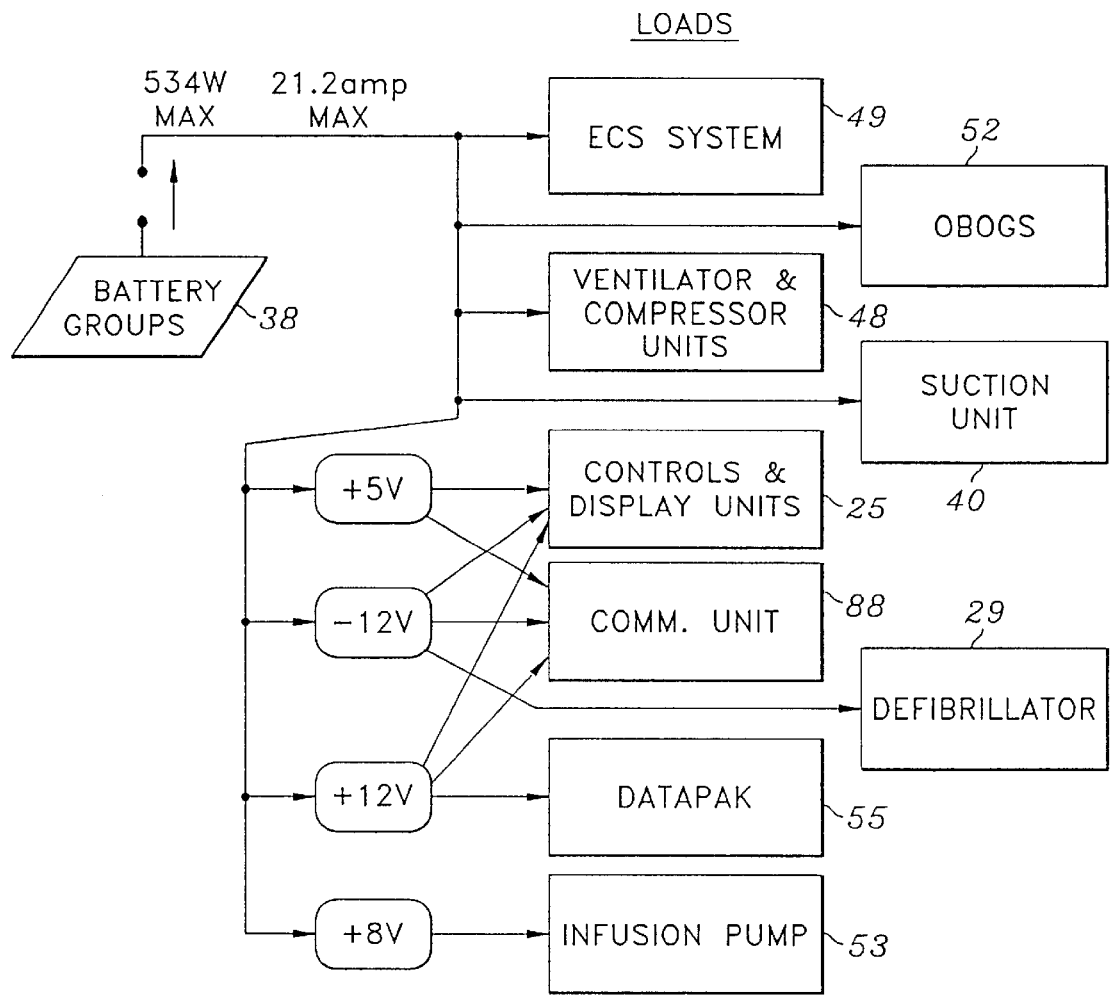
FIG. 16 is a block diagram showing the power management system in the autonomous mode.
Figure 17:
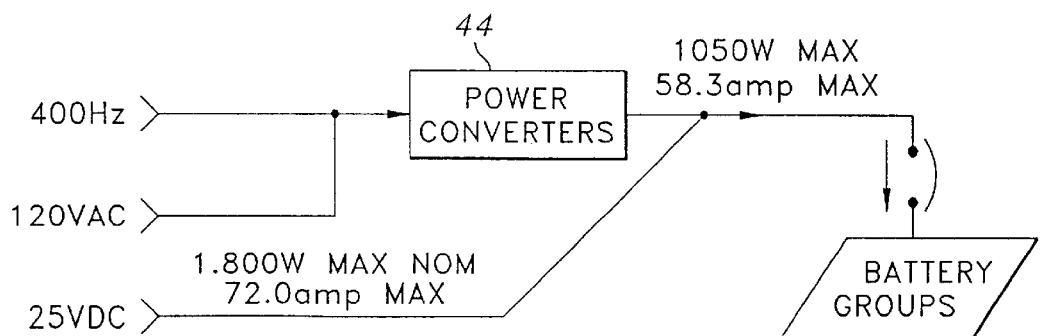
FIG. 17 is a block diagram showing the power management system in the recharge mode.

Referring now to FIGS. 15-19, the operational modes of the power management system are illustrated. With particular reference to FIG. 16, in the autonomous mode of operation, the batteries 38 provide electrical power to the environmental control system 49, the onboard oxygen generator system 52, the ventilator and compressor units 48, the suction unit 40, the controls and displays unit 25, the communication unit 88, the defibrillator 29, the data storage device 55 (data storage device for maintaining a log of medical parameters and medical treatment provided), and the infusion pump 53. With particular reference to FIG. 17, in the recharge mode, the power converters 44 provide electrical power to the battery groups 38.

Figure 18:
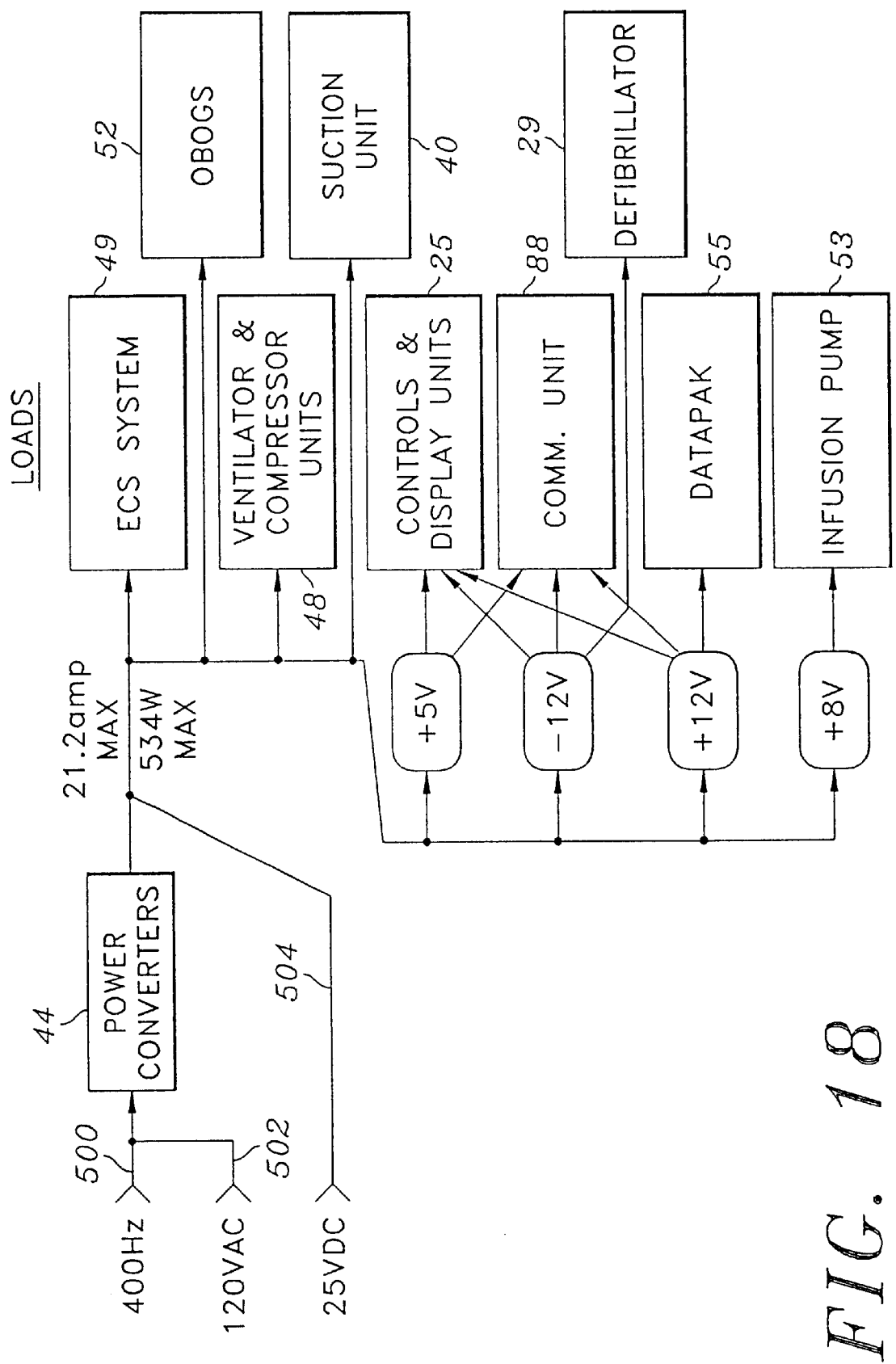
FIG. 18 is a block diagram showing the power management system in the auxiliary power mode.

With particular reference to FIG. 18, in the auxiliary power mode, electrical power is provided by an outside source. Such electrical power may comprise 400 hertz 500, 120 VAC 502 and/or 25 VDC 504. The power converter 44 receives, the 400 hertz 500 and/or the 120 VAC 502-and provides an output at 21.2 amps maximum, 534 watts maximum to the ECS system 49, onboard oxygen generator system 52, ventilator and compressor unit 48, suction unit 40, control and display unit 25, communications unit 88, defibrillator 29, data storage device 55, and infusion pump 53.

Figure 19:
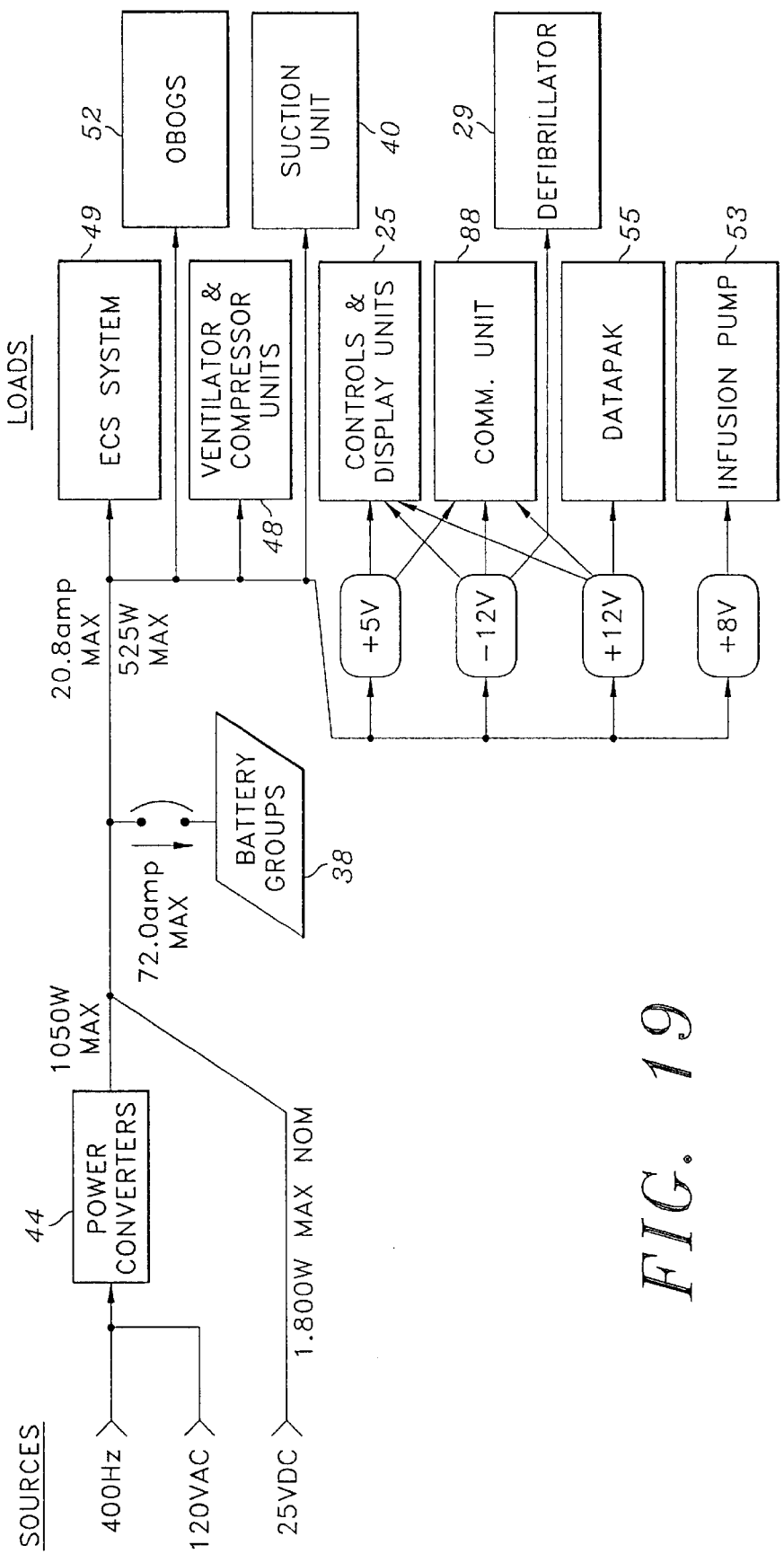
FIG. 19 is a block diagram showing the power management system in the auxiliary power with recharge mode.

With particular reference to FIG. 19, during the auxiliary power with recharge mode, the battery power groups 38 are charged while providing operation similar to that in the auxiliary power mode of FIG. 18.

Figure 20:
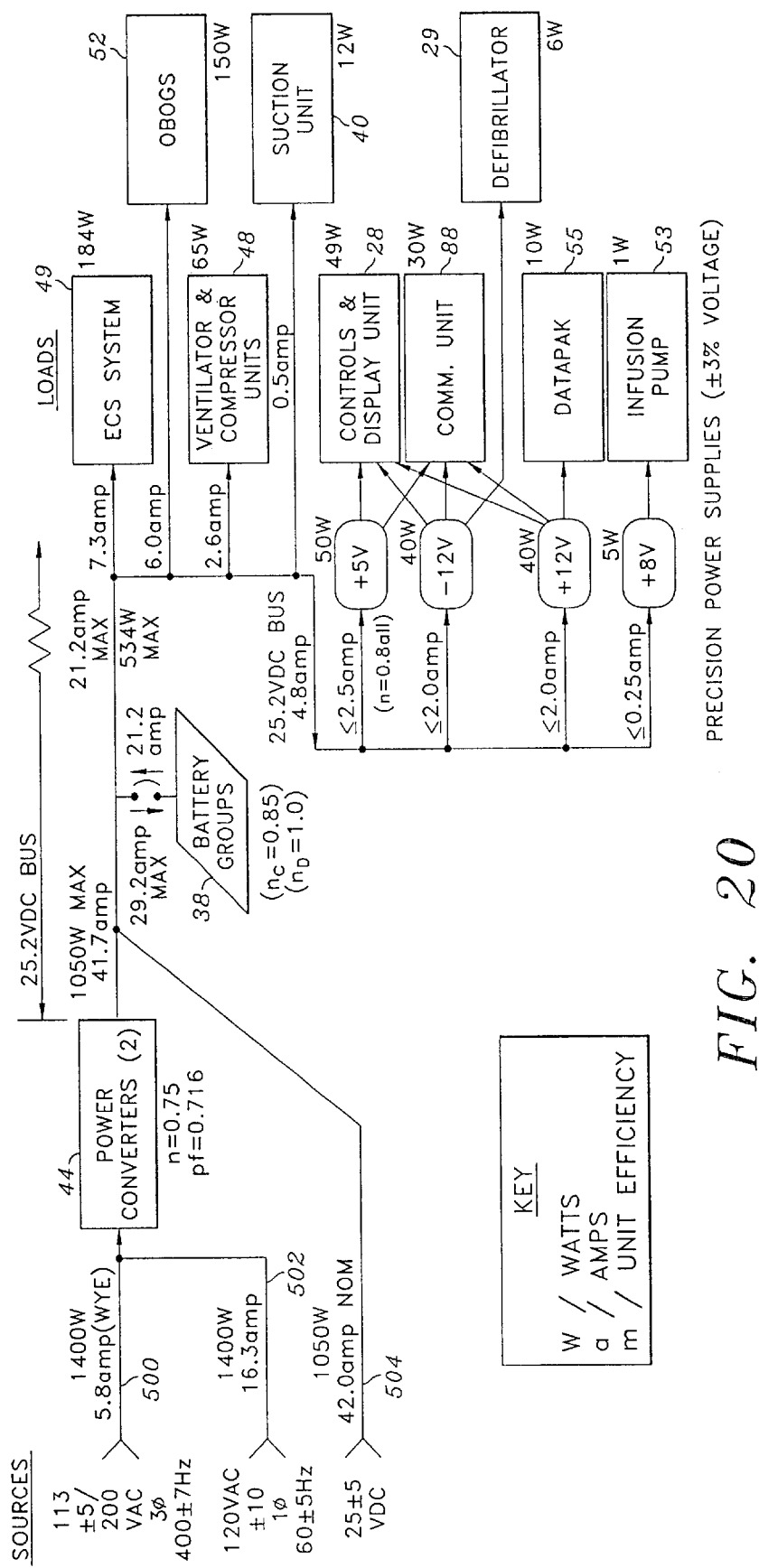
FIG. 20 is a block diagram showing the power management system in further detail.

Referring now to FIG. 20, an overall schematic representation of the power management system is provided. This schematic representation shows the various relationships of the power sources, i.e., the 400 hertz 500, 120 VAC 502 and the 25 VDC 504. The battery power group 38 may be charged, as shown in FIG. 19. Powers provided to the various loads as shown in FIGS. 16, 18 and 19.

Figure 21:
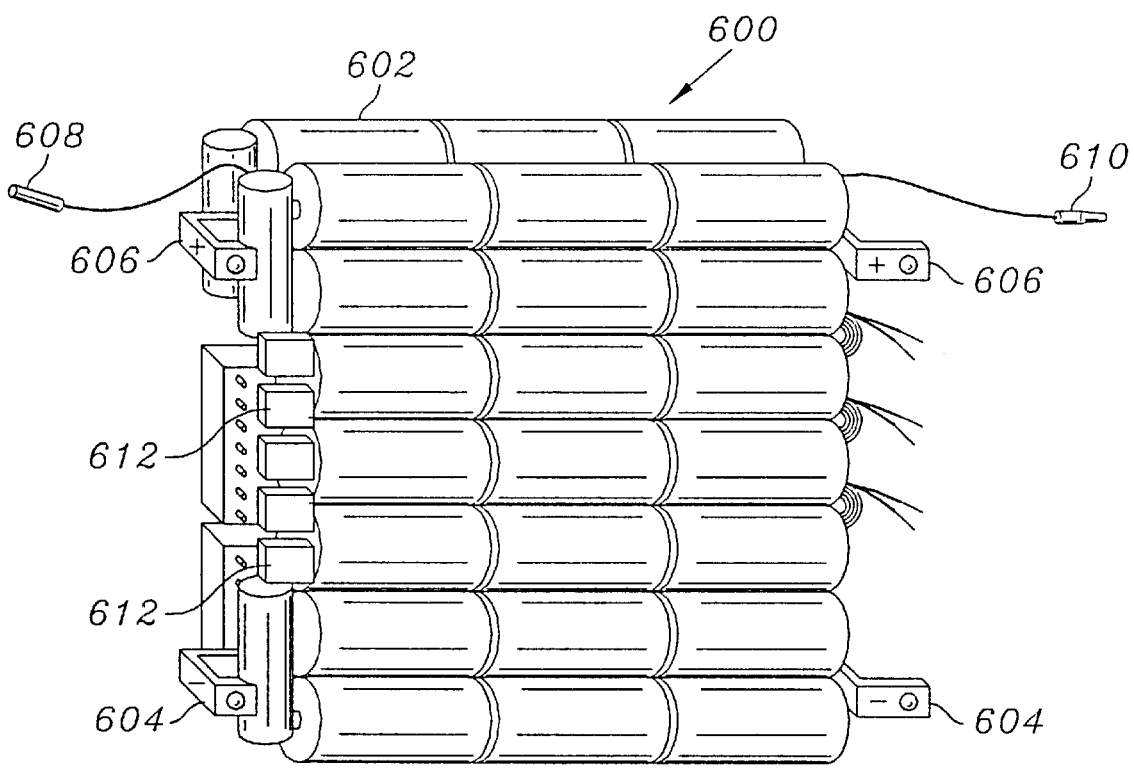
FIG. 21 is a perspective view of the battery pack system.

Referring now to FIG. 21, each battery section is preferably comprised of a plurality of battery packs 600, each battery pack comprising a plurality of individual batteries 602 which are connectable to the electrical system of the self-contained transportable life support system via negative bus bar support 604 and positive bus bar support 606. Thus, the negative bus bar support 604 and the positive bus bar support 606 provide for both the electrical connection of the battery pack, as well as the mechanical mounting thereof. Negative relay control 608 and positive relay control 610 facilitate selective reconfiguration of a particular battery pack from the remaining packs in the event of failure thereof protection diodes 612 isolate reconfigured battery cells and prevent overcharging of the battery 602. Thus, in the event that a particular cell fails to operate properly, the battery pack containing that cell is automatically disconnected from the remaining battery packs, so as to facilitate the maintenance of desired power to the medical devices. Each battery pack preferably comprises 42 individual cells.

Figure 22:
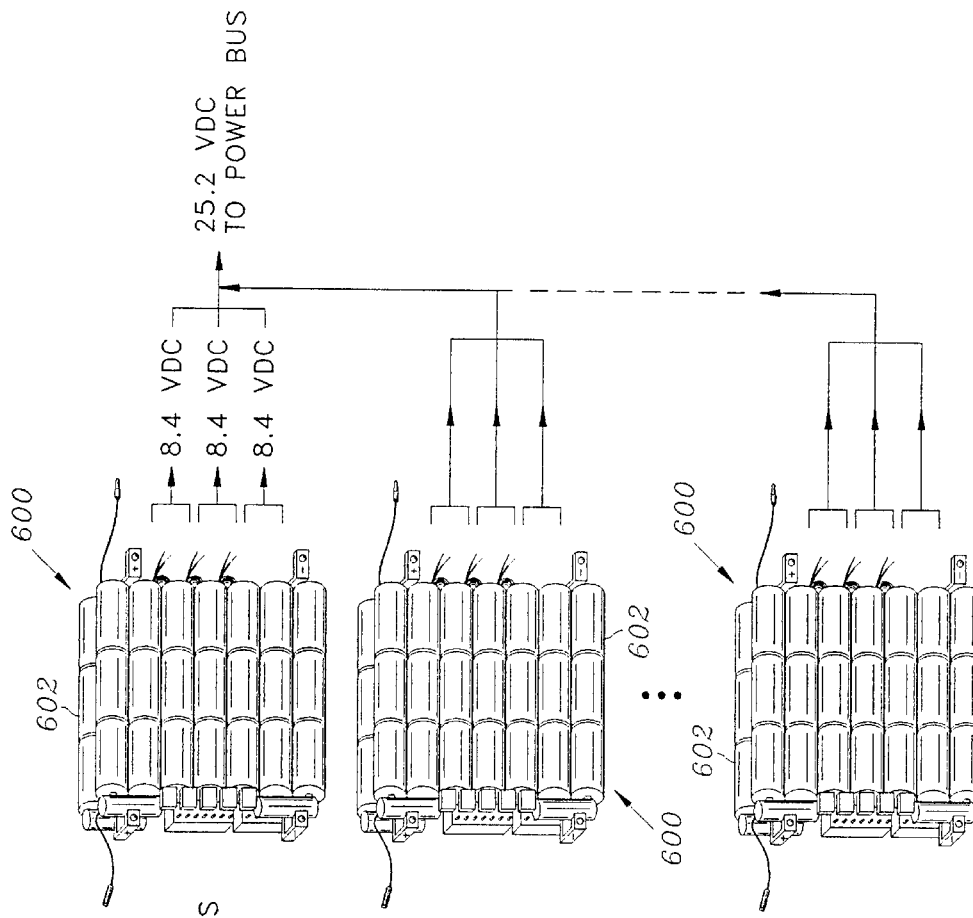
FIG. 22 is a schematic illustration of the battery segment.

Referring now to FIG. 22, a plurality of battery acks such as those shown in FIG. 21 are configured so as o provide approximately 25.2 volts DC to the power bus.

Figure 23:
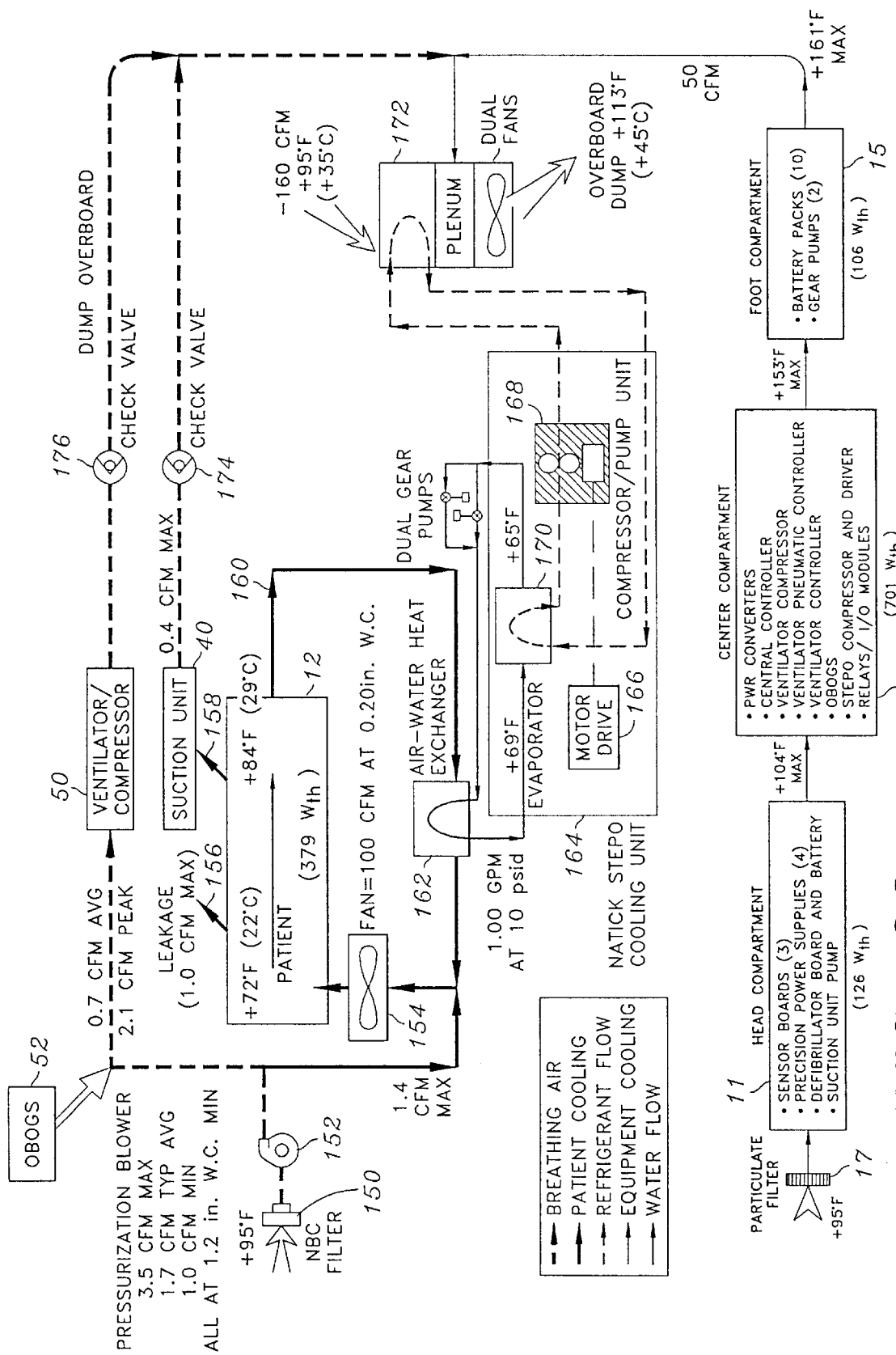
FIG. 23 is a full system schematic diagram of the environmental control system.

With particular reference to FIG. 23, wherein the full system schematic of the environmental control system is provided, a nuclear/biological/chemlcal (NBC) filter 150 and a fan 152 are disposed within the upper housing section fan assembly 30. The fan 152 provides filtered air to cooling fan 154 which directs the filtered air onto the patient 12. A portion of the air brought into the upper housing section via blower 152 is exhausted therefrom as leakage 156. Another portion of the air brought into the upper housing section 26 via blower 152 is provided to the suction unit 40. Another portion 158, the remainder 160 of the air brought into the upper housing section via the blower 152 is re-circulated within the upper housing a section, preferably passing through air/water heat exchanger 162. The heat exchanger preferably provides 1 gallon per minute of temperature controlled water at approximately 20 psid from the cooling unit 164. The cooling unit 164 preferably comprises a motor driver 166 for driving a compressor pump unit 168 so as to circulate refrigerant through an evaporator 170 and a condenser 172 according to well-known refrigeration principles. A check valve 174 prevent back flow of air into the suction unit. Similarly, a check valve 176 prevents back flow into the ventilator/compressor 50. The outputs of the ventilator/compressor 50 and suction unit 40 may either be dumped overboard or dumped into a container, as desired.

Figure 24:
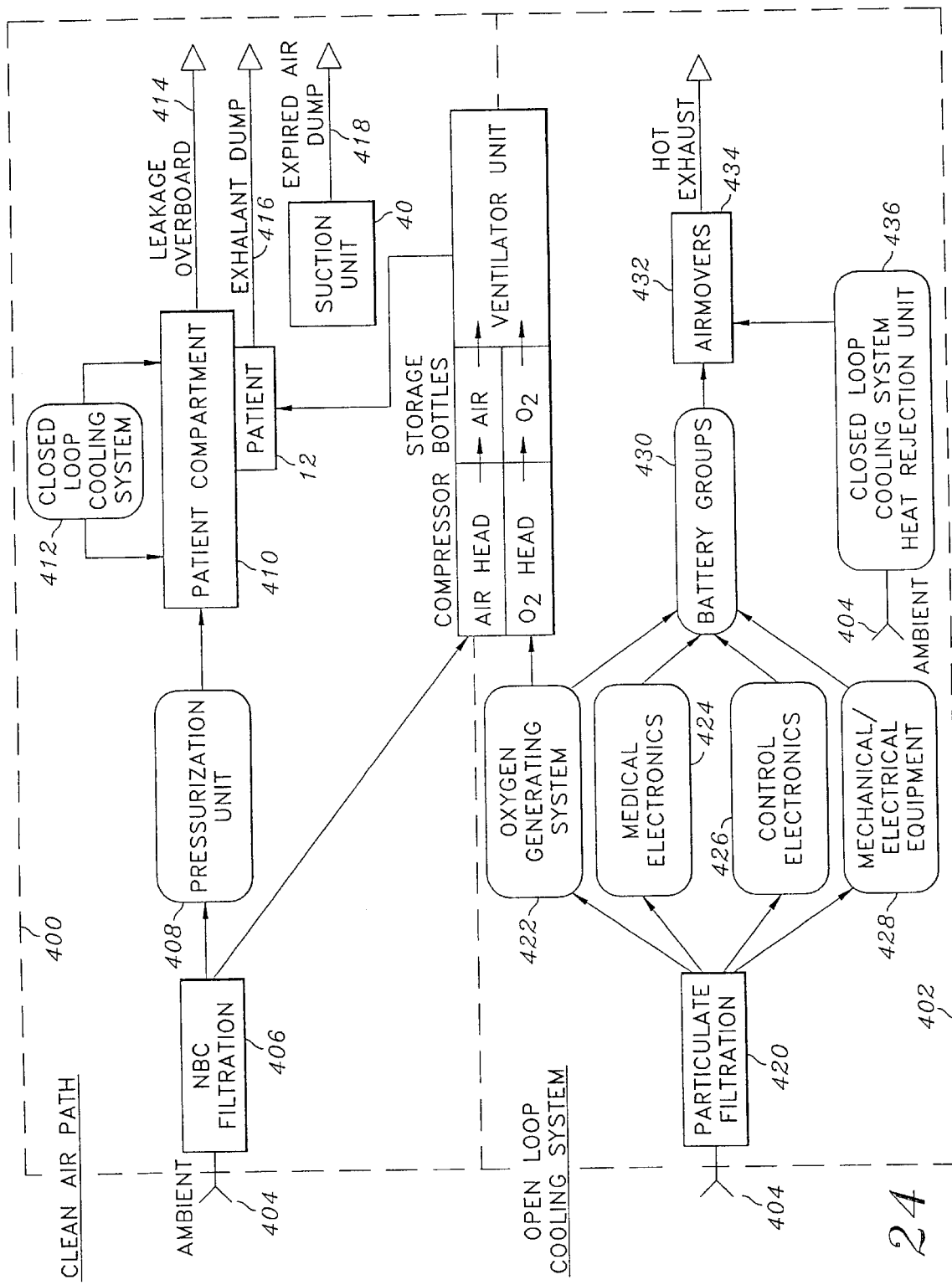
FIG. 24 is a functional block diagram of the environmental control system.

With particular reference to FIG. 24, a functional block diagram of the environmental control system is provided. According to the preferred embodiment of the present invention, both a clean air path 400 and an openloop cooling system 402 are provided. Ambient air 404 is NBC filtered 406.

Optionally, a pressurization unit 408 pressurizes a patient compartment 410 of the upper housing section in a desired fashion. The patient compartment 410 of the upper housing section may be pressurized to a level slightly above ambient to isolate the patient from the environment and care giver. Alternatively, the patient compartment 410 of the upper housing section 26 may be pressurized to a level slightly less than ambient to isolate the care giver from the patient. Closed-loop cooling system 412 facilitates desirable temperature control of the patient compartment 410. When the patient compartment is pressurized slightly above ambient pressure, then leakage overboard 414 occurs. Exhalant dump 416 is also exhausted from the patient compartment. The suction unit 40 provides a dump 418 overboard.

In the open-loop cooling system 402, ambient air 404 is subjected to particulate filtration 420. The particulate filtered air is then provided to the oxygen generating system 422, the medical electronics 424, the control electronics 426, and the mechanical/electrical equipment 428, all of which receive electrical power from the battery groups 430. The battery groups 430 provide electrical power to the various air movers 432 which then exhaust hot air 434 out of the system. The hot exhaust receives its heat from the closed-loop cooling system heat rejection unit 436.

Figure 25:
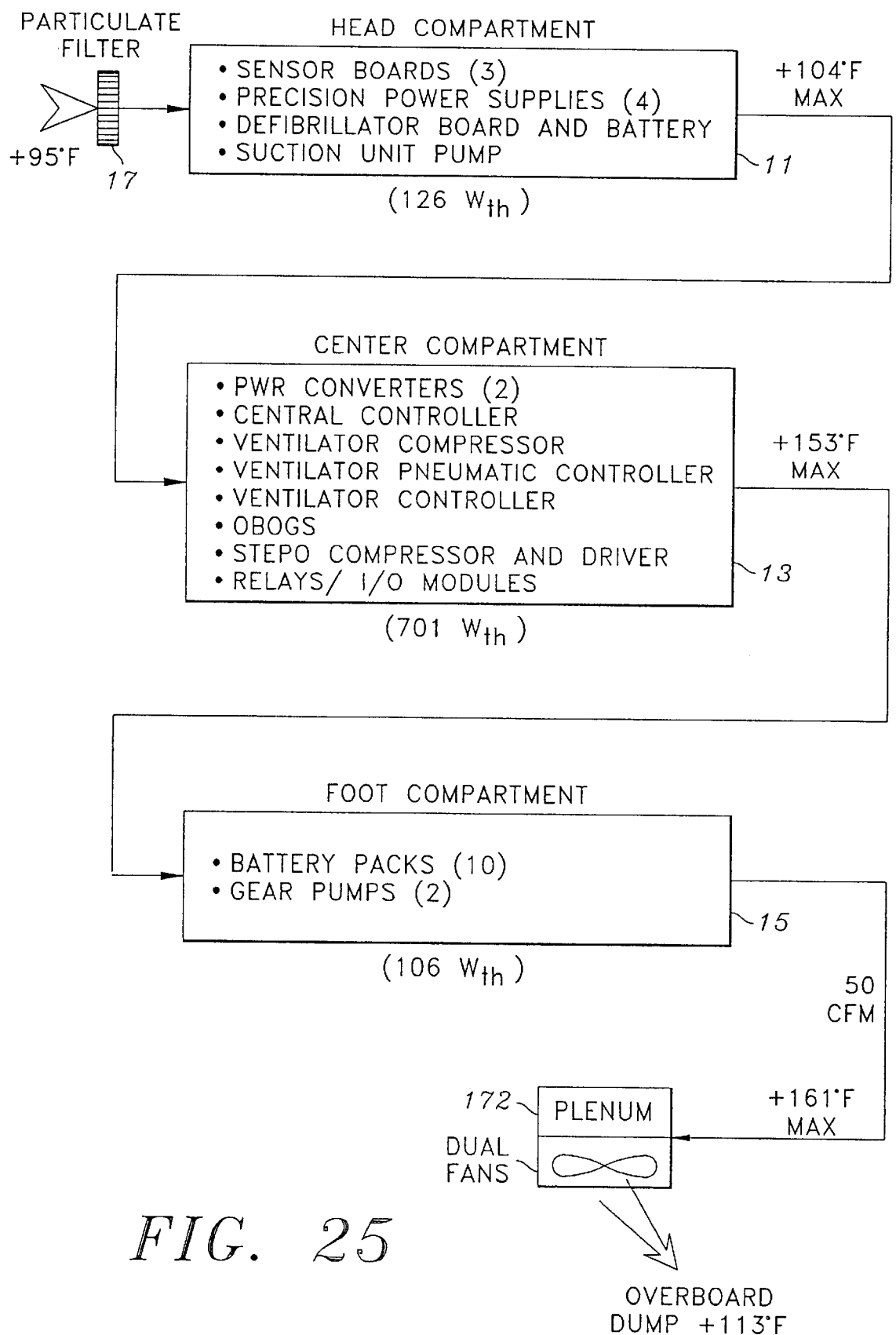
FIG. 25 is a block diagram of the environmental control system equipment cooling subsystem.

Referring now to FIG. 25, the particulate filter 17 provides particulate filtered air to the head compartment 11, center compartment 13, and foot compartment 15, in that order. Within the head compartment 11, sensor boards, precision power supplies, defibrillator board and battery, and the suction pump are cooled by the particulate filtered air. Within the center compartment 13, the power converters 44, central controller 46, ventilator compressor 50, ventilator pneumatic controller 48, onboard oxygen generation system 52, compressor 51 as well as any other electrical devices disposed therein are cooled by the particulate filtered air. In the foot compartment, the battery packs 78 and gear pumps 4 are filtered by the particulate filtered air.

Figure 26:
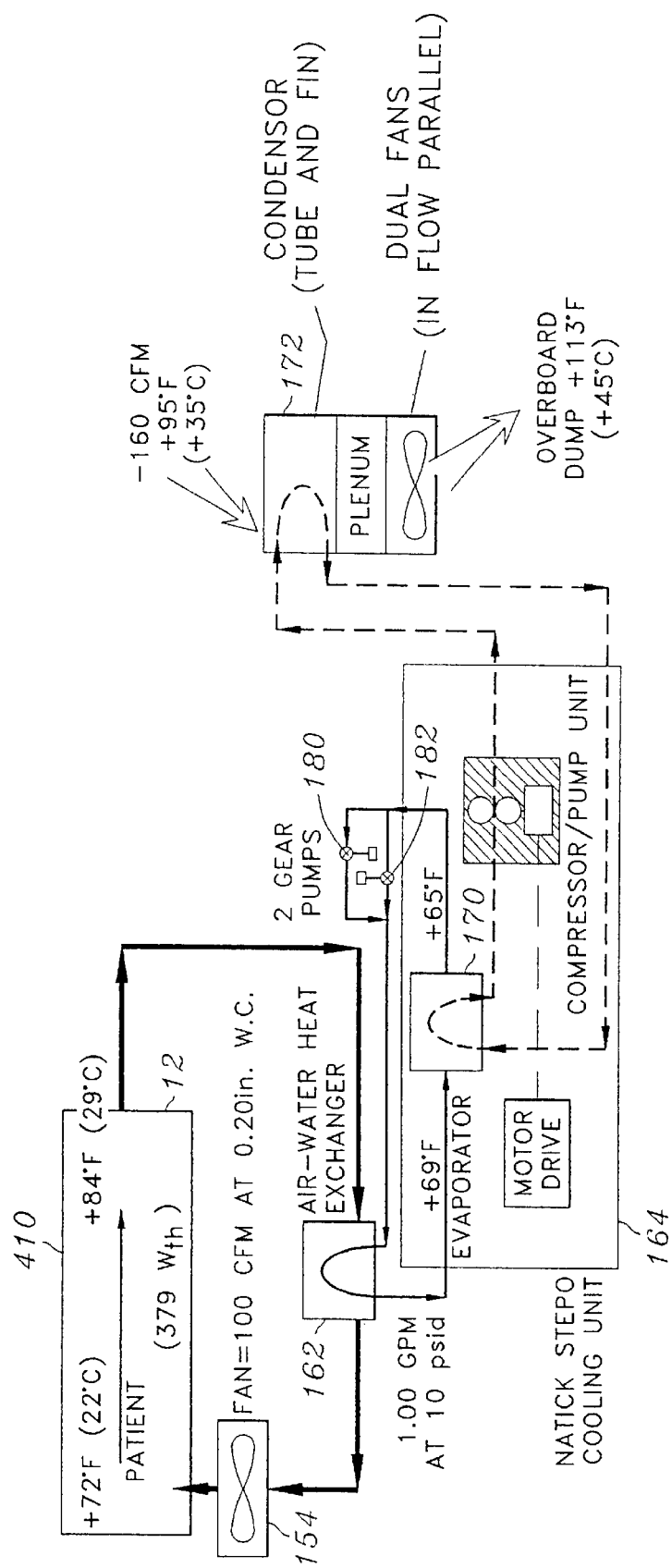
FIG. 26 is a block diagram of the environmental control system patient cooling subsystem.

Referring now to FIG. 26, the patient cooling subsystem comprises a generally re-circulating air system wherein fan 154 provides the patient 12 within the patient compartment 410 defined by the upper housing section with temperature controlled air, preferably at 100 cubic ft. per minute at 0.20 inches water column. The air is provided to the patient at approximately 72° F. (22° C.). Approximately 379 watts of heat must be removed from the patient compartment 410 in order to maintain the exhaust temperature therein at approximately 84° F. (29° C.). The recirculating air is exhausted from the patient compartment 410 and provided to an air/water heat exchanger 162 which preferably circulates water at approximately 1 gallon per minute at 20 psid therefrom to the cooling unit 164. Water preferably exits the cooling unit 164 and enters the air/water heat exchanger 162 at a temperature approximately 65° F. and is pumped by two redundant gear pumps 180 and 182. After leaving the air/water heat exchanger 162, the water is at approximately 69° F. and is cooled by the evaporator 170 of the cooling unit 164 back to approximately 65° F.

Figure 27:
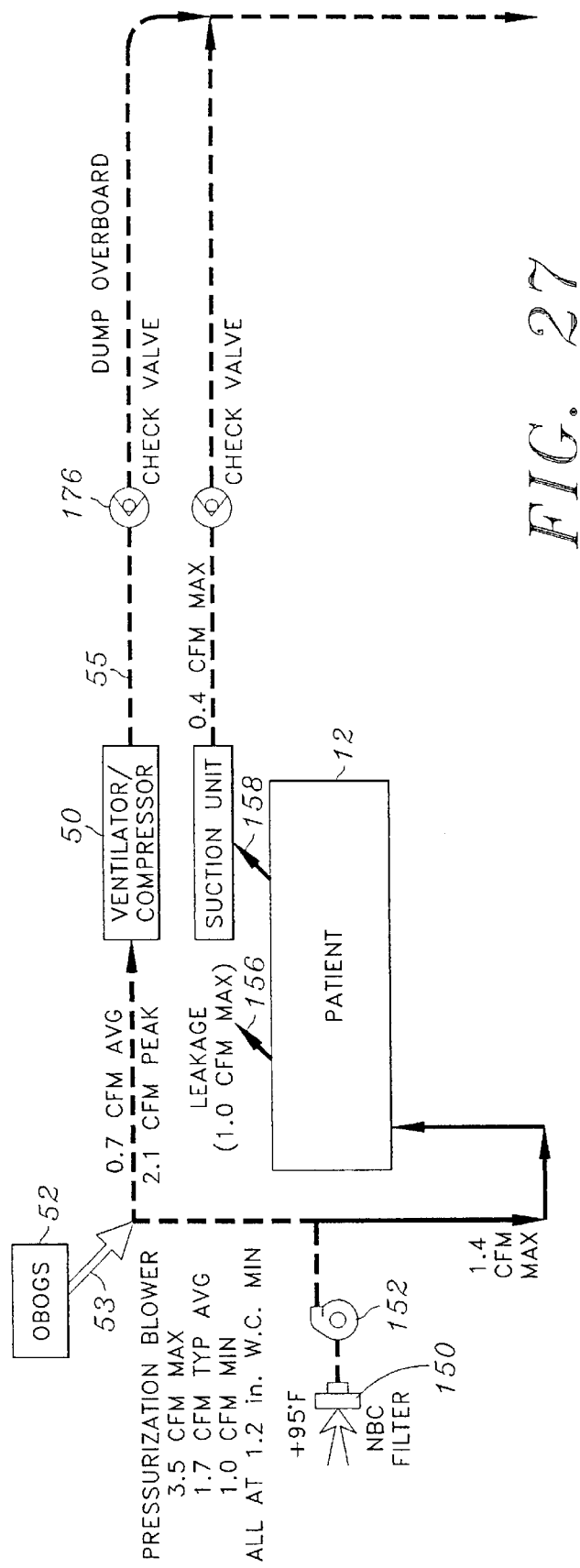
FIG. 27 is a block diagram of the environmental control system pneumatic subsystem.

With particular reference to FIG. 27, the pneumatic subsystem is shown. The onboard oxygen generator 52 provides oxygen or oxygen enriched air 53, preferably at a rate of approximately 0.7 cubic ft. per minute average, 2.1 cubic ft. per minute peak, to the ventilator/compressor 50. Exhaust air 55 from the ventilator/compressor passes to the patient 12 through check valve 176 and is preferably dumped overboard. Alternatively, the exhausted air may be filtered for later analysis.

The NBC filter 150 preferably provides 3.5 cubic ft. per minute max, 1.7 cubic ft. per minute average, and 1 cubic ft. per minute minimum, at approximately 1.2 inch water column minimum. Air from the NBC filter 150 and blower 152 provides air to both the ventilator/compressor 150 and the patient 12.

Figure 28:
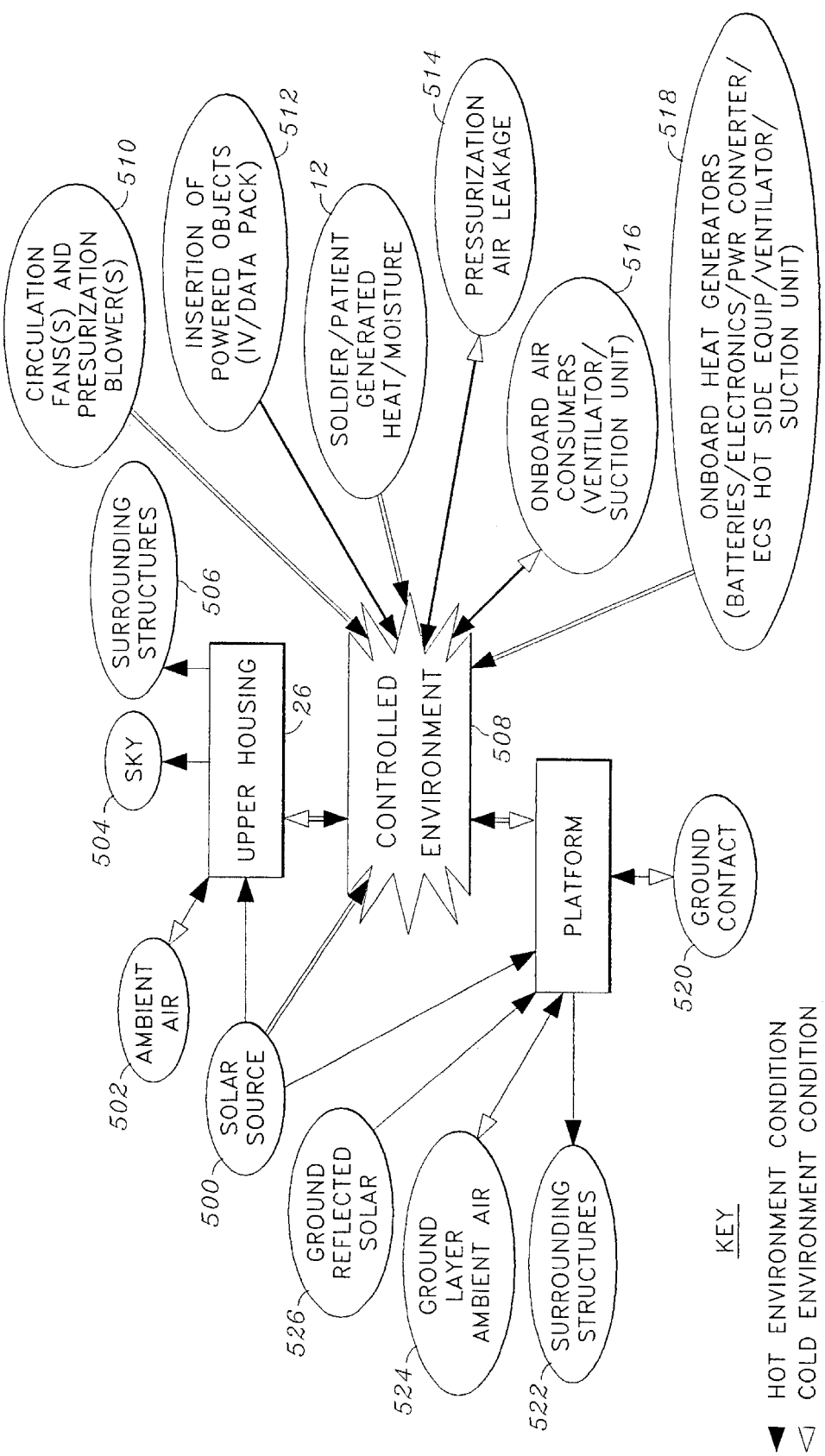
FIG. 28 is a schematic representation of the heat load interactions.

Referring now to FIG. 28, a heat load interaction diagram is provided. The upper housing section 26 receives heat load from the solar source (i.e., the sun), ambient air 502, the sky 504, and surrounding structures 506. The controlled environment 508 receives heat loading from the solar source 500, the upper housing section 26, circulation fans and pressurization blowers 510, the insertion of powered objects 512, such as the IV and the data storage device, and the patient 12. Additionally, onboard heat generators 518 include the batteries, electronics, power converter, environmental control system hot side equipment, ventilator, and suction unit. The lower housing section is subject to heating and/or cooling via ground contact 520, the effects of surrounding structures 522, ground layer ambient air 524, and ground reflective solar radiation 526. The controlled environment is also subject to pressurization air leakage 514, and onboard air consumption 516.

Figure 29:
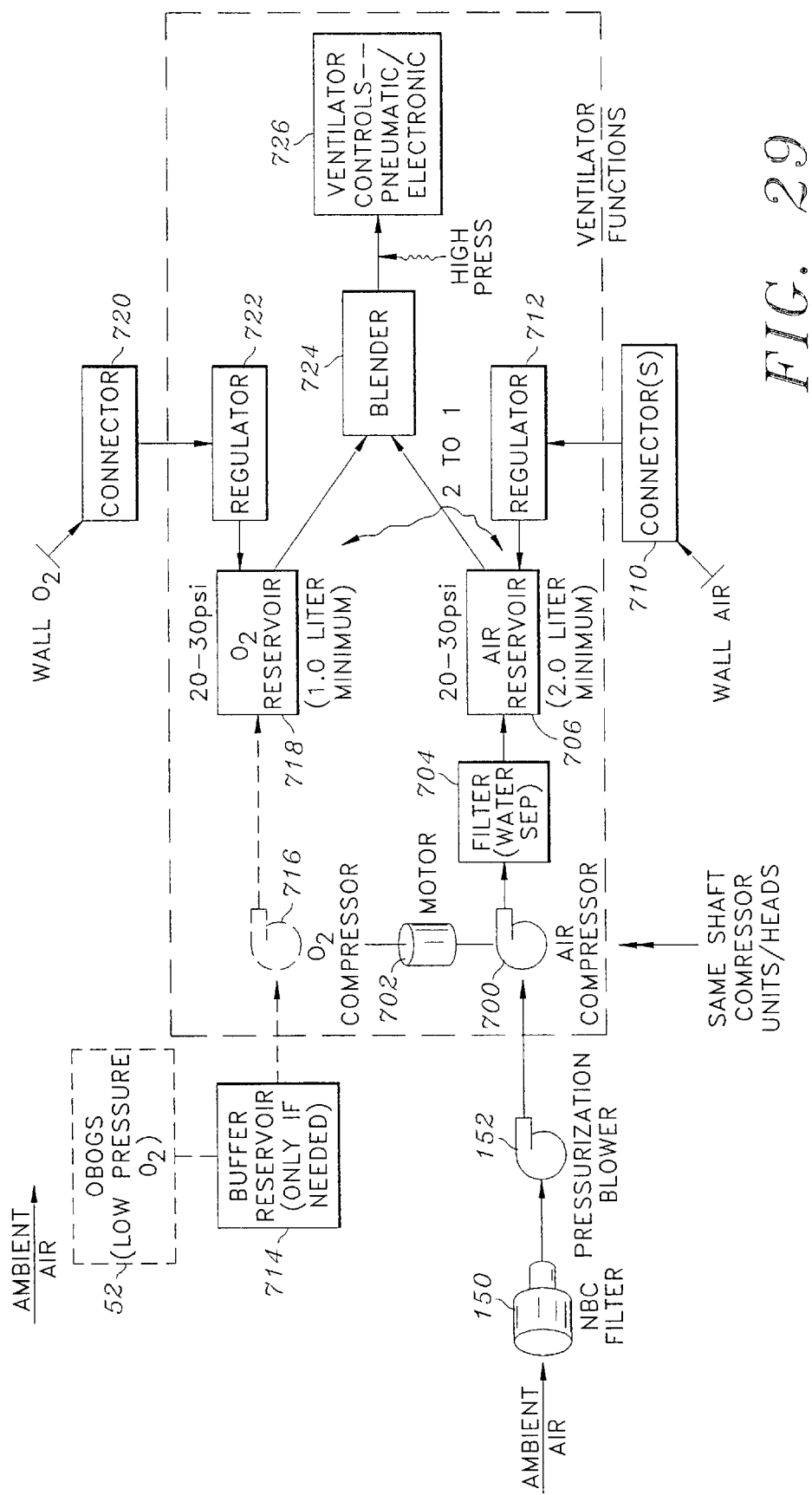
FIG. 29 is a block diagram of the ventilator.

Referring now to FIG. 29, a schematic depicting operation of the ventilator is provided. Ambient air is drawn through the NBC filter 150 by fan 152. Air compressor 700 driven by motor 702 provides air through water separation filter 704 to air reservoir 706. Wall air is provided through connectors 710 to the regulator 712. The output of the regulator 712 is provided to the air reservoir 706.

Ambient air is also provided to the onboard oxygen generator system 52, the output of which is low pressure oxygen or oxygen enriched air which is provided to optional buffer reservoir 714. From the optional buffer reservoir, oxygen flows through oxygen compressor 716 to oxygen reservoir 718 where it is stored at approximately 20 to 30 psi. Oxygen may also be provided to the oxygen reservoir 718 from a wall outlet via connector 720 and regulator 722. Oxygen from the oxygen reservoir 718 is blended with air from the air reservoir 706 via blender 724 having a high pressure (20–30 psi) output. Ventilator controls 726 then facilitate the administration of oxygen or oxygen enriched air to the patient 12.

Figure 30:
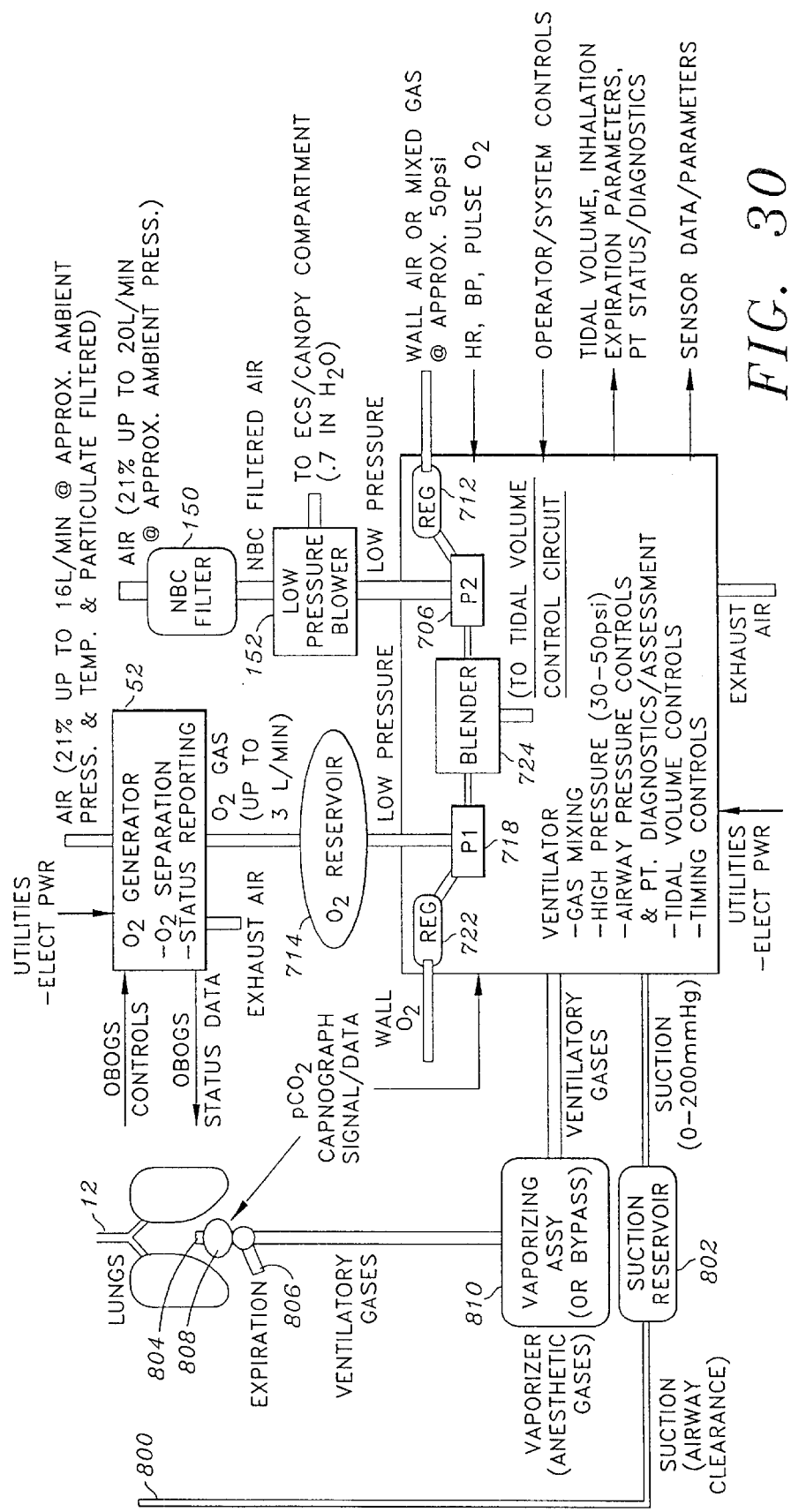
FIG. 30 is a block diagram of the ventilator and onboard oxygen generator system.

Referring now to FIG. 30, the integration of the ventilator and onboard oxygen generator system and the interfaces thereof are shown. Suction is provided via suction tube 800 so as to facilitate air way clearance. Fluids drawn through suction tube 800 are collected in suction reservoir 802. Preferably, suction between 0 and 200 mmHg. is provided. Ventilation is facilitated via ventilation tube 804 which extends into the patient's trachea and is connected to $pCO_2$ capnograph sensor 808. Exhaust from the ventilation tube 804 is facilitated via expiration tube 806 from $pCO_2$ capnograph sensor 808. $pCO_2$ capnograph signal data is transmitted via capnograph electronics to the system control circuit.

Optional vaporizing assembly 810 facilitates the vaporization of anesthetic gases. The vaporization assembly 810 can be by-passed, as desired.

The ventilator performs gas mixing at a high pressure of between 20 and 50 psi. Air way pressure and tidal volume are controllable, either manually or via the system control circuit. Timing may also be either manually controlled or controlled via the system control circuit.

Figure 31:
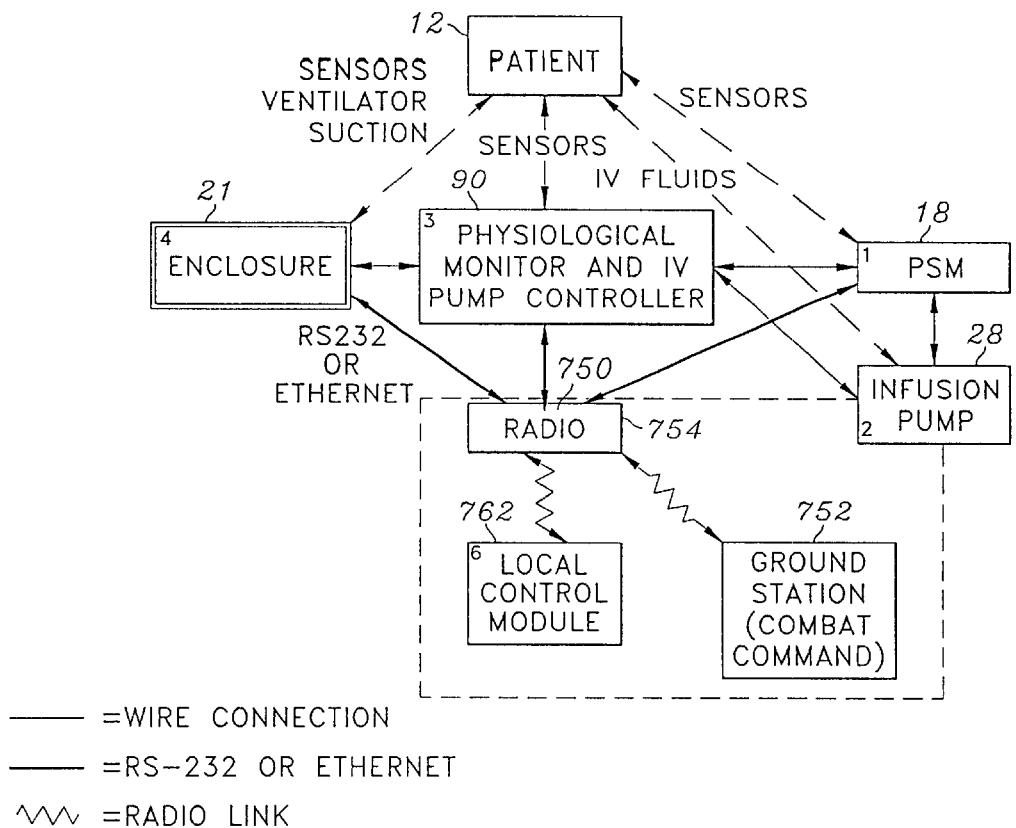
FIG. 31 is a block diagram of the communication system and external interfaces.

Referring now to FIG. 31, the data communication and associated external interfaces are shown. The enclosure, upper housing section 21 houses the patient 12. The physiological monitor and IV pump controller 55 stores the output of sensors attached to the patient 12 and control pump 28. The local control module 762 is a standalone device which may be carried by medical personnel to monitor the status of the patient contained within the self-contained transportable life support system of the present invention as shown in FIG. 1. Thus, a single local control module 762 can be utilized to monitor a plurality of different self-contained transportable life support systems to verify the proper operation thereof and the condition medical patient contained therein.

The personal status monitor 18 monitors the status of the patient and may control the infusion pumps 763 and also communicate with the physiological monitor. The pump 763 may be a portable infusion external to the self-contained transportable life support system. Such communications preferably are facilitated via the radio 754 of the self-contained transportable life support system, or an equivalent external radio.

The data storage device 90 is in communication with a radio 750 so as to facilitate communications with remote medical personnel. Communications are optional and facilitated with administrative personnel to facilitate logistics regarding injured personnel at a ground station 752. Communications with external devices may be either via an RS-232 link, or preferably, an Ethernet link.

Figure 32:
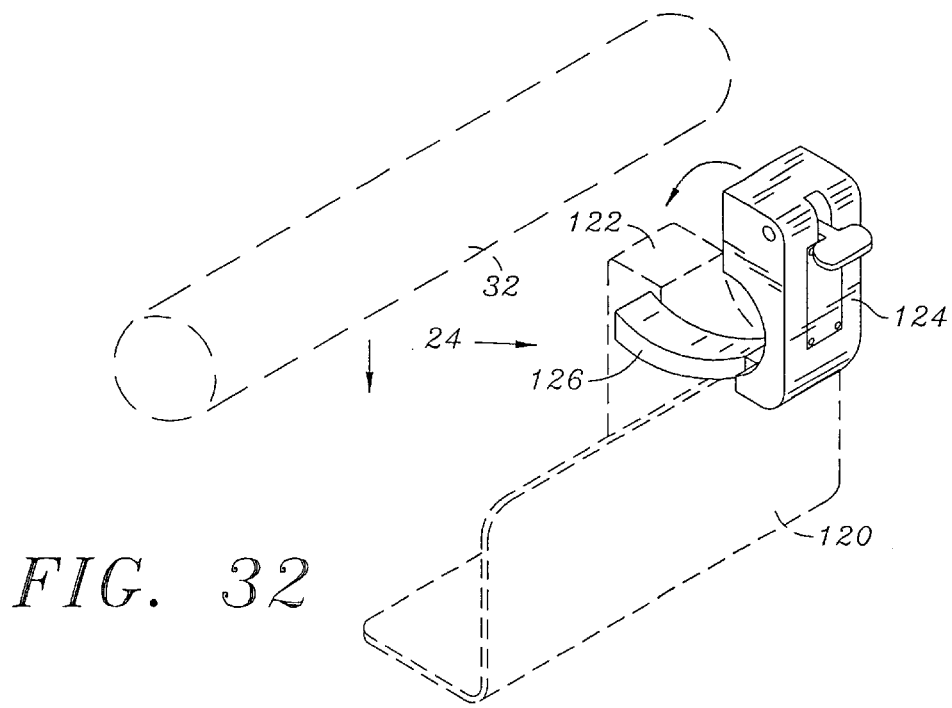
FIG. 32 is a perspective view of a stretcher retention member.

Referring now to FIG. 32, a stretcher retention member 34 according to the present invention is shown. The structure retention member is preferably configured such that attachment of the lower housing section to a stretcher is facilitated by merely dropping or lowering the stretcher upon the stretcher retention members 54 such that the handles 32 of the stretcher 20 contact the stretcher retention members 54 and are captured thereby. Optionally, the stretcher member 34 may be configured such that manual opening thereof is required prior to placing the stretcher 20 thereupon. Once the stretcher 20 is then placed the stretcher retention member 34, the stretcher retention member 34 closes and locks about the handles 32 of the stretcher 20.

According to one preferred configuration of the retention member 34, a lower coupling 122 is formed upon a base 120. The base 120 facilitates attachment of the stretcher retention member 34 to the lower housing section 22 of the present invention. An upper coupling 124 is pivotally attached to the lower coupling 122 and is disposable in open and close positions. In the open position, as shown in FIG. 32, an activation bar 126 extends approximately perpendicularly from the upper coupling 124 such that when a stretcher 20 is laid upon the lower housing section 22, one handle 32 thereof engages the activation bar 126 and pushes the activation bar downwardly, thus rotating the upper coupling 124 into the closed position thereof. When the upper coupling 124 is rotated into the closed position thereof, the upper coupling 124 locks in place, such that it must be manually unlocked in order to remove the stretcher 20 from the lower housing section 22.

Figure 33:
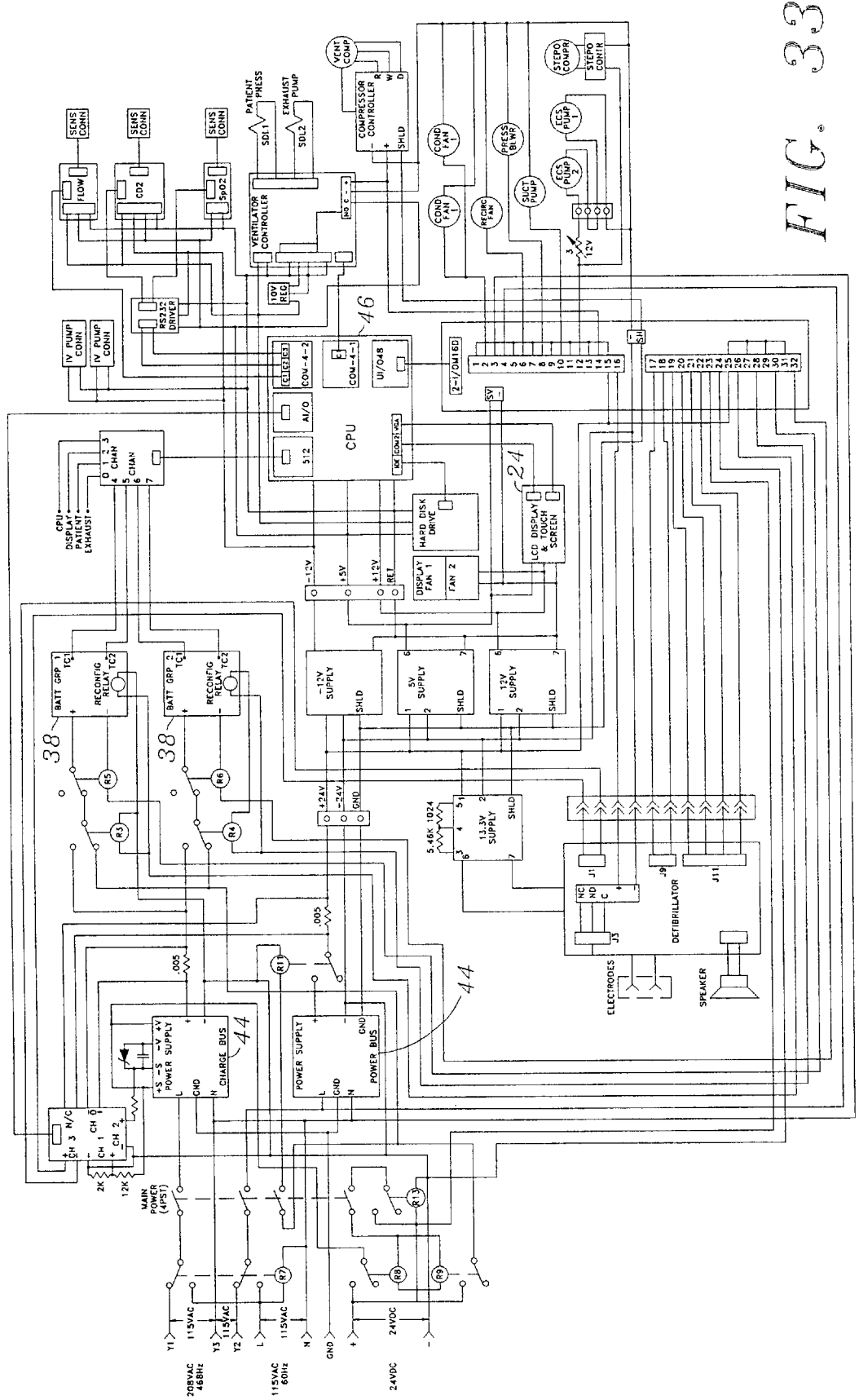
FIG. 33 is an electrical schematic of the present invention.

Referring now to FIG. 33, a schematic of the present invention is provided. According to the present invention, a variety of different power inputs may be utilized to operate the medical devices thereof and/or simultaneously charge the batteries thereof. According to the preferred embodiment of the present invention, such external power may comprise 115/200 VAC, 400 Hz; 120 VAC, 60 Hz; 25 VDC. This power is provided to power converters 44 which provide nominal 25.2 volts DC to facilitate operation of the medical devices and/or charging of the batteries 38. Control circuit 46 facilitates cooperation of the different medical monitoring and medical treatment devices, so as to provide proper medical care for the patient, depending upon the particular medical problems thereof.

Figure 34:
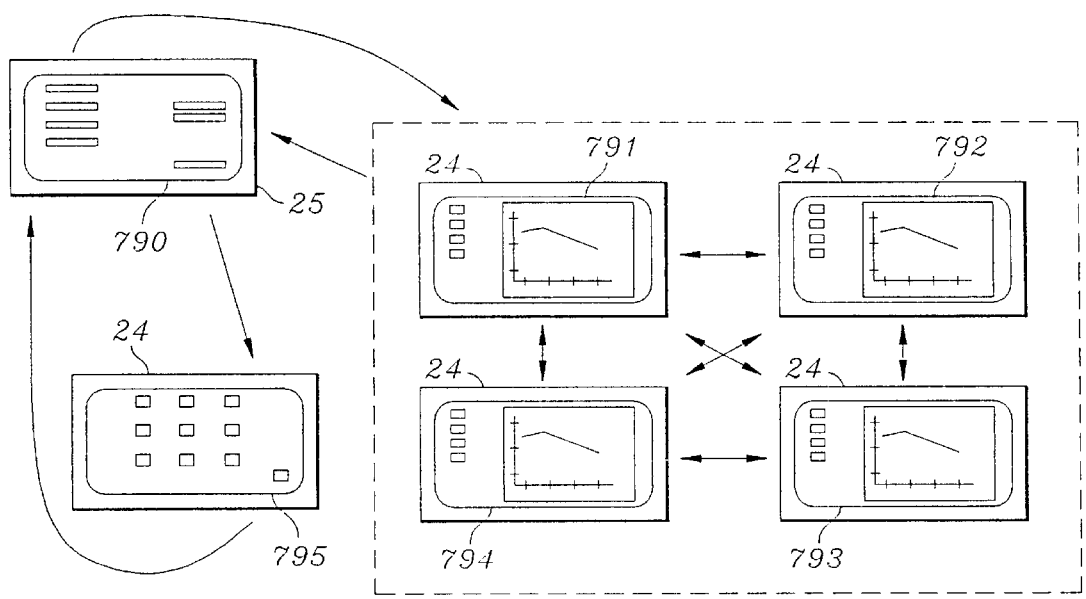
FIG. 34 is a flow diagram showing different display presentations.

Referring now to FIG. 34, the touch screen monitor 24 displays various medical parameters 790, 791, 792, 793 and 794, as well as displaying controls 795 for facilitating desired operation of the medical devices.

The medical monitoring devices and medical treatment devices of the present invention are preferably under the control of a control circuit 46, preferably a general purpose microprocessor, which runs an algorithm program to facilitate desired monitoring and control of the medical devices.

Figure 35:
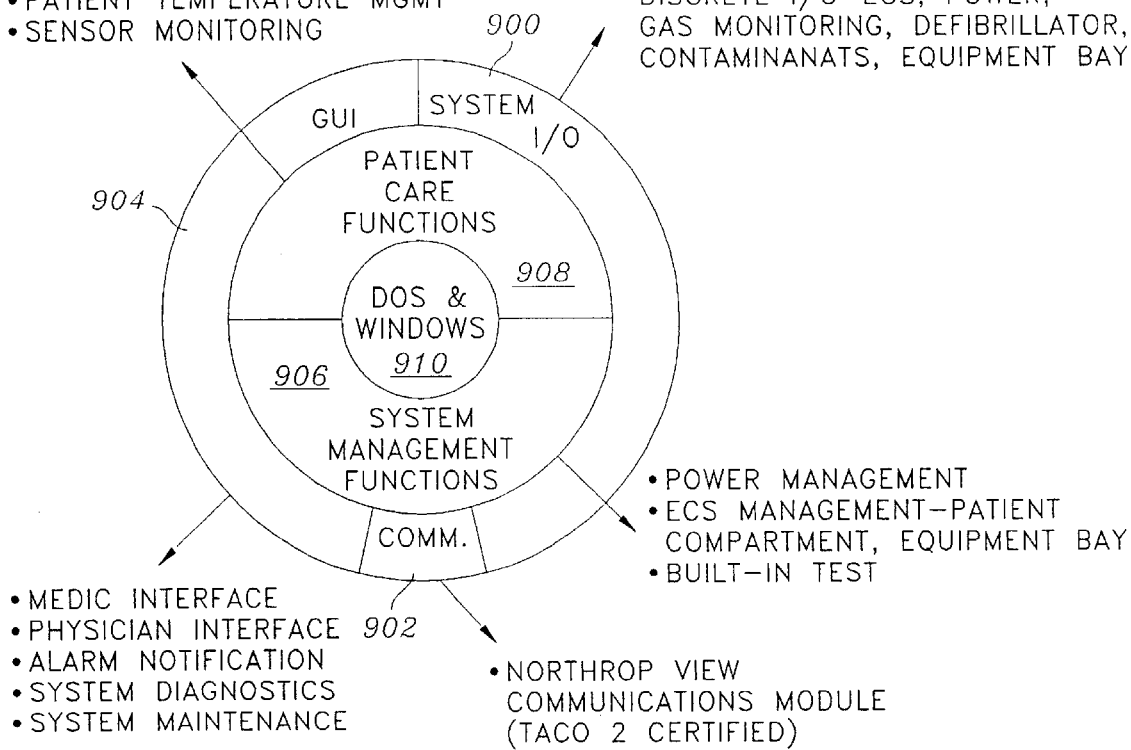
FIG. 35 is a functional diagram showing the software architecture of the present invention.

As shown in FIG. 35, the software architecture comprises system input/output 900, communication 902 and a graphical user interface 904. According to the preferred embodiment of the present invention, system management functions 906, as well as patient care functions 908 comprise applications which run under any suitable operating system.

The system input/output includes device input/output, data storage device, ventilator, touch screen, defibrillator, radio frequency communications, infusion pump and physiological sensors. The screen input/output for the environmental control system, power, gas monitoring, contaminants, defibrillator, and equipment bay is also provided. System input/output also includes power management, environmental control system management, i.e., patient compartment, as well as the equipment bay. Preferably, built-in test functions are provided.

The graphical user interface includes ventilator management, onboard oxygen generator system management, defibrillator management, suction unit control, patient temperature management, and sensor monitoring. The graphical user interface also facilitates a medic interface, physician interface, alarm notification, system diagnostics, and system maintenance.

Figure 36:
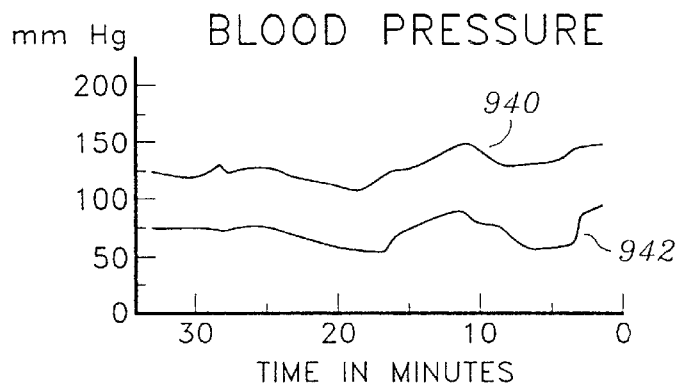
FIG. 36 is a sample screen display showing blood pressure.

Referring now to FIG. 36, a sample display of a screen for indicating blood pressure is provided. Systolic blood pressure is indicated by the upper most curve 940 and diastolic blood pressure is indicated by the lower most curve 942.

Figure 37:
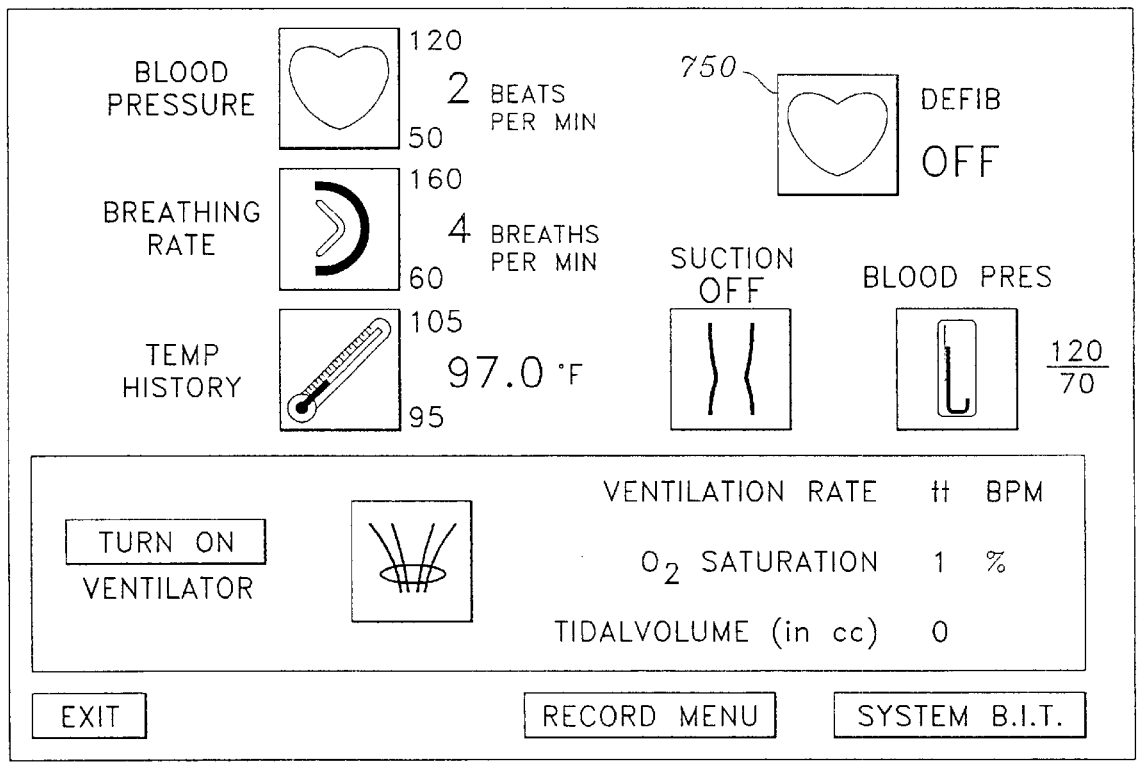
FIG. 37 is a sample display showing a plurality of controls.

Referring now to FIG. 37, a sample display indicating the status of the medical devices, i.e., defibrillator and ventilator, as well as patient medical parameters is provided. Since a touch screen monitor is utilized, the medical devices of the self-contained transportable life support system of the present invention can be both monitored and controlled from the touch screen monitor 25. For example, a defibrillator can be turned off, activated so as to initiate charging, and caused to discharge by pressing the heart shaped symbol 750.

Figure 38:
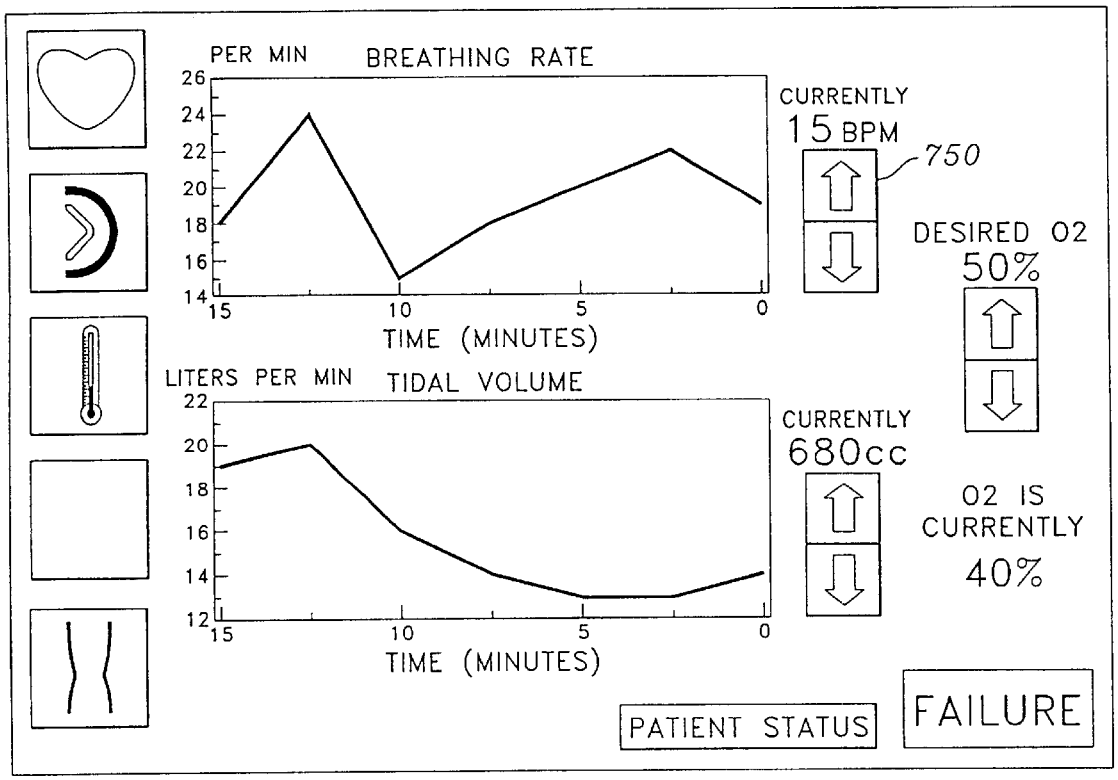
FIG. 38 is a sample screen display showing graphs of breathing rate and title volume.

Referring now to FIG. 38, a sample screen further illustrating medical device status and patient medical parameters is provided. Control of the medical devices is provided via a touch screen interface. For example, by pressing the up arrow 950 associated with breathing rate, the breathing rate provided by the ventilator can be increased. Likewise, oxygen concentration and tidal volume can easily be varied, as desired.

Figure 39:
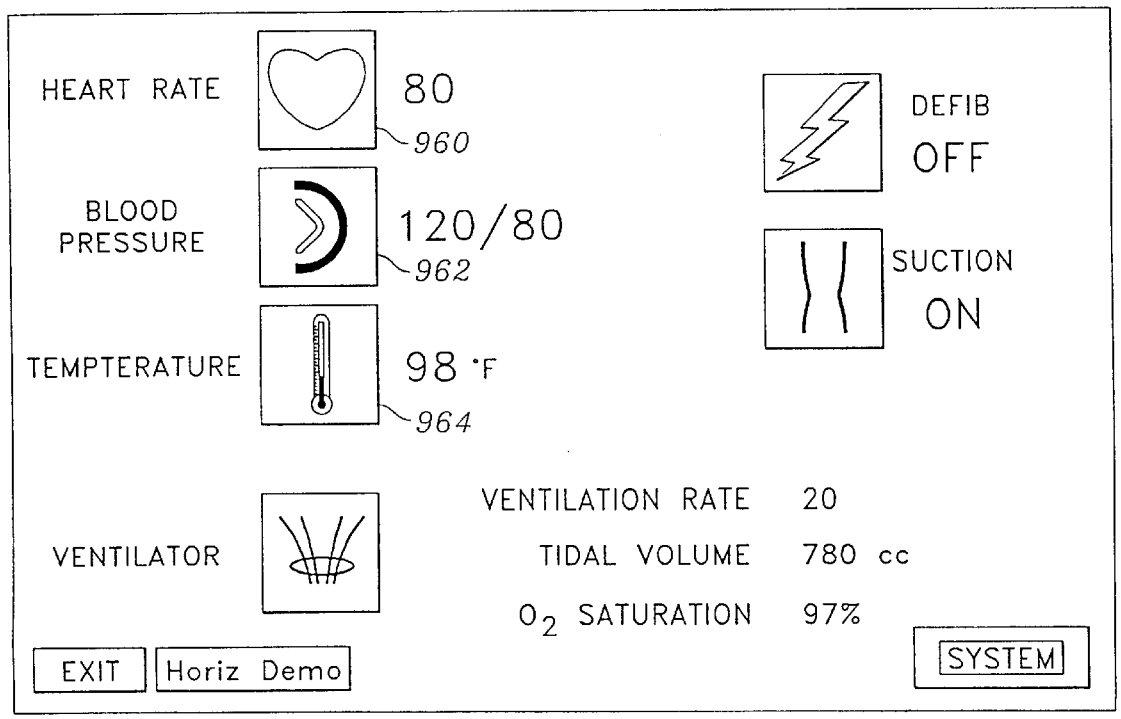
FIG. 39 is a sample screen display showing patient status.

Referring now to FIG. 39, a sample screen showing patient status is provided. As shown, the heart rate 960 is 80 beats per minute, the blood pressure 926 is 120/80, and the patient's temperature 964 is 98° F. The sample screen shows that the defibrillator is off and suction is on and that the ventilator is providing ventilation at a rate of 20 breaths per minute with a tidal volume of 780 ccs. and oxygen saturation of 97%.

Figure 40:
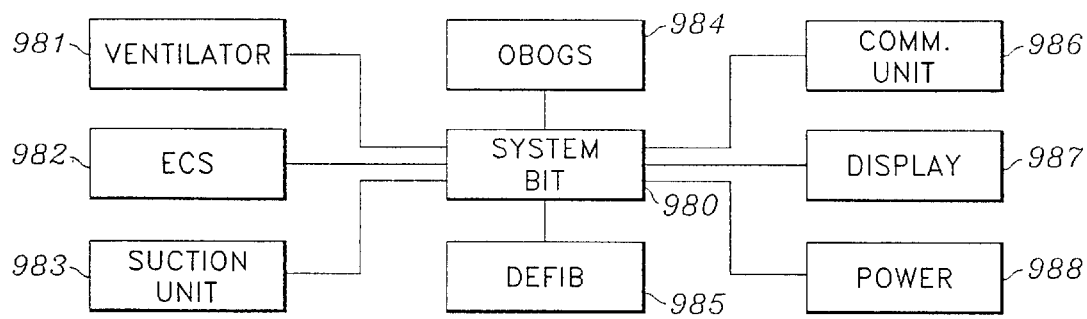
FIG. 40 is a sample screen display showing the results of performing the built in test (BIT), wherein passing a subsystem passing the built in test is represented a green line interconnecting the system BIT symbol and the subsystem symbol and a subsystem failing the test is represented by a red line interconnecting the system BIT symbol and the subsystem symbol.

Referring now to FIG. 40, the screen display resulting from a system self test is shown. The symbol in the center 980 is representative of the system built-in-test (BIT). From the system BIT 980 symbol extends lines to a ventilator symbol 981, and ECS symbol 982, a suction unit symbol 983, an onboard oxygen generator system symbol 984, a defibrillator symbol 985, a communications unit symbol 986, a display symbol 987, and a power symbol 988.

When the system built-in-test is successful for a particular subsystem and its communications channel, then the line from the system BIT symbol 980 to that subsystem and the subsystem symbol will be green in color. A subsystem failure is indicated by displaying a green line from the system built-in-test symbol 980 to the appropriate subsystem and the subsystem symbol will be red in color. A failure of the communications channel from the system to the subsystem will be indicated by displaying a red line from the system built-in-test symbol 980 to that subsystem symbol and the subsystem symbol will be red in color because its status cannot be verified. For example, if the communications unit 986 failed the system built-in-test, then the line joining the system built-in-test symbol 980 to the communications unit symbol 986 would be green and the communications unit symbol would be red instead of green. Additionally, if the communications channel to the ventilator 981 failed the system built-in-test, then the line joining the system built-in-test symbol 980 to the ventilator symbol 981 would be red instead of green and the ventilator symbol 981 would be red instead of green because its status cannot be verified.

As described in more detail below, the self-contained transportable life support system incorporates a control circuit that functions to monitor, control, prioritize and regulate power to the functional devices and circuits of the life support system. As will be recognized by those skilled in the art, the particular manner in which the control circuit performs those functions may be varied substantially without departing from the broader aspects of the present invention. Implementation of the control circuit functions will vary in accordance with the operating characteristics of the particular devices and other circuits cooperating with the control circuit, as well as the desired level of sophistication to be implemented. In one embodiment, the control circuit functions via a single redundant data bus to communicate information to and from the functional devices and circuits via one or more electrical busses, to which the medical devices and other circuits are operatively connected. In such a case, information to and from the control circuit may be formatted in digital packets whereby each functional device and circuit may be separately addressed to communicate control and data signals.

In another implementation, the control circuit may be implemented in a construction whereby the control circuit is separately connected to the other functional devices and circuits via substantially dedicated circuit paths. In either case, the control circuit provides adaptive control of the functional devices and circuits in order to maintain desired life support conditions of the patient.

Programing instructions suitable to implement the functions of the control circuit are submitted with this application. However, those instructions are intended to be exemplary and may be supplemented, modified or rearranged without departing from the broader aspects of the adaptive control implemented by the control circuit. That adaptive control allows the life support system to function independent of operator intervention, as may be required during periods of patient transport, or when other patient requirements limit the immediate attention that can be provided by appropriate medical personnel.

Once the patient is placed in the housing, and the housing is sealed, the control circuit may be placed in an automatic mode whereby monitoring and treatment functions can be selectively implemented, modified, sequenced and terminated by the control circuit, without need for operator intervention.

The control circuit is also operable in a manual, or partially manual mode, whereby some or all of the functions of the control circuit may be manually regulated by an operator, overriding control circuit programming. In other embodiments, the control circuit may function to facilitate manual operation of only select functions of a medical monitoring device, medical treatment device or environmental control device. Moreover, such manual operation may be effected by medical personnel at a remote station, in radio communication with the life support system, whereby the patient life support conditions and environmental conditions within the housing may be remotely monitored and regulated. The particular delegation of which functions may be manually controlled, and the response of the control circuit to such manual control are matters which may be varied in accordance with the desired sophistication of the control system, without departing from the broader aspects of the present invention.

Figure 41:
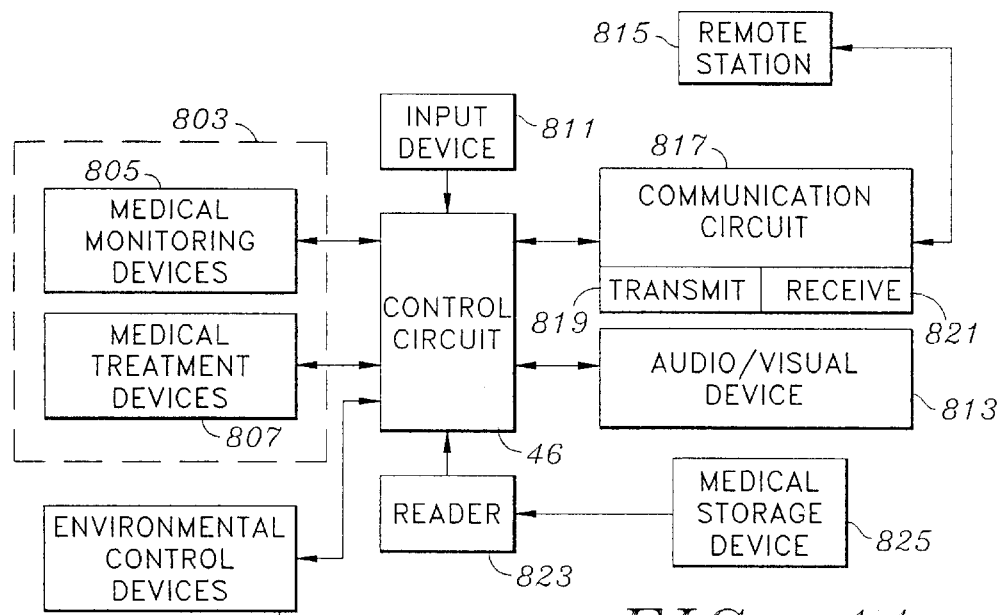
FIG. 41 is a simplified block diagram illustrating operation of the control circuit.

FIG. 41 is a simplified block diagram illustrating operation of the control circuit to provide adaptive control of the interconnected functional devices and circuits. As illustrated therein, control circuit 46 is in bidirectional communication with the medical device 803, which includes medical monitoring devices 805 and medical treatment devices 807, the control circuit is thereby operative to receive information from the medical monitoring devices 805, and to regulate operation of medical treatment devices 807, in response to that information. For example, a medical monitoring device may be implemented as an electrocardiograph and the medical treatment devices 807 may be implemented as defibrillator. For example, information from the medical monitoring devices 805 may thereby provide information respecting cardiac condition of the patient. In accordance with preset threshold conditions, the control circuit is operative to implement programming to activate the medical treatment device, as necessary to bring the monitored life support condition to acceptable parameters.

The control circuit 46 is operative to provide adaptive control of the medical treatment devices, based upon not simply one condition in isolation, but rather upon an evaluation of multiple life support conditions, and the interrelationship thereof. As a result of such evaluation, the control circuit 46 may regulate the operation of the medical monitoring devices 805, the medical treatment devices 807 and the environmental control devices 809.

The control circuit 46 can monitor, implement, modify, sequence and/or terminate the monitoring functions of medical devices 805, and/or the treatment functions of one or more medical treatment devices 807, in response to adaptive program control.

Environmental control devices 809 may be implemented as monitoring devices and/or regulating devices operative to sense and/or regulate environmental conditions within the housing. Such conditions may include temperature, sound, light, pressure, humidity patient inclination and other environmental conditions. Thus, for example, environmental control devices 809 may be operative to sense chemical or bacterial conditions within the housing, and to implement air filtration functions to deplete any chemical, biological, or radiological contaminants. In the presently preferred embodiment, such air filtration functions are normally implemented on a continuous basis in order to assure that the environmental conditions within the housing remain isolated from environmental conditions external to the housing.

Input device 811 and audio/video device 813 are preferably connected to an exterior surface of the housing to allow access to the control circuit without the need to sacrifice environmental isolation of the patient within the housing. Input device 811 is operative to input instructions or requests for information to control circuit 46. In response to such instructions or request for information, the control circuit 46 is operative to regulate the operation of the functional devices and circuits in accordance with proper control. Audio/video device 813 permits an operator to view information communicated to the control circuit 46, and monitor the operation thereof. In one implementation, the audio/video device 813 allows for audio communication with the patient within the chamber, and/or an operator located at a remote station 815. The remote station 815 may be located at a hospital or other medical service facility where trained medical personnel may monitor and regulate the operation of the life support system, via a radio frequency link to communication circuit 817.

The communication circuit 817 is provided with a transmit circuit 819 and a receive circuit 821. Transmit circuit 819 and receive circuit 821 are collectively operative to communicate information and instructions between remote station 815 and the control circuit 46. Remote control signals communicated from remote station 815 may be interpreted by control circuit 46 to regulate the operation of medical monitoring devices 805, medical treatment devices 807 and/or environmental control devices 809. A microphone and speaker disposed within the housing facilitates audio communication between the patient and/or local care giver and an operator remote station 815. The patient may thereby verbally communicate his condition and treatment request to the remote station 815, which may in turn access patient life support condition information from medical monitoring devices 805, via control circuit 46. The operator at remote station 815 may further regulate the medical monitoring devices 805 to obtain further information as may be considered useful by the operator. Upon evaluation of such information, the operator at remote station 815 may thereupon direct the control circuit 46 to regulate the operation of medical treatment devices 807 in accordance with a desired treatment plan. The effectiveness of that plan can be constantly monitored by accessing information from the medical monitoring devices 805 and by direct verbal communication with the patient via a microphone and speaker or monitor disposed within the housing.

The life support system may further be provided with a reader 823 operative to read information disposed on a medical storage device 825, and to communicate such information to control circuit 46. Reader 823 may, for example, operate to input information concerning a patient's medical history to the control circuit 46. The control circuit 46 is thereupon operative to regulate operation of the medical monitoring devices 805, medical treatment devices 807 and environmental control devices 809, in response to such information.

As noted above, the control circuit 46 is preferably also operative to simulate a plurality of life support conditions to an operator, to monitor an operator's utilization of the medical devices in response to such simulated life support conditions, and to evaluate the effectiveness of the operator's utilization of the medical devices. The control circuit 46 thereby may operate in a training or simulation mode without any patient present within the housing.

Figure 42:
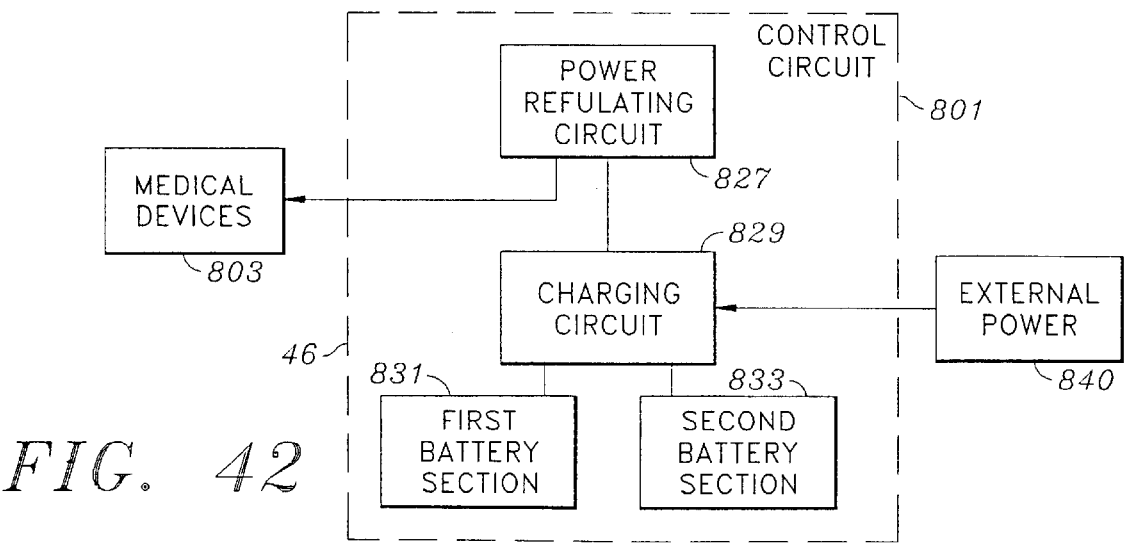
FIG. 42 is a detailed block diagram illustrating the control circuit in further detail.

As illustrated in connection with FIG. 42, the control circuit 46 may also function as a power regulator to regulate the application and distribution of electrical power to the medical devices. As shown therein, the control circuit 46 further comprises power regulating circuit 827, charging circuit 829 and first and second battery sections 831, 833. In this embodiment, the power regulating circuit 827 operates to regulate the operation of charging circuit 829 to alternately charge one of first battery section 831 and second battery section 833, while power is drawn from the other battery section. External power provided to charging circuit 829 may thereby be directed to charge first battery section 831, while second battery section 833 provides output power to medical devices 803 and other functional components of the life support system. In accordance with predetermined parameters, power regulation circuit 827 may thereupon regulate the operation of charging circuit 829 such that external power is applied to charge second battery section 833, while power from first battery section 831 is applied to medical devices 803.

The control circuit 46 may further be operative to regulate the distribution of power from the first and second battery sections 831, 833, in accordance with a preset priority status assigned to the medical devices, environmental control devices and other circuits within the life support system. In that embodiment, the power regulation circuit 837 is operative to monitor the available power from the first and second battery sections 831, 833. The control circuit 46 is operative to monitor the power requirements of the medical devices, environmental control devices and other circuits within the life support system, and to distribute available power to those devices and circuits in accordance with an assigned priority status attributable to those devices and circuits. Moreover, control circuit 46 is further operative to modify the assigned priority status of individual medical devices, environmental control devices and other circuits within the life support system, in response to monitored conditions of the life support system, or in response to manual control. Various other scenarios may be implemented whereby the control circuit regulates power distribution to the individual medical devices, environmental control devices and other circuits in accordance with urgent medical conditions as may arise within the life support system.

As will be recognized by one of ordinary skill, the description of the control circuit 46 may be modified, simplified or enhanced, in accordance with a particular application, without departing from the broader aspects of the present invention.

The transportable life support system of the present invention provides individual, personalized, medical intensive care for military casualties, medical patients, chemical/biologically contaminated patients requiring isolation, and any other personnel who require rapid transport to a medical care facility or sustained ICU care in any care setting.

Additionally, the transportable life support system of the present invention provides means for quickly and easily re-configuring austere facilities into resuscitative, operative, and post-operative medical care facilities. Thus, various non-medical field environments such as those of a ship, aircraft, school, office, home, clinic, etc. may be quickly transformed into an intensive care environment with the use of the transportable life support system of the present invention. The transportable life support system provides the medical monitoring and care devices required for such intensive care applications. Further, the transportable life support system of the present invention can be utilized as a sterile environment for surgical procedures if necessary.

Continuity of care is of paramount importance in the transport of a medical patient from the austere environment of a battlefield or accident site to a location having better medical care facilities, e.g., typically a traditional hospital located remotely from the accident site or battlefield. The transportable life support system of the present invention comprises medical equipment commonly utilized in intensive care situations, which is specifically configured as a lower housing section which can be hand carried by two people and is configured to mount to standard military evacuation vehicles and can be adapted to mount to civilian emergency medical care vehicles or for use in a hospital.

Use of the transportable life support system of the present invention minimizes the number of care givers required during resuscitation and transport and also minimizes the amount of skill required to be possessed by such care givers. According to the preferred embodiment of the present invention, intelligence is provided in the transportable life support system so as to facilitate standalone operations utilizing closed-loop controls. On-board sensors provide inputs for physiological parameter processing which supports intelligent decision making for operation of the various incorporated intensive care medical devices. The physiological parameter processing also facilitates treatment administration by providing instructions to trained or untrained personnel regarding the patient's medical needs. Both patient and life support system status reporting and management is also facilitated.

By providing such closed-loop automation of the transportable life support system of the present invention, it is possible to maximize the time during which a stabilized medical patient may be left unattended or under the care of only the on-board monitoring and control system. This is particularly useful in facilitating the transfer of battlefield or civilian casualties from a hostile environment to a remote hospital wherein care givers are simply not available to facilitate desired constant monitoring.

Additionally, according to one configuration of the present invention, a remote care giver monitors the on-board present invention, a remote care giver monitors the on-board transportable life support system, so as to provide enhanced care for the medical patient. Telecommunications capability supports such remote reporting, query, and command/control operations. Thus, the transportable life support system of the present invention provides an integrated medical device or intensive care unit (ICU) having standalone capability.

According to the preferred embodiment of the present invention, multiple levels of operational and communication capability are provided. The transportable life support system may be configured to operate in a standalone, local, interfaced, or remote mode of operation. The standalone mode of operation provides the most sophisticated autonomous control of the medical devices utilizing sensor inputs from the medical patient. The interface mode of operation allows for electrical, oxygen, and data interface to the transportable life support systems operating environment, e.g., an evacuation vehicle, auxiliary support system, etc., so as to minimize taxing of the transportable life support systems' own resources, thereby enhancing life support systems' own resources, thereby enhancing communication is provided to a remote site, typically a medical professional, who monitors and evaluates data from the transportable life support system and provides trauma treatment inputs to the life support medical devices.

Because of the provision for data storage and communication according to the transportable life support systems of the present invention, the present invention can easily be integrated into various battlefield, civilian emergency logistics, and resource allocation systems. For examples, information regarding battlefield casualties and their medical conditions can be readily compiled and evaluated at a central location. Such logistic considerations may also be useful in civilian applications particularly during catastrophes such as earthquakes, floods, hurricanes, etc.

In order to accommodate transport aboard standard military evacuation vehicles such as the UH-60 Blackhawk helicopter, the UH-1 Huey helicopter, the HumVee, the C-130 helicopter, the UH-1 Huey helicopter, the HumVee, the C-130 winged aircraft, and/or the C-141 fixed wing aircraft, the of the present invention has been configured to fit within a lower housing section having a height of approximately 6 inches. Such configuration is compatible with standard NATO litter mounts such that transportable life support NATO litter mounts such that transportable life support aboard such military evacuation vehicles in the same manner that a standard NATO structure having a battlefield casualty disposed thereupon is carried.

More particularly, the transportable life support system of the present invention is specifically configured so as to facilitate transport upon standard military evacuation vehicles. In order to accommodate such transportation, the physical envelope of the transportable life support system is constrained to 20 inches of height, life support system is constrained to 20 inches of height, 22.75 inches of width, and 85.5 inches of length. The placed and within which the medical devices reside is constrained to a height of 6 inches. Such construction constrained to a height of 6 inches. Such construction present invention attaches such standard military vehicles via the stretcher handles of the standard NATO stretcher to which the transportable life support system is attached. All of the controls and monitoring devices of the present invention are fully operable during transport of the medical patient.

The environmental control system also facilitates patient comfort management, by maintaining a comfortable temperature. The lower housing section provides a physical bed upon which the stretcher and medical patient are placed and also facilitates tie-down thereof, so as to avoid upset and also facilitates tie-down thereof, so as to avoid upset (chamber) provides isolation from adverse chemical/biological environments and also facilitates reverse isolation that may be necessary when the medical patient is contaminated with a chemical or biological agent.

The transportable life support system of the present invention is fully autonomous, utilizing standalone utility capabilities such as internal power, environmental control onboard oxygen generation enhancement, and autonomous communications.

The communications capability of the present invention includes reporting of the status of the patient, as well as the transportable life support system itself. Both local and remotely communicated alarms provide an alert that medical or system parameters have exceeded desirable limits. Recorded information regarding the status of the patient is maintained on board the transportable life support system and may be communicated to another site. The communication of this information is particularly useful when advance preparation is necessary to assure adequate medical treatment for the medical patient. For example, medical personnel may be alerted in advance to the medical patient's arrival and the particular problems and needs of the medical patient such that the appropriate equipment and personnel are on-hand upon the medical patient's arrival. In addition, recording of treatment data, patient data and system data is valuable in medical research.

According to the preferred embodiment of the present invention, the communication system includes location sensing and communicating equipment for providing the location of the transportable life support system to a remote location. It is preferably implemented utilizing the Global Positioning System (GPS). Additionally, the maintenance requirements for the transportable life support system are preferably automated and integrated into the system such that notification of a particular requirement is provided upon the display thereof, as well as instructions for performing such maintenance, if desired. Onboard repair advice and maintenance procedures may optionally also be provided.

By providing the geographic location of battlefield or civilian disaster casualties carried upon the transportable life support system of the present invention, the dispatch of medical personnel, medical equipment, supplies, medicines, etc. to treat the battlefield or civilian casualty is facilitated, as desired.

Local mentoring is provided so as to minimize the training and skill required in order to properly prepare a medical patient for transport, i.e., stabilize the medical patient. Such local mentoring is provided via either autonomous operation of the life support system utilizing onboard sensors and diagnostic software, or, alternatively, via remote teleconsulting utilizing the onboard telecommunications capability.

According to the preferred embodiment of the invention, a training mode is available which allows a user to simulate various different types of trauma casualties, and thus allows care givers to attain proficiency in the proper use of the transportable life support system of the present invention.

The use of the transpotable life support system of the present invention facilitates mobile, agile, war fighting, since the requirement for treating battlefield casualties within the theater of operations is substantially mitigated thereby. Thus, according to the emerging doctrine whereby battlefield casualties are immediately transported to a remote hospital, evacuation of such casualties and replacement thereof with new personnel, e.g., soldiers, is readily facilitated. Further, it is well established that the availability of adequate medical support substantially influences a soldier's willingness to engage the enemy. Thus, the present invention not only enhances the medical treatment of such battlefield casualties and logistics associated with evacuating and replacing such casualties, but also enhances the soldier's ability to fight.

The present invention is capable of providing trauma care within minutes. Because of its lightweight and compact structure, it may readily be deployed to the battlefield front civilian disaster areas where casualties commonly occur or pre-positioned in potential disaster areas. Also, because of its rugged, integrated structure, the present invention may be air-dropped to remote, inaccessible locations and is also configured for air retrieval. Such configuration additionally makes the present invention desirable for use in rescue activities in a remote and inaccessible location, such as a steep, rugged terrain, shipboard and small watercraft, and arctic conditions. The present invention may find particular applicability in cold weather environments, wherein the ability of the environmental chamber to isolate the medical patient from such cold is beneficial.

Such logistic information regarding the geographic origin and present location of battlefield casualties further facilitates practical command decision making regarding real-time modifications to battle plans. For example, an excessive number of battlefield casualties originating from a common battlefront location would tend to be indicative of the need for reinforcements at that location.

The transportable life support system of the present invention is preferably configured to accept computerized medical records, such as those which are anticipated to be carried by individual soldiers. As those skilled in the art will appreciate, attempts are presently being undertaken to incorporate military medical records into dog tags, ID cards, etc. so as to facilitate the automatic retrieval of such data. Thus, the medical history of an individual soldier is quickly transferred to the control system of the transportable life support system such that pertinent information contained therein may be utilized for the diagnosis and treatment of the battlefield casualty.

It is further contemplated that the environmental chamber of the present invention may be utilized in controlled pressure or hyperbaric applications, so as to provide desired medical treatment for the battlefield casualty. For example, in order to treat decompression sickness it may be desirable to increase the pressure within the environmental chamber to a value substantially above ambient air pressure and then to provide a controlled decrease of pressure over time.

Additionally, a pressurization suit may be utilized to control blood flow to portions of a battlefield casualty's body, so as to reduce the likelihood and/or severity of shock and also so as to mitigate bleeding therefrom. For example, repressurizable pants may be utilized to limit blood flow to the lower extremities, so as to mitigate bleeding therefrom and also so as to mitigate the undesirable effects of shock.

Training is facilitated by specifically accommodating well-known training dummies, such as ResusiAnnie (which is commonly used to train for cardiopulmonary resuscitation), and Harvey, a well-known cardiovascular resuscitation dummy.

Three modes of training are provided. In the first mode, a human subject is placed within the transportable life support system of the present invention and a desired physical problem is specified, via a care giver input. The system then simulates sensor inputs from the patient and instructs the care giver to take specific action.

In the second mode of training, a training dummy is utilized in place of a human being.

In the third training mode, the transportable life support system of the present invention is utilized in a standalone mode, i.e., wherein no personnel or dummy is utilized to simulate a battlefield or civilian casualty. A type of injury is specified or randomly selected by the training system and the care giver is instructed as to how to provide care therefor.

A cardiac assist may be provided. The cardiac assist comprises either a mechanical chest compression device, an intra-aorta balloon pump, or an extracorporeal pump.

An extracorporeal pump, oxygenator, and warmer/cooler may be provided so as to facilitate cardiac assist, blood oxygenation, and control of body core temperature. The extracorporeal chiller may be utilized to induce hypothermia, so as to decrease mortality by mitigating the undesirable effects of shock, decreasing blood flow, and consequent bleeding, and decreasing the body's requirement for oxygen. The transportable life support system of the present invention also provides a portable operating lower housing section which may be utilized in various different non-sterile environments for the performance of emergency medical operative procedures. The upper housing section 26 and filter system provides isolation from external contaminants/contagions. Optional isolation gloves provide access to the battlefield casualty while maintaining a sterile environment therefor.

Configuring the environmental chamber for hyperbaric applications also facilitates its use in the treatment of various typical conditions wherein increased oxygen delivery is indicated. Use as a hyperbaric chamber is also preferably facilitated.

According to one preferred configuration of the transportable life support system of the present invention, the medical devices are integrated with the transportable lower housing section so as to provide modular construction. Such modular construction facilitates easy removal and replacement of each medical device, so as to facilitate maintenance thereof. Such modularity also facilitates the configuration of a transportable life support system which is specifically configured for a particular application. For applications wherein a particular type of medical condition is anticipated, only those medical devices required for the treatment of that medical condition are included. This reduces the weight of the transportable life support system, as well as the cost associated therewith. For example, if the present invention were to be utilized at a non-contact sporting event, such as a marathon, then those medical devices for monitoring and supporting cardiac function would be necessary since heart attacks are common during such events. However, those medical devices commonly associated with the treatment of trauma, such as the ventilator, may not be required.

Such modular construction also facilitates quick reconfiguration of the transportable life support system for use in various different applications. Since such modular construction allows for the quick removal and/or replacement of the various medical devices thereof, a transportable life support system can be sent to a central location wherein a variety of such medical devices are stored and can there be quickly reconfigured for a particular use, as desired.

Medical treatment devices of the present invention are responsive to the medical monitoring devices thereof. However, such interactions are based upon the particular medical condition of the medical patient being treated thereby. Thus, rather than a particular medical treatment device being solely responsive to a particular medical monitoring device, each medical treatment device is responsive to those particular medical monitoring devices which are indicative of the medical patient's condition. Thus, according to the preferred embodiment of the present invention, a computer monitors the status of all of the medical monitoring devices and then, based upon a control algorithm, actuates those medical treatment devices which are necessary for the proper treatment of the medical patient. As such, the various complex interactions of the medical monitoring devices and medical treatment devices are possible.

The prioritization schedule utilized to shut down the various systems and/or medical devices of the present invention as battery power diminishes is preferably a dynamic schedule based upon the particular condition of the medical patient. Thus, those medical devices which are most necessary for the proper medical care of the medical patient remain activated the longest. For example, for a medical patient having trouble breathing, the ventilator would be given highest priority and would be the last medical device to be deactivated. In this manner, the time required to transport the medical patient to a hospital is extended and the medical patient's probability of surviving such transport are enhanced.

According to the preferred embodiment of the present invention, an estimated time to reach the destination is entered. Based upon the estimated time of transport and the medical patient's medical condition, a prioritization schedule is generated which assures that those medical devices required for the proper medical treatment of the medical patient remain energized for the duration of the transport. Thus, as the medical patient requires ventilation and the estimated time of transport is two hours, then power is managed in a manner which assures that the ventilator remains activated for two hours.

Approximately one half inch of padding is formed upon the upper surface of the transportable lower housing section such that, when a stretcher is disposed thereupon, the padding cushions the medical patient. In this manner, it is not necessary to support the stretcher its full height above the lower housing section. Rather, the stretcher may be positioned lower, i.e., closer to the lower housing section, thereby reducing the overall height of the life support system. Thus, the medical patient does not rely upon the stretcher to provide a comfortable and resilient surface upon which to lie, but rather is cushioned by the padding of the lower housing section itself.

The handles may optionally be deployable from a stowed position, such that they are out of the way when not being utilized.

The use of such padding also facilitates the transport of a medical patient upon the lower housing section without the use of a stretcher. In this instance, the medical patient lies directly upon the padding of the transportable lower housing section. optionally, handles are formed directly to the lower housing section to facilitate carrying thereof without an attached stretcher.

Thus, the padding formed upon the lower housing section defines a bed for the medical patient. Tie downs, belts, and/or buckles are optionally provided so as to secure the medical patient to the lower housing section, to prevent undesirable movement thereof during transport and/or treatment.

The transportable life support system of the present invention is preferably configured to be airworthy. Thus the transportable life support system does not radiate excessive levels of electromagnetic radiation. Further, the transportable life support system is configured so as not to be substantially susceptible to environmental electromagnetic radiation, such as that generated by an aircraft or vehicle.

The transportable life support system is configured so as to be compatible with utilities commonly found upon military vehicles and in medical environments such as power, oxygen, etc.

According to the preferred embodiment of the present invention, brushless exhaust fans commence operation before power is applied to any other electrical circuit of the present invention. The exhaust fans purge air from within the lower housing section, thereby likewise purging any oxygen which potentially leaks from the oxygen reservoir and/or lines and/or pressurized oxygen bottles, as well as any hydrogen which may potentially leak from batteries. Thus, actuating the brushless exhaust fans first mitigates any explosion or fire hazard associated with the presence of such gases within the lower housing section.

According to the preferred embodiment of the present invention, the equipment and patient air paths are completely separate from one another. Preferably, the air path of the equipment bay within the lower housing section is such that air is drawn over the equipment contained therein, from one end of the lower housing section to the other end thereof. Preferably, the air within the upper housing section 26, as well as the air provided to the ventilator, is pre-filtered through a nuclear, biological, and chemical (NBC) personal filter, such as those commonly used in military gas masks.

A hot air blanket may be utilized to distribute hot air to a medical patient through a porous side thereof. Thus, hot air flow is primarily directed from the blanket to the medical patient. Optionally, a pair of hot air blankets may be utilized such that the medical patient lies upon one and is covered by another. The hot air may be collected under the upper housing section and then recirculated, so as to further enhance rewarming.

Alternatively, a water blanket may be utilized to distribute hot water to a bladder-type blanket. Again, a water blanket may be utilized both under and on top of the medical patient. The water is recirculated and reheated, as necessary. Dry blankets may utilize either the medical patient's own body heat or an electrical or chemical heating pad. Again, dry blankets may be placed both beneath and on top of the medical patient. Either the hot air blanket, water blanket, or dry blanket may be formed in a modular fashion so as to facilitate localized heating of the medical patient as desired.

Upper housing section heating can be utilized to warm the air within the upper housing section in order to facilitate rewarming.

Rewarming of the medical patient is preferably performed with the upper housing section 26 in place, so as to provide protection from environmental elements.

Body heating may additionally be accomplished via extracorporeal warming of the medical patient's blood.

Rewarming of the medical patient may occur either gradually or at a maximum rate. Gradual rewarming is preferably performed at approximately 1° F per hour.

The standard approach for rewarming a hypothermic medical patient is total body immersion in a fluid bath, generally not exceeding 110° F. The objective is to rewarm the medical patient's body as rapidly as possible, but also to limit the temperature applied to the skin to less than 110° F. in order to avoid skin and/or tissue damage. Such fast rewarming may be indicated by severely depressed cardiac function or circulation. It is generally necessary to bring the core temperature to above 90° F. before adequate cardiac contractility can be resumed in order to facilitate sustained circulation. Defibrillation may also be necessary to restore cardiac rhythm if fibrillation occurs after the cold arrest.

The defibrillator of the present invention is preferably configured so as to be inoperative when the medical patient is under hypothermic conditions, since use thereof would not be beneficial to a hypothermic medical patient.

The hot air blanket preferably comprises a Bair-Hugger type of blanket. When hot air is blown through a blanket having an aluminized plastic layer on one side thereof and a very porous material on the other side thereof so as to facilitate desired hot air distribution. In this manner hot air can be provided to a hypothermic medical patient over a very large area thereof. Clinical reports claim the hot air blanket to be as effective as water blanket for the rewarming of hypothermic medical patient using only topside coverage thereof.

optionally, the padding formed upon the lower housing section is either porous or has air channels formed therethrough so as to facilitate hot air distribution over the lower surface of the medical patient.

The lower housing section 22 preferably exhausts approximately 100° F. air at approximately 50 ft$^3$ per minute in order to dissipate approximately 933 watts of thermal heat flow therefrom. The temperature of the exhausted air may reach a maximum of approximately 161° F. if the inlet air is at a temperature of approximately 95° F. Inlet air for the equipment bay is filtered for particulates, but is not nuclear/biological/chemical (NBC) filtered. Exhaust air from the equipment bay may be utilized for air blanket rewarming of a hypothermic medical patient. If equipment bay exhaust air is utilized for rewarming of a hypothermic medical patient, then it is recommended that the upper housing section be removed or substantially opened, so as to limit undesirable breathing of the equipment bay exhaust air.

Optionally, the equipment bay air, after being warmed by the equipment bay, is NBC filtered before being applied to the hot air blanket. In this case, the upper housing section may remain in place and fully closed, so as to provide desirable NBC protection.

A water blanket may optionally be provided above and/or below the patient in order to facilitate hypothermic rewarming. Preferably, a recirculating water/anti-freeze medium is utilized to facilitate heat transfer from a STEPO microcooling system to heat exchanges which cool the air being circulated in the patient compartment. optionally, a heating and cooling circuit can be provided so as to facilitate direction of the water path into a circulating water blanket which is then applied to the patient. A heater would then heat the water/anti-freeze mixture, if desired, prior to mixture flowing into the water blanket. Optionally, a second such blanket may be provided beneath the medical patient, so as to enhance heat transfer.

The padding formed upon the upper surface of the lower housing section optionally comprises heating or temperature controlled pads. Preferably, either circulating water or electrical heating elements are utilized to control the temperature of the pads.

By insulating the outer surface of any blankets utilized to control the temperature of the medical patient, heat loss is mitigated, thereby increasing the efficiency and effectiveness thereof. When the upper housing section 26 is utilized, then such heat loss generally serves to heat the surrounding air, thereby enhancing the efficiency of the temperature control system.

Alternatively, temperature control may be provided via heating with a dry blanket, which itself is preferably either electrically or chemically heated, and which has a wet towel in laminar juxtaposition thereto. The wet towel functions to increase thermal conduction between the dry blanket and the medical patient and also facilitates more even distribution of the heat from the dry blanket.

Optionally, heating modules are utilized to provide for the selective heating of local areas, typically the more densely vascularized regions of the neck, arm pits, groin, behind the knees, etc. At these locations, blood veins are disposed close to the body's surface, thereby facilitating heat transfer to the medical patient without requiring extensive heating of the surrounding tissue. Such undesirably excessive heating increases oxygen demand before the ventilation and circulation supporting medical devices can accommodate such increased demand. Additionally, the use of such modules to facilitate localized heating allow the localized heating to continue while other treatments are performed which require better access to the medical patient than is possible with continuous blanket coverage. That is, while a blanket would have to be removed in order to facilitate the performance of such treatments, thereby at least temporarily terminating heat control of the medical patient, such modules may generally remain in place and effective throughout such medical procedures.

When the upper housing section 26 is in place, then electrical heaters are preferably utilized to heat a circulating fluid so as to provide warmth therein. As those skilled in the art will appreciate, various alternative heating methodologies may likewise be utilized. For example, electrical heating elements may be utilized directly within the upper housing section.

It may be beneficial to provide a transportable life support system according to the present invention at various locations where such is likely to find utility. For example, places where a large number of people are present, e.g., office buildings, industrial plants, sporting events, etc. are likely to the site of an injury, accident, or illness resulting in the need for immediate transportation of the victim to a hospital, while utilizing life support devices. As such, it may be beneficial to store transportable life support systems at various locations throughout a municipality, in the anticipation of such likely use.

Thus, the transportable life support system of the present invention provides a means for transporting an individual medical patient from the site of the injury or the occurrence of a medical problem to a remote hospital. In battlefield applications intensive care is provided for casualties while maintaining chemical and/or biological isolation of the medical patient. Isolation from the environment and/or care givers is also facilitated. Additionally, the transportable life support system of the present invention provides means to reconfigure austere facilities into resuscitative, operative, and post-operative medical care facilities. Thus, various field environments such as shipboard, aircraft, school, home, office, hospital, battlefield, etc. may be effectively converted into medical care facilities because of the autonomous nature of the transportable life support system of the present invention.

The transportable life support system of the present invention provides continuity of care during transport of a medical patient from a site of injury to a hospital or other location where medical care may be provided. Its lightweight facilitate hand carrying and its configuration facilitates interface with various different military evacuation vehicles.

Built-in communications and intelligence provide a head count of injuries and logistics reporting, so as to facilitate enhanced battlefield and civilian emergency management. Intelligent and closed-loop controls automate the medical treatment process, so as to reduce the skill and training required of a resident care giver. Medical monitoring devices and physiological parameter processing facilitates intelligent automated decision making for controlling the operation of medical treatment devices, as well as treatment administration via the care giver. Medical patient and system status are automatically reported via the telecommunications to enhance medical care provided and also further facilitate battlefield and civilian emergency management.

The use of such closed-loop automation and automated intelligent decision making autonomous operation, wherein the care giver may leave the medical patient within the transportable life support system unattended for extended amounts of time. Audible and/or visible alarms notify the care giver in the instance that a condition arises which requires the care giver's immediate attention. Thus, advance levels of intensive care may be provided with minimally trained on-site personnel.

The telecommunications capability of the present invention allow remote medical personnel to monitor the medical patient and to control the medical treatment devices providing care thereto. Such telecommunications may either be automatic, i.e., self-activated in response to the monitoring of medical parameters of the medical patient, or may be initiated by the local care giver. Such telecommunications facilitate reporting of the condition of the medical patient, queries by the local care giver and responses to such queries from remote medical personnel, and control of the medical treatment devices by such remote medical personnel.

It is understood the exemplary transportable life support system described herein and shown in the drawings represents only a presently preferred embodiment of the invention. Indeed, various modifications and additions may be made to such embodiment without departing from the spirit and scope of the invention. For example, various different configurations of the present invention are contemplated. It is contemplated that a housing may be configured so as to accommodate more than one medical patient. Additional medical devices may then be provided, or advantage of the capability of existing medical devices to service more than one person may be taken. Additionally, the upper housing section 26 may be configured so as to be disposable, in the fashion of the roof of a convertible automobile. Additionally, as those skilled in the art will appreciate, various other medical monitoring and/or medical treatment devices may be integrated into the present invention. Thus, these and other modifications and additions may be obvious to those skilled in the art and may be implemented to adapt the present invention for use in a variety of different applications.

The program listing for controlling the microprocessor of the control circuit 46 such that the medical treatment devices are responsive to the medical monitoring devices and such that the medical treatment devices cooperate with one another to provide medical care for the patient are provided as a microfiche appendix hereto.

What is claimed is:

1. A self-contained transportable life support system for resuscitation, stabilization, and transport of a patient, the system comprising:

a) an environmentally controlled housing for receiving and supporting a patient;

b) a plurality of medical monitoring devices disposed within the housing and operatively coupled to the patient, each of the medical monitoring devices being operative to generate a life support signal corresponding to a monitored physiological condition of the patient;

c) a plurality of medical treatment devices disposed within the housing and operatively coupled to the patient, each respective one of the plurality of medical treatment devices being operative to treat a specific physiological function of said patient; and d) a control circuit having a memory with a patient care management algorithm stored therewithin, the control circuit being attached to the housing and in electrical communication with the medical monitoring devices and the medical treatment devices, the patient care management algorithm being operative to direct the control circuit to substantially simultaneously monitor the life support signals generated by the medical monitoring devices and to control the operation of the medical treatment devices such that each respective one of the medical devices is implemented and regulated in response to at least two monitored life support signals wherein at least one monitored life support signal corresponds to a physiological condition selected from the group consisting of the patient's blood pressure, heart rate, respiration rate and volume, inspired and expired carbon dioxide and oxygen, hemoglobin oxygen saturation level, temperature, brain function, and blood chemistry.

2. The self-contained transportable life support system as recited in claim 1, wherein the control circuit is programmably controllable to regulate operation of the medical devices and life support conditions of the patient independent of operator intervention.

3. The self-contained transportable life support system as recited in claim 1, wherein the control circuit is programmably controllable to regulate environmental support conditions within the housing independent of operator intervention.

4. The self-contained transportable life support system as recited in claim 1, further comprising at least one environmental control device disposed within the housing, and in electrical communication with the control circuit, for regulating environmental conditions within the housing.

5. The self-contained transportable life support system as recited in claim 4, wherein the environmental control device comprises a heater for heating an interior portion of the housing so as to maintain the interior portion above a predetermined minimum temperature.

6. The self-contained transportable life support system as recited in claim 4, wherein the environmental control device comprises a cooler for cooling an interior portion of the housing so as to maintain the interior portion below a predetermined maximum temperature.

7. The self-contained transportable life support system as recited in claim 4, wherein the environmental control device comprises an air filtration system for filtering air within the housing to deplete chemical and bacterial contamination within the housing.

8. The self-contained transportable life support system as recited in claim 1, wherein the control system comprises a closed-loop control system.

9. The self-contained transportable life support system as recited in claim 1, further comprising a communication circuit attached to the housing for communicating between the control circuit and a remote station.

10. The self-contained transportable life support system as recited in claim 9, wherein the communication system comprises:
    a) a transmitter for transmitting information representative of patient life support conditions;
    b) a receiver for receiving externally generated remote control signals; and
    c) the control circuit being responsive to regulate operation of the medical devices and environmental conditions within the housing in response to the remote control signals.

11. The self-contained transportable life support system as recited in claim 1, wherein the control circuit comprises:
    a) a general purpose microprocessor; and
    b) a data storage device for storing patient data, medical device data, environmental data, and system data.

12. The self-contained transportable life support system as recited in claim 1, wherein the housing having an interior portion is configured to receive and engage a stretcher, and also having an exterior portion configured to receive and engage vehicular mounted stretcher supports.

13. The self-contained transportable life support system as recited in claim 1, wherein the housing comprises four stretcher retention members disposed within the housing for receiving and engaging a stretcher within the housing.

14. The self-contained transportable life support system as recited in claim 13, wherein each of the stretcher retention members comprise a stretcher engagement mechanism operative to provide locking engagement to the stretcher solely in response to placement of the stretcher upon the stretcher engagement mechanism.

15. The self-contained transportable life support system as recited in claim 1, wherein at least one medical monitoring device comprises:
    a) a temperature monitoring device connectable to a patient for monitoring a body temperature of the patient; and wherein at least one medical treatment device comprises:
    a) a temperature control device connectable to the patient for controlling the body temperature of the patient.

16. The self-contained transportable life support system as recited in claim 15, wherein the temperature control device comprises an extracorporeal blood temperature controller for regulating blood temperature of the patient in response to the temperature monitoring system.

17. The self-contained transportable life support system as recited in claim 15, wherein the temperature control device directs temperature controlled air about the patient in response to the temperature monitoring device, so as to maintain the temperature of the patient within a desired range.

18. The self-contained transportable life support system as recited in claim 1, wherein the housing is sealable to isolate the patient therein from chemical and biological conditions external to the housing.

19. The self-contained transportable life support system as recited in claim 1, further comprising a pressure regulating device disposed within the housing, in electrical communication with the control circuit, for regulating pressure within the housing.

20. The self-contained transportable life support system as recited in claim 1, wherein the control circuit comprises an audio/visual device, at least a portion of which being disposed external to the housing and in electrical communication with the control circuit, for communicating information representative of patient life support conditions.

21. The self-contained transportable life support system as recited in claim 20, wherein the audio/visual device displays treatment instructions in response to operating conditions of the medical devices.

22. The self-contained transportable life support system as recited in claim 1, wherein the control circuit comprises a power regulation circuit for regulating application of electrical power to the medical devices in accordance with an assigned priority status of the medical devices.

23. The self-contained transportable life support system as recited in claim 22, wherein the control circuit is operative to modify the assigned priority status of medical devices in response to the patient life support conditions.

24. The self-contained transportable life support system as recited in claim 1, wherein the control circuit is operative to simulate a plurality of life support conditions, to monitor an operator's utilization of the medical devices in response to the simulated life support conditions, and to evaluate the effectiveness of the operator's utilization of the medical devices.

25. The self-contained transportable life support system as recited in claim 1, wherein the housing comprises at least one of a hyperbaric chamber and a hypobaric chamber.

26. The self-contained transportable life support system as recited in claim 23, wherein the hyperbaric chamber comprises a polymer material.

27. The self-contained transportable life support system as recited in claim 1, wherein the control circuit comprises a medical data reader for receiving medical data from a medical data storage device, the control circuit being operative to regulate operation of the medical devices in response to the received medical data.

28. A method for transporting a patient while providing life support therefor, the method comprising the steps of:
    a) providing an environmentally controlled transportable housing configured to receive and support the patient;
    b) providing a plurality of medical monitoring devices disposed within the housing capable of being operatively coupled to the patient, each of the medical monitoring devices being operative to generate a life support signal corresponding to a monitored physiological condition of the patient;

c) providing a plurality of medical treatment devices within the housing operatively connectable to the patient, each respective one of said plurality of medical treatment devices being operative to treat a specific physiological function of said patient;

d) providing a control circuit attached to the housing and in electrical communication with the medical monitoring devices and the medical treatment devices, said control circuit having a memory with a patient care management algorithm stored therewithin for directing said control circuit to substantially simultaneously monitor the life support signals generated by the medical monitoring devices and to control the operation of the medical treatment devices such that each respective one of said medical treatment devices is implemented and regulated in response to at least two monitored life support signals wherein at least one monitored life support signal corresponds to a physiological condition selected from the group consisting of the patient's blood pressure, heart rate, respiration rate and volume, inspired and expired carbon dioxide and oxygen, hemoglobin oxygen saturation level, temperature, brain function, and blood chemistry; and e) executing said patient care management algorithm.

29. The method as recited in claim 28, further comprising the step of programmably controlling the control circuit so as to regulate operation of the medical devices and life support conditions of the patient independent of simultaneous operator intervention.

30. The method as recited in claim 28, further comprising the step of heating an interior portion of the housing so as to maintain the interior portion above a predetermined minimum temperature.

31. The method as recited in claim 28, further comprising the step of cooling an interior portion of the housing so as to maintain the interior portion below a predetermined maximum temperature.

32. The method as recited in claim 28, further comprising the step of filtering the air within the housing.

33. The method as recited in claim 28, wherein the step of regulating operation of the medical devices comprises regulating operation of the medical devices via a closed-loop control system.

34. The method as recited in claim 28, further comprising the step of communicating between the control circuit and a remote location.

35. The method as recited in claim 34, wherein the step of communicating comprises:

a) transmitting information representative of patient life support conditions;

b) receiving externally generated remote control signals; and c) the control circuit responding to the remote control signals, such that patient life support conditions are regulatable in response to the remote control signals.

36. The method as recited in claim 28, wherein the step of regulating operation of the medical devices comprises regulating operation of the medical devices with a general purpose microprocessor.

37. The method as recited in claim 28, further comprising the steps of receiving and engaging a stretcher within the housing and engaging the housing with vehicle mounted stretcher supports.

38. The method as recited in claim 28, further comprising the steps of receiving and engaging a stretcher within the housing.

39. The method as recited in claim 38, wherein the step of engaging a stretcher comprises providing locking engagement of the housing to the stretcher solely in response to placement of the stretcher upon a stretcher engagement mechanism.

40. The method as recited in claim 28, further comprising the steps of:

a) monitoring a body temperature of the patient; and b) controlling the body temperature of the patient.

41. The method as recited in claim 40, wherein the step of controlling the body temperature of the patient comprises controlling the body temperature of the patient via an extracorporeal blood temperature controller for regulating blood temperature of the patient in response to the temperature monitoring system.

42. The method as recited in claim 40, wherein the step of controlling the body temperature of the patient comprises controlling the body temperature of the patient via a temperature controlled water jacket.

43. The method as recited in claim 40, wherein the step of controlling the body temperature of the patient comprises directing temperature controlled air about the patient in response to the temperature monitoring system, so as to maintain the temperature of the patient within a desired range.

44. The method as recited in claim 28, further comprising the step of sealing the housing so as to isolate the patient therein from chemical and biological conditions external to the housing.

45. The method as recited in claim 28, further comprising the step of regulating the pressure within the housing.

46. The method as recited in claim 28, further comprising the step of displaying patient life support conditions.

47. The method as recited in claim 46, further comprising the step of displaying treatment instructions in response to patient life support conditions.

48. The method as recited in claim 28, wherein the step of regulating operation of the medical devices comprises regulating application of electric power to the medical devices in accordance with an assigned priority status of the medical devices.

49. The method as recited in claim 48, further comprising the step of modifying the assigned priority status of the medical devices in response to patient life support conditions.

50. The method as recited in claim 28, further comprising the step of simulating a plurality of life support conditions via the control circuit and monitoring an operator's utilization of the medical devices in response to the simulated life support conditions to evaluate the effectivess of the operator's utilization of the medical devices.

51. The method as recited in claim 28, wherein the step of receiving the patient within an environmentally controlled housing comprises receiving the patient within one of a hyperbaric chamber and a hypobaric chamber.

52. The method as recited in claim 51, wherein the step of receiving the patient within a hyperbaric chamber comprises receiving the patient within a hyperbaric chamber comprised of a polymer material.

53. The method as recited in claim 28, further comprising the step of receiving medical data from a medical data storage device via a medical data reader, the control circuit being operative to regulate operation of the medical devices in response to the received medical data.

* * * * *